US009592250B2

(12) United States Patent
Woolf et al.

(10) Patent No.: US 9,592,250 B2
(45) Date of Patent: Mar. 14, 2017

(54) DOUBLE-STRANDED OLIGONUCLEOTIDES

(71) Applicant: LIFE TECHNOLOGIES CORPORATION, Carlsbad, CA (US)

(72) Inventors: Tod Woolf, Sudbury, MA (US); Kristin Wiederholt, Vista, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/446,022

(22) Filed: Jul. 29, 2014

(65) Prior Publication Data

US 2015/0057333 A1 Feb. 26, 2015

Related U.S. Application Data

(63) Continuation of application No. 13/277,957, filed on Oct. 20, 2011, now Pat. No. 8,815,821, which is a continuation of application No. 12/062,380, filed on Apr. 3, 2008, now abandoned, which is a continuation of application No. 11/049,636, filed on Feb. 2, 2005, now abandoned, which is a continuation-in-part of application No. 10/357,529, filed on Feb. 3, 2003, now abandoned, and a continuation-in-part of application No. 10/357,826, filed on Feb. 3, 2003, now abandoned.

(60) Provisional application No. 60/540,552, filed on Feb. 2, 2004, provisional application No. 60/615,408, filed on Sep. 30, 2004, provisional application No. 60/438,608, filed on Jan. 7, 2003, provisional application No. 60/436,238, filed on Dec. 23, 2002, provisional application No. 60/353,381, filed on Feb. 1, 2002, provisional application No. 60/353,203, filed on Feb. 1, 2002.

(51) Int. Cl.
*C12N 15/11* (2006.01)
*A61K 31/713* (2006.01)
*C12N 15/113* (2010.01)

(52) U.S. Cl.
CPC .......... *A61K 31/713* (2013.01); *C12N 15/111* (2013.01); *C12N 15/113* (2013.01); *C12N 15/1135* (2013.01); *C12N 15/1137* (2013.01); *C12Y 207/11022* (2013.01); *C12Y 301/03048* (2013.01); *C12N 2310/11* (2013.01); *C12N 2310/14* (2013.01); *C12N 2310/315* (2013.01); *C12N 2310/321* (2013.01); *C12N 2310/53* (2013.01); *C12N 2320/31* (2013.01); *C12N 2320/50* (2013.01); *C12N 2320/51* (2013.01)

(58) Field of Classification Search
CPC .................. C12N 15/113; C12N 2310/14
See application file for complete search history.

(56) References Cited

U.S. PATENT DOCUMENTS

| 4,235,871 A | 11/1980 | Papahadjopoulos |
| 4,415,732 A | 11/1983 | Caruthers et al. |
| 4,458,066 A | 7/1984 | Caruthers et al. |
| 4,501,728 A | 2/1985 | Geho et al. |
| 4,554,101 A | 11/1985 | Hopp |
| 4,659,774 A | 4/1987 | Webb et al. |
| 4,661,450 A | 4/1987 | Kempe et al. |
| 4,682,195 A | 7/1987 | Yimaz |
| 4,683,195 A | 7/1987 | Mullis et al. |
| 4,683,202 A | 7/1987 | Mullis et al. |
| 4,684,611 A | 8/1987 | Schilperoort et al. |
| 4,704,362 A | 11/1987 | Itakura et al. |
| 4,737,323 A | 4/1988 | Martin et al. |
| 4,786,600 A | 11/1988 | Kramer |
| 4,800,159 A | 1/1989 | Mullis et al. |
| 4,816,571 A | 3/1989 | Andrus et al. |
| 4,828,979 A | 5/1989 | Kievan et al. |
| 4,837,028 A | 6/1989 | Allen |
| 4,847,240 A | 7/1989 | Ryser |
| 4,849,513 A | 7/1989 | Smith et al. |
| 4,883,750 A | 11/1989 | Whiteley et al. |
| 4,897,355 A | 1/1990 | Eppstein et al. |
| 4,910,300 A | 3/1990 | Urdea et al. |
| 4,952,496 A | 8/1990 | Studier et al. |
| 4,952,500 A | 8/1990 | Finnerty et al. |
| 4,959,463 A | 9/1990 | Froehler et al. |
| 5,013,830 A | 5/1991 | Ohtsuka |
| 5,026,645 A | 6/1991 | Kotani et al. |
| 5,037,735 A | 8/1991 | Khanna et al. |
| 5,037,745 A | 8/1991 | McAllister |
| 5,063,209 A | 11/1991 | Carter |
| 5,102,802 A | 4/1992 | McAllister |
| 5,141,813 A | 8/1992 | Nelson |
| 5,214,135 A | 5/1993 | Srivastava |

(Continued)

FOREIGN PATENT DOCUMENTS

| CA | 2473944 | 7/2003 |
| EP | 0178863 | 4/1986 |

(Continued)

OTHER PUBLICATIONS

Amarzguioui et al. "Tolerance for Mutationws and Chemical Modification in a siRNA", *Nucleic Acids Research*, vol. 31, No. 2, 2003, 589-595.
Ambion, TechNotes, vol. 9, No. 3, Jun. 2002, 1-19.
Ambion, TechNotes, vol. 9, No. 4, Jun. 2002, 1-19.
Ambion, "Design and testing of siRNAs", TechNotes, vol. 9, No. 1, Feb. 2002, 4 (1-2 pages).
Ambion, "Design and testing siRNAs", TechNotes, vol. 8, No. 5, Nov. 2001, 1-3.
Ambion, "Enhanced siRNA Delivery and Long-Term Gene Silencing", TechNotes, vol. 12, No. 1, 2003, 22-25.

(Continued)

*Primary Examiner* — Brian Whiteman

(57) ABSTRACT

Antisense sequences, including duplex RNAi compositions, which possess improved properties over those taught in the prior art are disclosed. The invention provides optimized antisense oligomer compositions and method for making and using the both in in vitro systems and therapeutically. The invention also provides methods of making and using the improved antisense oligomer compositions.

16 Claims, 14 Drawing Sheets

(56) References Cited

U.S. PATENT DOCUMENTS

| | | |
|---|---|---|
| 5,214,136 A | 5/1993 | Lin et al. |
| 5,221,619 A | 6/1993 | Itakura et al. |
| 5,223,618 A | 6/1993 | Cook et al. |
| 5,231,168 A | 7/1993 | Dziegiel et al. |
| 5,240,846 A | 8/1993 | Collins et al. |
| 5,241,060 A | 8/1993 | Engelhardt et al. |
| 5,260,433 A | 11/1993 | Engelhardt et al. |
| 5,264,423 A | 11/1993 | Cohen et al. |
| 5,264,566 A | 11/1993 | Froehler et al. |
| 5,276,019 A | 1/1994 | Cohen et al. |
| 5,279,721 A | 1/1994 | Schmid |
| 5,302,523 A | 4/1994 | Coffee et al. |
| 5,322,783 A | 6/1994 | Tomes et al. |
| 5,378,825 A | 1/1995 | Cook et al. |
| 5,384,253 A | 1/1995 | Krzyzek et al. |
| 5,391,723 A | 2/1995 | Priest |
| 5,407,808 A | 4/1995 | Halling et al. |
| 5,428,148 A | 6/1995 | Reddy et al. |
| 5,446,137 A | 8/1995 | Maag et al. |
| 5,464,765 A | 11/1995 | Coffee et al. |
| 5,466,786 A | 11/1995 | Buhr et al. |
| 5,470,967 A | 11/1995 | Huie et al. |
| 5,480,980 A | 1/1996 | Seela |
| 5,489,527 A | 2/1996 | Wilson |
| 5,506,212 A | 4/1996 | Hoke et al. |
| 5,514,788 A | 5/1996 | Bennett et al. |
| 5,525,719 A | 6/1996 | Srivastava et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,565,350 A | 10/1996 | Kmiec |
| 5,573,913 A | 11/1996 | Rosemeyer et al. |
| 5,574,146 A | 11/1996 | Reddy et al. |
| 5,580,859 A | 12/1996 | Felgner et al. |
| 5,583,013 A | 12/1996 | Itakura et al. |
| 5,589,466 A | 12/1996 | Felgner et al. |
| 5,591,616 A | 1/1997 | Hiei et al. |
| 5,594,121 A | 1/1997 | Froehler et al. |
| 5,594,122 A | 1/1997 | Friesen |
| RE35,443 E | 2/1997 | DeFrancesco et al. |
| 5,602,240 A | 2/1997 | De Mesmaeker et al. |
| 5,602,244 A | 2/1997 | Caruthers et al. |
| 5,610,042 A | 3/1997 | Chang et al. |
| 5,610,289 A | 3/1997 | Cook et al. |
| 5,614,503 A | 3/1997 | Chaudhary et al. |
| 5,614,617 A | 3/1997 | Cook et al. |
| 5,623,070 A | 4/1997 | Cook et al. |
| 5,624,803 A | 4/1997 | Noonberg et al. |
| 5,637,683 A | 6/1997 | Usher et al. |
| 5,643,768 A | 7/1997 | Kawasaki |
| 5,645,897 A | 7/1997 | Andra |
| 5,652,099 A | 7/1997 | Conrad |
| 5,656,610 A | 8/1997 | Shuler et al. |
| 5,670,633 A | 9/1997 | Cook et al. |
| 5,670,663 A | 9/1997 | Durzan et al. |
| 5,672,697 A | 9/1997 | Buhr et al. |
| 5,677,124 A | 10/1997 | DuBois et al. |
| 5,681,947 A | 10/1997 | Bergstrom et al. |
| 5,700,922 A | 12/1997 | Cook |
| 5,702,932 A | 12/1997 | Hoy et al. |
| 5,705,629 A | 1/1998 | Bhongle |
| 5,708,154 A | 1/1998 | Smith et al. |
| 5,712,257 A | 1/1998 | Carter |
| 5,714,606 A | 2/1998 | Acevedo et al. |
| 5,728,525 A | 3/1998 | Conrad |
| 5,734,039 A | 3/1998 | Calabretta |
| 5,734,040 A | 3/1998 | Weeks et al. |
| 5,736,131 A | 4/1998 | Bosch et al. |
| 5,736,392 A | 4/1998 | Hawley-Nelson et al. |
| 5,736,524 A | 4/1998 | Content et al. |
| 5,744,595 A | 4/1998 | Srivastava et al. |
| 5,763,167 A | 6/1998 | Conrad |
| 5,767,099 A | 6/1998 | Harris et al. |
| 5,776,905 A | 7/1998 | Gibbons et al. |
| 5,777,092 A | 7/1998 | Cook et al. |
| 5,777,153 A | 7/1998 | Lin et al. |
| 5,780,053 A | 7/1998 | Ashley et al. |
| 5,780,448 A | 7/1998 | Davis |
| 5,789,215 A | 8/1998 | Berns et al. |
| 5,792,847 A | 8/1998 | Buhr et al. |
| 5,795,715 A | 8/1998 | Livache et al. |
| 5,795,737 A | 8/1998 | Seed et al. |
| 5,801,154 A | 9/1998 | Baracchini et al. |
| 5,824,528 A | 10/1998 | Studier et al. |
| 5,830,430 A | 11/1998 | Unger et al. |
| 5,830,653 A | 11/1998 | Froehler et al. |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,849,902 A | 12/1998 | Arrow et al. |
| 5,851,548 A | 12/1998 | Dattagupta |
| 5,853,990 A | 12/1998 | Winger et al. |
| 5,853,992 A | 12/1998 | Glazer et al. |
| 5,853,993 A | 12/1998 | Dellinger et al. |
| 5,855,910 A | 1/1999 | Ashley et al. |
| 5,856,092 A | 1/1999 | Dale et al. |
| 5,858,652 A | 1/1999 | Laffler et al. |
| 5,858,988 A | 1/1999 | Wang |
| 5,859,221 A | 1/1999 | Cook et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,366 A | 2/1999 | Kallender |
| 5,869,320 A | 2/1999 | Studier et al. |
| 5,872,232 A | 2/1999 | Cook et al. |
| 5,882,864 A | 3/1999 | An et al. |
| 5,885,834 A | 3/1999 | Epstein |
| 5,886,165 A | 3/1999 | Kandimalla et al. |
| 5,889,136 A | 3/1999 | Scaringe et al. |
| 5,891,681 A | 4/1999 | Mallet et al. |
| 5,898,031 A | 4/1999 | Crooke |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson |
| 5,919,630 A | 7/1999 | Nadeau et al. |
| 5,922,574 A | 7/1999 | Minter |
| 5,925,517 A | 7/1999 | Tyagi et al. |
| 5,928,862 A | 7/1999 | Morrison |
| 5,928,869 A | 7/1999 | Nadeau et al. |
| 5,928,905 A | 7/1999 | Stemmer et al. |
| 5,928,906 A | 7/1999 | Koster et al. |
| 5,929,042 A | 7/1999 | Troy et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,955,589 A | 9/1999 | Cook et al. |
| 5,965,720 A | 10/1999 | Gryaznov et al. |
| 5,981,274 A | 11/1999 | Tyrrell et al. |
| 5,990,479 A | 11/1999 | Weiss et al. |
| 5,994,624 A | 11/1999 | Trolinder et al. |
| 5,998,135 A | 12/1999 | Rabbani et al. |

(56) References Cited

U.S. PATENT DOCUMENTS

| | | |
|---|---|---|
| 5,998,203 A | 12/1999 | Matulic-Adamic et al. |
| 6,005,087 A | 12/1999 | Cook et al. |
| 6,015,886 A | 1/2000 | Dale et al. |
| 6,015,893 A | 1/2000 | Cance et al. |
| 6,037,463 A | 3/2000 | Uhlmann et al. |
| 6,048,974 A | 4/2000 | Gryaznov et al. |
| 6,051,386 A | 4/2000 | Lerner |
| 6,083,482 A | 7/2000 | Wang |
| 6,087,484 A | 7/2000 | Goodchild |
| 6,107,094 A | 8/2000 | Crooke |
| 6,114,152 A | 9/2000 | Serafini et al. |
| 6,127,124 A | 10/2000 | Leeds et al. |
| 6,133,024 A | 10/2000 | Helene et al. |
| 6,214,804 B1 | 4/2001 | Felgner et al. |
| 6,248,724 B1 | 6/2001 | Moore et al. |
| 6,251,666 B1 | 6/2001 | Beigelman |
| 6,251,873 B1 | 6/2001 | Furusako et al. |
| 6,262,252 B1 | 7/2001 | Wolff et al. |
| 6,268,490 B1 | 7/2001 | Imanishi et al. |
| 6,372,433 B1 | 4/2002 | Baker et al. |
| 6,376,179 B1 | 4/2002 | Laayoun |
| 6,455,292 B1 | 9/2002 | Shu et al. |
| 6,489,307 B1 | 12/2002 | Phillips et al. |
| 6,495,663 B1 | 12/2002 | Rothbard et al. |
| 6,506,559 B1 | 1/2003 | Fire et al. |
| 6,525,191 B1 | 2/2003 | Ramasamy |
| 6,545,048 B1 | 4/2003 | Patterson et al. |
| 6,573,099 B2 | 6/2003 | Graham |
| 6,573,374 B1 | 6/2003 | Muehlegger et al. |
| 6,579,856 B2 | 6/2003 | Mercola |
| 6,638,767 B2 | 10/2003 | Unger et al. |
| 6,639,059 B1 | 10/2003 | Kochkine et al. |
| 6,670,461 B1 | 12/2003 | Wengel et al. |
| 6,673,611 B2 | 1/2004 | Thompson et al. |
| 6,680,301 B2 | 1/2004 | Berg et al. |
| 6,734,291 B2 | 5/2004 | Kochkine et al. |
| 6,753,139 B1 | 6/2004 | Baulcombe et al. |
| 6,770,748 B2 | 8/2004 | Imanishi et al. |
| 6,794,499 B2 | 9/2004 | Wengel et al. |
| 6,841,579 B1 | 1/2005 | Plowman et al. |
| 6,849,726 B2 | 2/2005 | Usman et al. |
| 6,953,656 B2 | 10/2005 | Jacobson et al. |
| 7,022,828 B2 | 4/2006 | McSwiggen et al. |
| 7,034,133 B2 | 4/2006 | Wengel et al. |
| 7,053,207 B2 | 5/2006 | Wengel |
| 7,056,704 B2 | 6/2006 | Tuschl et al. |
| 7,060,809 B2 | 6/2006 | Wengel et al. |
| 7,074,558 B2 | 7/2006 | Haydock et al. |
| 7,078,196 B2 | 7/2006 | Tuschl et al. |
| 7,084,125 B2 | 8/2006 | Wengel |
| 7,125,664 B2 | 10/2006 | Mine-Golomb |
| 7,176,304 B2 | 2/2007 | McSwiggen et al. |
| 7,208,306 B2 | 4/2007 | Liu et al. |
| 7,341,835 B2 | 3/2008 | Blume et al. |
| 7,368,240 B2 | 5/2008 | Van et al. |
| 7,399,586 B2 | 7/2008 | Klinghoffer et al. |
| 7,452,987 B2 | 11/2008 | Giese et al. |
| 7,528,118 B2 | 5/2009 | Soutschek et al. |
| 7,538,095 B2 | 5/2009 | Fire et al. |
| 7,553,830 B2 | 6/2009 | Beigelman et al. |
| 7,556,944 B2 | 7/2009 | Myers et al. |
| 7,560,438 B2 | 7/2009 | Fire et al. |
| 7,566,700 B2 | 7/2009 | Walker et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,576,119 B2 | 8/2009 | Ravikumar et al. |
| 7,576,262 B2 | 8/2009 | Wang et al. |
| 7,579,451 B2 | 8/2009 | Manoharan et al. |
| 7,582,744 B2 | 9/2009 | Manoharan et al. |
| 7,582,745 B2 | 9/2009 | Sah et al. |
| 7,585,834 B2 | 9/2009 | Wender et al. |
| 7,592,322 B2 | 9/2009 | Barik |
| 7,595,387 B2 | 9/2009 | Leake et al. |
| 7,598,370 B2 | 10/2009 | Khvorova et al. |
| 7,615,618 B2 | 11/2009 | Manoharan et al. |
| 7,622,633 B2 | 11/2009 | Fire et al. |
| 7,626,014 B2 | 12/2009 | Manoharan et al. |
| 7,629,321 B2 | 12/2009 | Crooke |
| 7,632,932 B2 | 12/2009 | Manoharan et al. |
| 7,635,769 B2 | 12/2009 | Uhlmann et al. |
| 7,659,391 B2 | 2/2010 | De Backer et al. |
| 7,687,617 B2 | 3/2010 | Thrue et al. |
| 7,691,997 B2 | 4/2010 | Khvorova et al. |
| 7,695,902 B2 | 4/2010 | Crooke |
| 7,695,964 B2 | 4/2010 | Maina et al. |
| 7,696,345 B2 | 4/2010 | Allerson et al. |
| 7,700,758 B2 | 4/2010 | Tzertzinis et al. |
| 7,704,688 B2 | 4/2010 | Baulcombe et al. |
| 7,723,512 B2 | 5/2010 | Manoharan |
| 7,732,417 B2 | 6/2010 | Beach et al. |
| 7,732,593 B2 | 6/2010 | Zamore et al. |
| 7,737,125 B2 | 6/2010 | Worm |
| 7,745,608 B2 | 6/2010 | Manoharan et al. |
| 7,750,144 B2 | 7/2010 | Zamore et al. |
| 7,763,590 B2 | 7/2010 | Kreutzer |
| 7,770,756 B2 | 8/2010 | Cook et al. |
| 7,772,203 B2 | 8/2010 | Zamore et al. |
| 7,772,387 B2 | 8/2010 | Manoharan et al. |
| 7,786,290 B2 | 8/2010 | Woppmann et al. |
| 7,790,691 B2 | 9/2010 | Kraynack et al. |
| 7,790,878 B2 | 9/2010 | Barik |
| 7,795,422 B2 | 9/2010 | McSwiggen et al. |
| 7,795,423 B2 | 9/2010 | Heindl et al. |
| 7,803,930 B2 | 9/2010 | Crooke et al. |
| 7,812,149 B2 | 10/2010 | Prakash et al. |
| 7,820,632 B2 | 10/2010 | Rossi et al. |
| 7,820,809 B2 | 10/2010 | Khvorova et al. |
| 7,829,693 B2 | 11/2010 | Kreutzer et al. |
| 7,834,170 B2 | 11/2010 | Khvorova et al. |
| 7,834,171 B2 | 11/2010 | Leake et al. |
| 7,919,612 B2 | 4/2011 | Baker et al. |
| 7,923,206 B2 | 4/2011 | Robertson et al. |
| 7,923,207 B2 | 4/2011 | Robertson et al. |
| 7,923,547 B2 | 4/2011 | McSwiggen et al. |
| 7,928,217 B2 | 4/2011 | Vornlocher et al. |
| 7,956,176 B2 | 6/2011 | McSwiggen et al. |
| 7,964,578 B2 | 6/2011 | Vargeese et al. |
| 7,989,612 B2 | 8/2011 | McSwiggen et al. |
| 8,058,255 B2 | 11/2011 | Ford et al. |
| 8,084,599 B2 | 12/2011 | Rossi et al. |
| 8,090,542 B2 | 1/2012 | Khvorova et al. |
| 8,097,710 B2 | 1/2012 | Baulcombe et al. |
| 8,101,348 B2 | 1/2012 | Tuschl et al. |
| 8,101,584 B2 | 1/2012 | Kreutzer et al. |
| 8,119,608 B2 | 2/2012 | Kreutzer et al. |
| 8,119,610 B2 | 2/2012 | Yang et al. |
| 8,168,776 B2 | 5/2012 | Kreutzer et al. |
| 8,202,979 B2 | 6/2012 | McSwiggen et al. |
| 8,202,980 B2 | 6/2012 | Kreutzer et al. |
| 8,258,285 B2 | 9/2012 | Baulcombe et al. |
| 8,263,569 B2 | 9/2012 | Baulcombe et al. |
| 8,299,235 B2 | 10/2012 | Baulcombe et al. |
| 8,349,607 B2 | 1/2013 | Baulcombe et al. |
| 8,524,680 B2 | 9/2013 | Brown et al. |
| 8,598,332 B1 | 12/2013 | Waterhouse et al. |
| 8,604,183 B2 | 12/2013 | Allerson et al. |
| 8,759,102 B2 | 6/2014 | Baulcombe et al. |
| 8,779,236 B2 | 7/2014 | Baulcombe et al. |
| 2002/0086356 A1 | 7/2002 | Tuschl et al. |
| 2002/0162126 A1 | 10/2002 | Beach et al. |
| 2002/0165189 A1 | 11/2002 | Crooke |
| 2002/0173478 A1 | 11/2002 | Gewirtz |
| 2002/0197641 A1 | 12/2002 | Minc-Golomb |
| 2003/0009295 A1 | 1/2003 | Markowitz et al. |
| 2003/0032593 A1 | 2/2003 | Wender et al. |
| 2003/0044941 A1 | 3/2003 | Crooke |
| 2003/0077609 A1 | 4/2003 | Jakobsen et al. |
| 2003/0092905 A1 | 5/2003 | Kochkine et al. |
| 2003/0108923 A1 | 6/2003 | Tuschl et al. |
| 2003/0119104 A1 | 6/2003 | Perkins et al. |
| 2003/0142938 A1 | 7/2003 | Koyano et al. |
| 2003/0143732 A1 | 7/2003 | Fosnaugh et al. |
| 2003/0153519 A1 | 8/2003 | Kay et al. |

(56) References Cited

U.S. PATENT DOCUMENTS

| | | |
|---|---|---|
| 2003/0166282 A1 | 9/2003 | Brown |
| 2003/0203868 A1 | 10/2003 | Bushman et al. |
| 2003/0224377 A1 | 12/2003 | Wengel et al. |
| 2003/0224432 A1 | 12/2003 | Myers et al. |
| 2004/0014108 A1 | 1/2004 | Eldrup et al. |
| 2004/0014113 A1 | 1/2004 | Yang et al. |
| 2004/0014956 A1 | 1/2004 | Woolf et al. |
| 2004/0029275 A1 | 2/2004 | Brown et al. |
| 2004/0033602 A1 | 2/2004 | Ford et al. |
| 2004/0038921 A1 | 2/2004 | Kreutzer et al. |
| 2004/0053875 A1 | 3/2004 | Kreutzer et al. |
| 2004/0054155 A1 | 3/2004 | Woolf et al. |
| 2004/0058886 A1 | 3/2004 | Scaringe |
| 2004/0067882 A1 | 4/2004 | Alsobrook et al. |
| 2004/0072779 A1 | 4/2004 | Kreutzer et al. |
| 2004/0078836 A1 | 4/2004 | Farese, Jr. et al. |
| 2004/0091926 A1 | 5/2004 | Liu et al. |
| 2004/0096843 A1 | 5/2004 | Rossi et al. |
| 2004/0102408 A1 | 5/2004 | Kreutzer et al. |
| 2004/0147022 A1 | 7/2004 | Baker et al. |
| 2004/0171031 A1 | 9/2004 | Baker et al. |
| 2004/0171033 A1 | 9/2004 | Baker et al. |
| 2004/0171570 A1 | 9/2004 | Allerson et al. |
| 2004/0175703 A1 | 9/2004 | Kreutzer et al. |
| 2004/0176282 A1 | 9/2004 | Dalby et al. |
| 2004/0180351 A1 | 9/2004 | Giese et al. |
| 2004/0192626 A1 | 9/2004 | McSwiggen et al. |
| 2004/0198640 A1 | 10/2004 | Leake et al. |
| 2004/0203024 A1 | 10/2004 | Baker et al. |
| 2004/0203145 A1 | 10/2004 | Zamore et al. |
| 2004/0219565 A1 | 11/2004 | Kauppinen et al. |
| 2004/0224405 A1 | 11/2004 | Leake et al. |
| 2004/0229266 A1 | 11/2004 | Tuschl et al. |
| 2004/0248094 A1 | 12/2004 | Ford et al. |
| 2004/0248299 A1 | 12/2004 | Jayasena et al. |
| 2004/0259097 A1 | 12/2004 | De Backer et al. |
| 2004/0259209 A1 | 12/2004 | Sun et al. |
| 2004/0259247 A1 | 12/2004 | Tuschl et al. |
| 2005/0020521 A1 | 1/2005 | Rana |
| 2005/0020525 A1 | 1/2005 | McSwiggen et al. |
| 2005/0026160 A1 | 2/2005 | Allerson et al. |
| 2005/0026278 A1 | 2/2005 | Tuschl et al. |
| 2005/0058982 A1 | 3/2005 | Han et al. |
| 2005/0080246 A1 | 4/2005 | Allerson et al. |
| 2005/0100907 A1 | 5/2005 | Kreutzer et al. |
| 2005/0107325 A1 | 5/2005 | Manoharan et al. |
| 2005/0119214 A1 | 6/2005 | Manoharan et al. |
| 2005/0130201 A1 | 6/2005 | Deras et al. |
| 2005/0176018 A1 | 8/2005 | Thompson et al. |
| 2005/0176045 A1 | 8/2005 | Fedorov et al. |
| 2005/0203043 A1 | 9/2005 | Fedorov et al. |
| 2005/0214823 A1 | 9/2005 | Blume et al. |
| 2005/0223427 A1 | 10/2005 | Leake et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0245475 A1 | 11/2005 | Khvorova et al. |
| 2005/0246794 A1 | 11/2005 | Khvorova et al. |
| 2005/0255487 A1 | 11/2005 | Khvorova et al. |
| 2005/0256071 A1 | 11/2005 | Davis |
| 2005/0287566 A1 | 12/2005 | Wengel et al. |
| 2006/0009409 A1 | 1/2006 | Wolf et al. |
| 2006/0134787 A1 | 6/2006 | Zamore et al. |
| 2006/0142228 A1 | 6/2006 | Ford et al. |
| 2006/0166910 A1 | 7/2006 | Tuschl et al. |
| 2006/0217334 A1 | 9/2006 | McSwiggen et al. |
| 2006/0217335 A1 | 9/2006 | McSwiggen et al. |
| 2006/0217336 A1 | 9/2006 | McSwiggen et al. |
| 2006/0217337 A1 | 9/2006 | McSwiggen et al. |
| 2006/0223777 A1 | 10/2006 | Vermeulen et al. |
| 2006/0247428 A1 | 11/2006 | McSwiggen et al. |
| 2006/0247429 A1 | 11/2006 | McSwiggen et al. |
| 2006/0276635 A1 | 12/2006 | McSwiggen et al. |
| 2006/0287266 A1 | 12/2006 | McSwiggen et al. |
| 2006/0293271 A1 | 12/2006 | McSwiggen et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0004663 A1 | 1/2007 | McSwiggen et al. |
| 2007/0004665 A1 | 1/2007 | McSwiggen et al. |
| 2007/0004667 A1 | 1/2007 | McSwiggen et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0111228 A1 | 5/2007 | Jayasena et al. |
| 2007/0167384 A1 | 7/2007 | Leake et al. |
| 2007/0173476 A1 | 7/2007 | Leake et al. |
| 2007/0265438 A1 | 11/2007 | Khvorova et al. |
| 2008/0086002 A1 | 4/2008 | Khvorova et al. |
| 2008/0160594 A1 | 7/2008 | Woolf |
| 2009/0023216 A1 | 1/2009 | Woolf |
| 2009/0093433 A1 | 4/2009 | Woolf et al. |
| 2010/0075423 A1 | 3/2010 | Ford et al. |
| 2010/0136695 A1 | 6/2010 | Woolf |
| 2010/0159591 A1 | 6/2010 | Ford et al. |
| 2010/0184039 A1 | 7/2010 | Ford et al. |
| 2010/0221789 A1 | 9/2010 | Brown et al. |
| 2010/0298408 A1 | 11/2010 | Woolf et al. |
| 2011/0151558 A1 | 6/2011 | Brown et al. |
| 2012/0028312 A1 | 2/2012 | Ford et al. |
| 2012/0107897 A1 | 5/2012 | Woolf et al. |
| 2012/0122217 A1 | 5/2012 | Brown et al. |
| 2013/0230920 A1 | 9/2013 | Ford et al. |
| 2013/0231266 A1 | 9/2013 | Brown et al. |
| 2013/0303586 A1 | 11/2013 | Woolf et al. |
| 2014/0099715 A1 | 4/2014 | Brown |
| 2014/0295543 A1 | 10/2014 | Ford et al. |
| 2015/0099797 A1 | 4/2015 | Woolf et al. |

FOREIGN PATENT DOCUMENTS

| | | |
|---|---|---|
| EP | 0204401 | 12/1986 |
| EP | 0266032 | 5/1988 |
| EP | 0286224 | 10/1988 |
| EP | 0726319 | 4/2001 |
| EP | 1560931 | 6/2002 |
| EP | 0990903 | 3/2003 |
| EP | 1470148 | 8/2003 |
| EP | 1389637 | 2/2004 |
| EP | 1606406 | 9/2004 |
| EP | 1532271 | 4/2005 |
| EP | 1572902 | 8/2005 |
| EP | 1718747 | 11/2006 |
| EP | 1550719 | 12/2008 |
| EP | 1478656 | 9/2009 |
| EP | 1537227 | 2/2010 |
| EP | 2213292 | 8/2010 |
| EP | 2213737 | 8/2010 |
| EP | 2128248 | 5/2011 |
| EP | 2348134 | 7/2011 |
| EP | 2351836 | 8/2011 |
| EP | 2221377 | 10/2011 |
| EP | 2455467 | 5/2012 |
| GB | 2202328 | 9/1988 |
| GB | 2406169 | 3/2005 |
| JP | 4527984 | 8/2010 |
| WO | WO8810315 | 12/1988 |
| WO | WO9014074 | 11/1990 |
| WO | WO9102818 | 3/1991 |
| WO | WO9105866 | 5/1991 |
| WO | WO9116024 | 10/1991 |
| WO | WO9117424 | 11/1991 |
| WO | WO9203464 | 3/1992 |
| WO | WO9203568 | 3/1992 |
| WO | WO9309236 | 5/1993 |
| WO | WO9401550 | 1/1994 |
| WO | WO9408003 | 4/1994 |
| WO | WO9423028 | 10/1994 |
| WO | WO9510305 | 4/1995 |
| WO | WO9518139 | 7/1995 |
| WO | WO9522533 | 8/1995 |
| WO | WO9607432 | 3/1996 |
| WO | WO9711085 | 3/1997 |

(56) References Cited

FOREIGN PATENT DOCUMENTS

| | | |
|---|---|---|
| WO | WO9800547 | 1/1998 |
| WO | WO9801898 | 1/1998 |
| WO | WO9813526 | 4/1998 |
| WO | WO9904775 | 2/1999 |
| WO | WO9914346 | 3/1999 |
| WO | WO9920298 | 4/1999 |
| WO | WO9932619 | 7/1999 |
| WO | WO9934831 | 7/1999 |
| WO | WO9949029 | 9/1999 |
| WO | WO9953050 | 10/1999 |
| WO | WO0001846 | 1/2000 |
| WO | WO0017346 | 3/2000 |
| WO | WO0026413 | 5/2000 |
| WO | WO0027422 | 5/2000 |
| WO | WO0044895 | 8/2000 |
| WO | WO0044914 | 8/2000 |
| WO | WO0052904 | 9/2000 |
| WO | WO0054802 | 9/2000 |
| WO | WO0055378 | 9/2000 |
| WO | WO0061595 | 10/2000 |
| WO | WO0063364 | 10/2000 |
| WO | WO0066364 | 10/2000 |
| WO | WO0125422 | 4/2001 |
| WO | WO0136646 | 5/2001 |
| WO | WO0146473 | 6/2001 |
| WO | WO0152904 | 7/2001 |
| WO | WO0168836 | 9/2001 |
| WO | WO0172995 | 10/2001 |
| WO | WO0175164 | 10/2001 |
| WO | WO0196584 | 12/2001 |
| WO | WO0244321 | 6/2002 |
| WO | WO02094848 | 11/2002 |
| WO | WO03008576 | 1/2003 |
| WO | WO03064626 | 7/2003 |
| WO | WO03064621 | 8/2003 |
| WO | WO03064625 | 8/2003 |
| WO | WO03070918 | 8/2003 |
| WO | WO03100059 | 12/2003 |
| WO | WO03102214 | 12/2003 |
| WO | WO03106630 | 12/2003 |
| WO | WO03106631 | 12/2003 |
| WO | WO2004044132 | 5/2004 |
| WO | WO2004044133 | 5/2004 |
| WO | WO2004046320 | 6/2004 |
| WO | WO2004065579 | 8/2004 |
| WO | WO2004090105 | 10/2004 |
| WO | WO2004099387 | 11/2004 |
| WO | WO2005035004 | 4/2005 |
| WO | WO2006078414 | 7/2006 |

OTHER PUBLICATIONS

Ambion, "High sensitivity qRT-PCR-MesssageSensor™ reverse transcription kit for one step qRT-PCR", TechNotes, vol. 10, No. 1, 2003, 1-19.
Ambion, "Products for RNA structure/function analysis", TechNotes, vol. 8, No. 5, Nov. 2001, 1-3.
Ambion, "RNA Interference and Gene Silencing—an Update", www.ambion.com/hottopics/RNAi/rnai_jun2001.html, Jun. 2001.
Ambion, "RNA Interface in Mammalian Cell Culture Design, Execution and Analysis of the siRNA Effect", TechNotes, vol. 9, No. 1, Feb. 2002, 1-6.
Ambion, "Silencer™ siRNA Construction Kit—Protocol—Large Scale Synthesis and Purification of siRNAs, " Catalog #1620, Sep. 2002.
Ambion, "Silencer™ siRNA Labeling Kit—Instruction Manual, " Catalog 1632, 1634, Jun. 2002.
Ambion, "The Best Controls for siRNA Experiments—Now Available with More Choices", TechNotes, vol. 12, No. 1, 2003, 22-25.
Atschul et al., "Basic Local Alignment search tool", Journal of Molecular Biology, vol. 215, 1990, 403-410.
Baglioni et al., "Mechanisms of antiviral action of infection", Interferon, vol. 5, 1983, 23-42.
Baulcombe, "Fast Forward Genetics Based on Virus-Induced Gene Silencing", Current Opinion in Plant Biology, vol. 2, No. 2, Apr. 1999, 109-113.
Baulcombe, "Unwinding RNA Silencing", Science, vol. 290, No. 5494, Nov. 10, 2000, 1108-1109.
Bergstrom et al, "Comparison of the base pairing properties of a series of nitroazole nucleobase analogs in the oligodeoxyribonucleotide sequence 5'-d (CGCXAATTYGCG)-3'", Nucleic Acids Research, vol. 25, No. 10, 1997, 1935-1942.
Bernstein et al., "Role for a bidentate ribonuclease in the initiation step of RNA interference, " Nature, vol. 409, Supp. 1-8, 2001, 363-366.
Black et al, "Studies on the toxicity and antiviral of various polynucleotides", Antimicrob., Agents Chemotherap, vol. 3, No. 2, 1972, 198-206.
Blaszczyk et al., "Crystallographic and modeling studies of RNase III suggest a mechanism for double-stranded RNA cleavage", Structure, vol. 9, No. 12, 2001, 1225-1236.
Bosher et al. "RNA interference genetic wand and genetic watchdog", Nat. Cell. Biol., vol. 2, 2000, E31-E36.
Brown et al., RNA interference in mammalian cell culture: Design, Execution and Analysis of the sirRNA effect, Ambion TechNotes, vol. 9, No. 1, Feb. 2002, 1-6.
Brummelkamp et al., "A system for stable expression of short interfering RNAs in mammalian cells", Science, vol. 296, No. 5567, 2002, 550-553.
Bull et al., "Viral escape from antisense RNA", Molecular Microbiology, vol. 28, No. 4, 1998, 835-846.
Byrom et al. "Inducing RNAi with siRNA cocktails generated by RNAse III", AmbionTechNotes, vol. 10, No. 1, 2003, 4-6.
Caplen et al., "Specific inhibition of gene expression by small double-stranded RNAs in invertebrate and vertebrate systems", Proceedings of the National Academy of Sciences, vol. 98, No. 17, 2001, 9742-9747.
Catalanotto et al., "Transcription gene silencing in worms and fungi", Nature, vol. 404, No. 6775, 2000, 245.
Chiu et al., "RNAi in Human Cells : Basic Structural and Functional Features of Small Interfering RNA", Molecular Cell, vol. 10, Sep. 2002, 549-561.
Chiu et al., "siRNA Function in RNAi : A Chemical Modification Analysis", RNA, vol. 9, 2003, 1034-1048.
Cogoni et al, "Gene silencing in Neurospora crassa requires a protein homologous to RNA-dependent RNA polymerase", Nature, vol. 399, 1999, 166-169.
Cogoni et al., "Posttranscriptional gene silencing in Nuerospora by a RecQ DNA helicase", Science, vol. 286, 1999, 2342-2344.
Cormack et al., "Cloning of PCR products using the green fluorescent protein", United States National Library of Medicine, Accession No. AF007834, 1997.
Cummings et al, "Characterization of fully-2'-Modified Oligoribonucleotide Hetero-and Homoduplex Hybridization and Nuclease Sensitivity, " Nucleic Acids Research, vol. 23, No. 11, 1995, 2019-2024.
Czauderna et al., "Structural Variations and Stabilising Modifications of Synthetic siRNAs in Mammalian Cells", Nucleic Acids Research, vol. 3, No. 11, 2003, 2705-2716.
Dalmay et al., "An RNA-dependent RNA polymerase gene in Arabidopsis is required for posttranscriptional gene silencing mediated by transgene but not by a virus", Cell, vol. 101, 2000, 543-553.
Dalmay et al., "SDE3 encodes an RNA helicase required for posttranscriptional gene silencing in Arabiodopsis", Embo Journal, vol. 20, No. 8, 2001, 2069-2078.
Devereux et al., "A comprehensive set of sequence analysis programs for the VAC", Nucleic Acids Research, vol. 21, No. 1, 1984, 387-395.
Dewanjee et al., "Kinetics of Hybridization of mRNA of c-myc Oncogene with 111 in Labeled Antisense Oligodeoxynucleotide Probes by High-Pressure Liquid Chromatography", Biotechniques, vol. 16, No. 5, 1994, 844-850.
Dharmacon Research, "SiRNA Oligonucleotides for RNAi Applications : Dharmaco siACE-RNAi Options", Technical Bulletin, vol. 3, www.dharmacon.com/tech/tech2003.html, Jul. 2001.

(56) References Cited

OTHER PUBLICATIONS

Dharmacon Research, "SiRNA Oligonucleotides for RNAi Applications : Dharmaco siACE-RNAi Options", *Technical Bulletin*, vol. 3, www.dharmacon.com/tech/tech2003.html, Aug. 2001, Revision A.

Dias et al., "Antisense Oligonucleotides : Basic Concepts and Mechanisms", *Molecular Cancer Therapeutics*, vol. 1, Mar. 2002, 347-355.

Diaz et al., "Hierarchy of base-pair preference in the binding domain of the bacteriophage 17 promoter", *Journal of Molecular Biology*, vol. 229, 1993, 805-811.

Dolnick, "Naturally Occurring Antisense RNA", *Pharmacology and Therapeutics*, vol. 75, No. 3, 1997, 179-184.

Donze et al., "RNA interference in mammalian cells using siRNAs synthesized with T7 RNA polymerase", *Nucleic Acids Research*, vol. 30, No. 10, 2002, e46 (1-4 pages).

Downward, "RNA Interference", *BMJ*, vol. 328, May 22, 2004, 1245-1248.

Dubins et al., "On stability of double stranded nucleic acids", *J. Am. Chem. Soc.*, vol. 123, 2001, 9254-9259.

Elbashir et al., "Analysis of gene function in somatic mammalian cells using small interfering RNAs", *Methods*, vol. 26, 2002, 199-213.

Elbashir et al., Duplexes of 21-nucleotide RNAs mediate RNA interference in cultured mammalian cells, *Nature*, vol. 411, May 26, 2001, 494-498.

Elbashir et al., "Functional anatomy of siRNAs for mediating efficient RNA in *Drosophila melanogater* embryo lystate, " *The Embo Journal*, vol. 20, No. 23, 2001, 6877-6888.

Elbashir et al., "RNA interference is mediated by 21-and 22-nucleotide RNAs", *Genes and Development*, vol. 15, 2001, 188-200.

EP03741956.1, Examination Report mailed Jul. 15, 2008.

EP10183959.5, Supplementary Partial European Search Report mailed Dec. 19, 2007.

EP14198861.8, Extended European Search Report mailed Jun. 26, 2015.

EP1478656; Notice of Filing of Complaint, Regional Court Dusseldorf, Life Technologies Corp/Dharmacon Inc. et al. (English and German language) filed Feb. 7, 2011.

Feature of the Week—RNA Interference, Nature, Mar. 16, 2000.

Fire et al., "Potent and specific genetic interference by double-stranded RNA in Caenorhabditis elegans", *Nature*, vol. 391, 1998, 806-811.

Fire et al., "Production of antisense RNA leads to effective and specific inhibition of gene expression in C. elegans muscle", *Development*, vol. 113, No. 2, Oct. 1991, 503-514.

Ford et al., "RNAi and Microarrays Reveal Biological Pathways: The combination of RNAi with microarrays has enormous potential for elucidating biological pathways. However, before this potential can be fulfilled, important questions need to be answered to ensure the proper interpretation of gene silencing results", *R&D Magazine*, Jul. 1, 2003, 48 (3 pages).

Froehler et al., "Synthesis of DNA via deoxynucleoside H-phosphonate intermediates", *Nucleic Acids Research*, vol. 14, No. 13, 1986, 5399-5407.

Fuerst et al., "Use of hybrid vaccinia virus-T7 RNA polymerase system for expression of targeted genes", *Molecular and Cellular Biology*, vol. 7, No. 7, 1987, 2538-2544.

Glen Research, 1995, vol. 8, No. 2, 1-8.

Grishok et al., "Genes and mechanisms related to RNA interference regulate expression of the small temporal RNAs that control C. elegans developmental timing", *Cell*, vol. 106, 2001, 23-24.

Grishok et al., "Genetic Requirements for Inheritance of RNAi in C. elegans", *Science*, vol. 287, Mar. 31, 2000, 2494-2497.

Grünweller et al., "Comparison of Different Antisense Strategies in Mammalian Cells Using Locked Nucleic Acids, 2'-O-methyl RNA, Phosphorothioates and small interfering RNA", *Nucleic Acids Research*, vol. 31, No. 12, 2003, 3185-3193.

Hamilton et al., "A Species of Small Antisense RNA in Post-transcriptional Gene Silencing in Plants", *Science*, vol. 286, No. 5441, Oct. 29, 1999, 950-952.

Hammond et al., "An RNA-directed nuclease mediates post-transcriptional gene silencing in *Drosophila* cells", *Nature*, vol. 404, No. 6775, 2000, 293-296.

Hammond et al., "Argonaute 2, a link between genetic and biochemical analyses of RNAi", *Science*, vol. 293, 2001, 1146-1150.

Hammond et al., "Post-transcriptional gene silencing by double-stranded RNA", *Nat. Rev. Genet.*, vol. 2, No. 2, 2001, 110-119.

Hammond, RNAi Technologies in *Drosophila* Cell Culture, *RNAi—A Guide to Gene Silencing (Cold Spring Harbor Laboratory Press, Hannon Ed.)*, Chapter 16, 2003, 345-360.

Han et al., "Sequence-specific recognition of double helical RNA and RNA-DNA by triple helix formation", *Proceedings of the National Academy of Sciences*, vol. 90, 1993, 3806-3810.

Hannon et al., "Unlocking the Potential of the Human Genome with RNA interface", *Nature*, vol. 431, 2004, 371-378.

Harborth et al., "Identification of essential genes in cultured mammalian cells using small interfering RNAs", *Journal of Cell Science*, vol. 114, No. 24, Dec. 2001, 4557-4565.

Hebert et al., "Purification of ribonucleases Sa, Sa2, and Sa3 after expression in *Escherichia coli*", *Protein Expr. Purif.*, vol. 11, No. 2, 1997, 162-168.

Higgins et al., "Clustal V: improved software for multiple sequence alignment", *Computer Applications in the Biosciences (CABIOS)*, vol. 8, No. 2, 1992, 189-191.

Hill et al., "Fluorescence Approaches to Study of Protein-Nucleic Acid Complexation", Methods in Enzymology, vol. 278, 1997, 390-416.

Holen et al., "Positional Effects of Short Interfering RNAs targeting the Human Coagulation Trigger Tissue Factor", *Nucleic Acids Research*, vol. 30, No. 8, 2002, 1757-1766.

Holen et al, "Similar behaviour of single-strand and double-strand siRNAs suggest they act through a common RNAi pathway", *Nucleic Acids Research*, vol. 31, No. 9, 2003, 2401-2407.

Hough et al., "Why RNAi Makes Sense", *Nature Biotechnology*, vol. 21, No. 7, Jul. 2003, 731-732.

Hutvagner et al., "A cellular function for the RNA-interference enzyme Dicer in the maturation of the let-7 small temporal RNA", *Science*, vol. 293, 2001, 834-838.

Invitrogen, "Life Technologies Inc. Catalogue and Reference Guide—Lipofectamine Reagent, Lipofectin Reagent", GIBCO BRL, 1993-1994, 9-19.

Invitrogen, "Oligofect AMINE Reagent product information", Catalog 122552-01, Life Reagent, Aug. 23, 2001.

Iyer et al., "3H-1,2-benzodithiole 3-one1,1-dioxide as an improved sulfurizing reagent in the solid-phase synthesis of oligodeoxyribonucleoside phosphorothioates", *J. Am. Chem. Soc.*, vol. 112, 1990, 1253-1254.

Jackson et al., "Expression Profiling Reveals Off-Target Gene Regulation by RNAi", *Nature Biotechnology*, vol. 21, No. 6, 2003, 635-638.

Jacque et al., "Modulation of HIV-1 replication by RNA interference", *Nature*, vol. 418, 2002, 435-438.

Jones et al., "RNA-DNA Interactions and DNA Methylation in Post-Trasncriptional Gene Silencing", *The Plant Cell*, vol. 11, No. 12, Dec. 1999, 2291-2301.

Jorgensen et al., "An RNA-Based Information Superhighway in Plants", *Science*, vol. 279, No. 5356, Mar. 6, 1998, 1486-1487.

Kawase et al., "Studies on nucleic acid interactions I, Stabilities of mini-duplexes (dG2A4XA4G2-dC2T4YT4C2) and self-complementary d(GGAAXYTTCCC) containing deoxyinosine and other mismatched bases", *Nucleic Acids Research*, vol. 14, No. 19, 1986, 7727-7736.

Kennerdell et al., "Heritable Gene Silencing in *Drosophila* using Double-Stranded RNA", *Nature Biotechnology*, vol. 172000, 896-898.

Ketting et al., "A genetic link between co-suppression and RNA interference in C. elegans", *Nature*, vol. 404, vol. 6775, 2000, 296-298.

(56) References Cited

OTHER PUBLICATIONS

Ketting et al., "Dicer Functions in RNA Interference and in Synthesis of Small RNA Involved in Developmental Timing in C. Elegans", *Genes Dev.*, vol. 15, 2001, 2654-2659.
Ketting et al., "mut-7 of C. elegans, required for transposon silencing and RNA interference, is a homolog of Werner syndrome helicase and RNaseD", *Cell*, vol. 99, 1999, 133-141.
Kharrat et al., "Structure of the dsRNA bidning domain of E. coli RNase III", *The EMBO Journal*, vol. 14, No. 14, 1995, 3572-3584.
Kievits et al., "NASBA™ isothermal enzymatic in vitro nucleic acid amplification optimized for the diagnosis of HIV-1 infection", *Journal of Virological Methods*, vol. 35, 1991, 273-286.
Kimura et al., "Alterations of c-myc expression by antisense oligodeoxyncleotides enhance the induction of apoptosis of HL-60 cells", *Cancer Research*, vol. 55, 1995, 1379-1384.
Kita et al., "Modulation of polyglutamine-induced cell death by genes identified by expression profiling", *Human Molecular Genetics*, vol. 11, No. 19, 2002, 2279-2287.
Knight et al., "A Role for the RNase III Enzyme DCR-1 in RNA Interference and Germ Line Development in C. elegans", *Science*, vol. 293, No. 5538, 2001, 2269-2271.
Kuhnast et al, "General method to label antisense oligonucleotides with radioactive haloens for pharmacological and imaging studies", *Bioconjug. Chem.*, vol. 11, No. 5, 2000, 627-636.
Kurreck, "Antisense Technologies: Improvement Through Novel Chemical Modifications", *Eur. J. Biochem.*, vol. 270, 2003, 1628-1644.
Kuwasaki et al., "Hairpin Antisense Oligonucleotides Containing 2'-Methxynucleotides with Base-Pairing in the Stem Region at the 3'-end Penetration, Localization, and Anti-HIV Activity", *Biochemical Biophysical Res. Comm.*, vol. 228, 1996, 623-631.
Kuznicki et al., "Combitional RNA Interference Indicates GLH-4 Can Compensate for GLH-1; these two P Granule Components are Critical for Fertility in C. elegans", *Development*, vol. 127, 2000, 2907-2916.
Kwoh et al., "Transcription-based amplification system and detection of amplified human immunodeficiency virus type 1 with a bead-based sandwich hybridization format", *Proceedings of the National Academy of Sciences*, vol. 86, 1989, 1173-1177.
Latham et al., "Six Methods of Inducing RNAi in Mammalian Cells", *RNA Interference Technology*, 2005, 147-160.
Lavigne et al., "Lipid-Based Delivery of Combinations of Antisense Oligodeoxynucleotides for the Invitro Inhibition of HIV-1 Replication", *AAPS Pharmsci.*, vol. 3, No. 1, 2001, 1-12.
Lee et al., "Expression of small interfering RNAs targeted against HIV-1 rev transcripts in human cells", *Nat. Biotechnology*, vol. 19, 2002, 500-505.
Lee et al., "Tissue-specific promoter usage in the $D_{1A}$ dopamine receptor gene in brain and kidney", *DNA and Cell Biol.*, vol. 16, No. 11, 1997, 1267-1275.
Lesk, ed., "Computational Molecular", Oxford University Press, New York, 1988.
Li et al., "Double-stranded RNA injection produces null phenotypes in Zebrafish", *Developmental Biology*, vol. 217, 2000, 394-405.
Lin et al., "Policing rogue genes",*Nature*, vol. 402, 2000, 128-129.
Liu et al., "A scintillation proximity assay for RNA detection", *Anal. Biochem.*, vol. 289, 2001, 239-245.
Liu et al., "Delivering siRNA in vivo for Functional Genomics and Novel Therapeutics", *RNA Inteference Technology*, 2005, 303-317.
Lorenz et al., "Phosphorotiaote Antisense Oligonucleotides Induce the Formation of Nuclear Bodies", *Molecular Biology of the Cell*, vol. 9, May 1998, 1007-1023.
Lu et al., "Delivering siRNA in vivo for Functional Genomics and Novel Therapeutics", *RNA Interference Technology*, 2005, 303-317.
Makeyev et al., "Replicase activity of purified recombinant protein P2 and double-stranded RNA bacteriophage phi6", *EMBO J.*, vol. 19, No. 1, 2001, 124-133.
Manche et al., "Interactions between Double-Stranded RNA Regulations and the Protein Kinase DAI", *Molecular and Cellular Biology*, vol. 12, 1992, 5238-5248.

Martinez et al., "Single-stranded antisense siRNAs guide target RNA cleavage in RNAi", *Cell*, vol. 110, No. 5, 2002, 563-574.
Max Planck Institute for Biophysical Chemistry, "The siRNA user guide", www.mpibpc.gwdg.de/abteilungen/100/105/siRNAuserguide.pdf, Revised Aug. 26, 2001.
McCaffrey et al., "RNA Interference in Adult Mice", *Nature*, vol. 418, Jul. 4, 2002, 38-39.
McManus et al., "Gene silencing in mammals by small interfering RNAs", *Nature Reviews, Genetics*, vol. 3, 2002, 737-747.
Meister et al., "Mechanisms of Gene Silencing by Double-Stranded RNA", *Nature*, vol. 431, 2004, 343-349.
Milligan et al., Oligonucleotide synthesis using T7 RNA polymerase and synthetic DNA templates, *Nucleic Acids Research*, vol. 15, Nov. 21, 1987, 8783-8798.
Milligan et al., "Current Concepts in Antisense Drug Design", Journal of Medicinal Chemistry, vol. 36, No. 14, 1993, 1923-1937.
Miyagishi et al., "U6 promoter-driven siRNAs with four uridine 3' overhangs efficiently suppress targeted gene expression in mammalian cells", *Nat. Biotechnol.*, vol. 5, 2002, 497-500.
Montgomery et al., "Double-Stranded RNA as a mediator in sequence-specific genetic silencing and co-suppression", *Trends in Genetics*, vol. 14, No. 7, Jul. 1998, 255-258.
Montgomery et al., "RNA as a target of double-stranded RNA-mediated genetic interference in Caenorhabditis elegans", *Proceedings of the National Academy of Sciences*, vol. 95, 1998, 15502-15507.
Moon et al., "Potent Growth Inhibition of Leukemic Cells by Novel Ribbon-type Antisense Oligonucleotides of c-mybl", *Journal of Biological Chemistry*, vol. 275, No. 7, 2000, 4647-4653.
Morgan et al, "A More Efficient and Specific Strategy in the Ablation of mRNA in Xenopus laevis Mixtures of Antisense Oligos", *Nucleic Acids Research*, vol. 21, No. 19, 1993, 4615-4620.
Mourrain et al, "Arabidopsis SGS2 and SGS3 genes are required for posttranscriptonal gene silencing and natural virus resistance", *Cell*, vol. 101, 2000, 533-542.
Myers et al., "Recombinant Dicer efficiently converts large dsRNAs into siRNAs suitable for gene silencing", *Nature Biotechnology*, vol. 21, 2003, 324-328.
Ngo et al., "Double-stranded RNA includes mRNA degradation in Trypanosoma brucei", *Proceedings of the National Academy of Sciences*, vol. 95, 1998, 14687-14692.
Nguyen et al., "Modification of DNA duplexes to smooth their thermal stability independently of their base content for DNA sequencing by hybridization", *Nucleic Acids Research*, vol. 25, No. 15, 1997, 3059-3065.
Novina et al., "siRNA-directed inhibition of HIV-1 infection", *Nat. Med.*, vol. 8, 2002, 681-686.
Nykanen et al., "ATP requirements and small interfering RNA structure in the RNA interference pathway", *Cell*, vol. 107, No. 3, 2001, 309-321.
Oates et al., "Too Much Interference Injection of Double-Stranded RNA has Nonspecific Effects in the Zebrafish Embryo", *Developmental Biology*, vol. 224, 2000, 20-28.
Pace et al., "Conformational stability and thermodynamics of folding of ribonucleases Sa, Sa2, Sa3", *J. Mol. Biol.*, vol. 279, 1998, 271-286.
Paddison et al., "Short hairpin RNAs (shRNAs) induced sequence-specific silencing in mammalian cells", *Genes & Development*, vol. 16, 2002, 948-958.
Paddison et al., "Stable Suppression of Gene Expression by RNAI in Mammalian Cells", *Proceedings of the National Academy of Sciences*, vol. 99, No. 3, 2002, 1443-1448.
Paroo et al., "Challenges for RNAi in vivo", *Trends in Biotechnology*, vol. 22, No. 8, Aug. 2004, 390-394.
Parrish et al., "Functional anatomy of a dsRNA trigger : Differential requirement for the two trigger strands in RNA interference", *Molecular Cell*, vol. 6, Nov. 2000, 1077-1087.
Paul et al., "Effective expression of small interfering RNA in human cells", *Nat. Biotechnol.*, vol. 20, 2002, 505-508.
PCT/US2003/018626, International Search Report mailed Feb. 11, 2004.
PCT/US2003/018626, Written Opinion mailed Sep. 23, 2004.

(56) References Cited

OTHER PUBLICATIONS

PCT/US2003/018627, International Search Report mailed Mar. 16, 2004.
PCT/US2003/018627, Written Opinion mailed Oct. 1, 2004.
PCT/US2003/064621; International Search Report mailed Jul. 18, 2005 (Our File 6532PCT).
PCT/US2003/003023, International Search Report mailed Jul. 18, 2005.
PCT/US2003/003223, International Preliminary Report on Patentability mailed Aug. 4, 2004.
PCT/US2003/036401, International Search Report mailed May 28, 2004.
PCT/US2005/046779, International Search Report and Written Opinion mailed Nov. 30, 2006.
Perkel, "Off-Target Effects Plague *Drosphila* RNAi", *The Scientist*, 2006, 1-5.
Plasterk et al., "The silence of the genes", *Curr. Opin. Genet. Dev.*, vol. 10, 2000, 562-567.
Rakoczy et al., "Targeted Delivery of an Antisense Oligonucleotide in the Retina : Uptake, Disruption, Stability, and effect", *Antisense Nucleic Acid Drug Dev.*, vol. 6, No. 3, 1996, 207-213.
Ramos et al., "RNA recognition by a Staufen double-stranded RNA-binding domain", *EMBO Journal*, vol. 19, No. 5, 2000, 997-1009.
Ratcliff et al., "A Similarity Between Viral Defense and Gene Silencing in Plants", *Science*, vol. 276, No. 5318, Jun. 6, 1997, 1558-1560.
Ratcliff et al., "Gene Silencing with DNA: RNA-Mediated Cross-Protection between Viruses", *The Plant Cell*, vol. 11, No. 7, Jul. 1999, 1207-1215.
Regnier et al., "Localization of a FITC-labeled phosphorothioate oligodeoxynucleotide in the skin after topical delivery by iontophoresis and electroporation", *Phar. Res.*, vol. 15, No. 10, 1998, 1596-1602.
Reynolds et al., "Rational siRNA Design for RNA Interference", *Nature Biotechnology*, vol. 22, No. 3, Mar. 2004, 326-330.
Rusckowski et al., "Biodistribution and metabolism of a mixed back-bone oligonucleotide (GEM 231) following single and multiple dose administration in mice", *Antisense Nucleic Acid Drug Dev.*, vol. 5, 2000, 333-345.
Ruvkun et al., "Glimpses of a Tiny RNA World", *Science*, vol. 294, 2001, 797-799.
Ryan et al., "Myc oncogenes : the enigmatic family", *Biochem. J.*, vol. 314, 1996, 713-721.
Ryter et al., "Molecular basis of double-stranded RNA-protein interactions : structure of a dsRNA-binding domain complexed with dsRNA", *EMBO J.*, vol. 17, 1998, 7505-7513.
Sambrook et al., Molecular Cloning, Cold Spring Harbor Laboratory Press, 2001.
Samarsky et al., "RNAi in Drug Development : Practical Considerations", *RNA Interferene Technology*, 2005, 384-395.
Scalon, "Anti-Genes: siRNA, Ribozymes and Antisense", *Current Pharmaceutical Biotechnology*, vol. 5, 2004, 415-420.
Schlingensiepen et al., "The Role of Jun Transcription Factor Expression and Phosphorylation in Neuronal Differentiation, Neuronal Cell Death and Plastic Adaptations in Vivo", *Cell Mol. Neurobiol.*, vol. 14, 1994, 487-505—see 12568244 OA 20110126.
Schmid et al., "Combinatorial RNAi : A Method for Evaluating the Function of Gene Families in *Drosophila*", *Trends in Neurosciences*, vol. 25, No. 2, Feb. 2002.
Sedelnikova et al., "Targeting the human mdrl gene by 125I-labeled triplex-forming oligonucleotides", *Antisense Nucleic Acid Drug Dev.*, vol. 10, 2000, 443-452.
Sharp, "RNAi and double-strand RNA", *Genes Dev.*, vol. 13, 1999, 139-141.
Sharp, "RNA Interference-2001", *Genes & Dev.*, vol. 15, 2001, 485-490.
Shishkina et al., "A new method for the postsynthetic generation of a abasic sites in oligometric DNA", *Chem. Res. Toxicol.*, vol. 13, 2000, 907-912.
Skripkin et al., "Mechanisms of Inhibition of in Vitro Dimerization of HIV Type I RNA by Sense and Antisense Oligonucleotides", *The Journal of Biological Chemistry*, vol. 271, Nov. 15, 1996, 28812-28817.
Singh et al., "Real Time Kinetics of Ribozyme Reactions," *Ribozyme Biochemistry and Biotechnology*, A17-A20, 351-371, 2000.
Smardon et al., "EGO-1 is related to RNA-directed RNAp polymerase and functions in germ-line development and RNA interference in C. elegans", *Curr. Biol.*, vol. 10, 2000, 169-178.
Smith, ed., *Biocomputing: Informatics and Genome Projects*, Academic Press, New York 1993.
St. Johnston et al., "A conserved double-stranded RNA-binding domain", *Proceedings of the National Academy of Sciences*, vol. 89, 1992, 10979-10983.
Stalnacke et al., "Radiotoxicity of 11C-methionnine measured by the accumulation of DNA strand breaks in mammalian cells", *Eur. J. Nucl. Med.*, vol. 11, 1985, 166-170.
Stein, "The experimental use of antisense oligonucleotides : a guide for the perplexed", *J. Clinical Invest.*, vol. 108, No. 5, 2001, 641-644.
Sui et al., "A DNA vector-based RNAi technology to suppress gene expression in mammalian cells", *Proceedings of the National Academy of Sciences*, vol. 99, No. 8, 2002, 5515-5520.
Svoboda et al., RNAi Oocytes and Preimplantation Embryos: Effectiveness of Hairpin dsRNA, *Biochemical and Biophysical Research Communications*,, vol. 287, 2001, 1099-1104.
Tabara et al., "The rde-1 gene, RNA interference, and transposon silencing in C. elegans", *Cell*, vol. 99, 1999, 123-132.
Tavernarakis et al. "Heritable and Inducible Genetic Interference by Double-Stranded RNA encoded by Transgenes", *Nature Genetics*, vol. 24, 2000, 180-183.
Testa et al., "Thermodynamics of RNA-RNA Duplexes with 2- or 4-thiouridines", *Biochemistry*, vol. 38, 1999, 16655-16662.
Thompson et al., "Clustal W : improving the sensitivity of progressive multiple sequence alignment through sequence weighting, position-specific gap penalties and weigh matrix choice", *Nucleic Acids Res.*, vol. 22, 1994, 4673-4680.
Timmons et al., "Specific Interference by Ingested dsRNA.", *Nature*, vol. 395, No. 6705, Oct. 29, 1998, 854.
Trotta et al., "BCR ABI. Activates mdm2 Mrna translation via the La antigen", *Cancer Cell*, vol. 3, 2003, 145-160.
Tuschl, "RNA interference and small interfering RNAs", *Chembiochem*, vol. 2, 2001, 239-245.
Tuschl et al., "Targeted mRNA degradation by double-stranded RNA in vitro", *Genes & Development*, vol. 13, 1999, 3191-3197.
Tuschl et al., "Small Interfering RNAs : A Revolutionary Tool for the Analysis of Gene Function and Gene Therapy", *Molecular Interventions*, vol. 2, No. 3, Jun. 2002, 158-167.
Vickers et al., "Efficient Reduction of Target RNAs by Small Interferring RNA and RNase H-dependant Antisense Agents", *The Journal of Biological Chemistry*, vol. 278, 2003, 7108-7118.
Voinnet et al., "Systemic Spread of Sequence-Specific Transgene RNA Degradation in Plants Is Initiated by Localized Introduction of Ectopic Promoterless DNA", *Cell*, vol. 95, No. 2, Oct. 16, 1998, 177-187.
Vyas et al., "Ligand-receptor-mediated drug delivery :an emerging paradigm in cellular drug targeting", *Crit. Rev. Ther. Drug Carrier Syst.*, vol. 18, No. 1, 2001, 1-76.
Wagner et al., "Double-stranded RNA poses puzzle", *Nature*, vol. 391, No. 6669, Feb. 19, 1998, 744-745.
Waterhouse et al., "Gene silencing as an adaptive defense against viruses", *Nature*, vol. 411, 2001, 834-842.
Waterhouse et al., "Virus resistance and gene silencing in plants can be induced by simultaneous expression of sense and antisense RNA", *Proceedings of the National Academy of Sciences*, vol. 95, No. 23, Nov. 1998, 13959-13964.
Waterhouse et al., "Virus resistance and gene silencing: killing the messenger", *Trends in Plant Science*, vol. 4, No. 11, Nov. 1999, 452-457.
Williams, "Gene expression domains as markers in developmental toxicity studies using mammalian embryo culture",*Int. J. Dev. Biol.*, vol. 41, No. 2, 1997, 359-364.

(56) References Cited

OTHER PUBLICATIONS

Wilson, "DNA Triple-Helix Specific Intercalators As Antigene Enhancers : Unfused Aromatic Cations", *Biochemistry*, vol. 32, 1993, 10614-10621.
Wincott et al., "Synthesis, Deprotection, Analysis and Purification of RNA and Ribozymes", *Nucleic Acids Research*, vol. 23, 1995 2677-2684.
Wu et al., "Prevention of chain cleavage in the chemical synthesis of 2'-silylated oligonucleotides", *Nucleic Acids Research*, vol. 17, No. 9, 1989, 3501-3517.
Wu-Scharf et al., "Transgene and transposon silencing in Chlamydomonas reinhardtii by a DEAH-box RNA helicase", *Science*, vol. 290, 2000, 1159-1162.
Xia et al., "siRNA-mediated gene silencing in vitro and in vivo", *Nat. Biotechnol.*, vol. 20, No. 10, 2002, 1006-1010.
Yang et al., "Short RNA duplexes produced by hydrolysis with *Escherichia coli* RNase III, mediate effective RNA interference in mammalian cells", *Proceedings of the National Academy of Sciences*, vol. 99, No. 15, 2002, 9942-9947.
Yoo, "Enhanced delivery of antisense oligonucleotides with fluorophore-conjugated PAMAM dendrimers", *Nucleic Acids Research*, vol. 28, 2000, 4225-4231.
Yu et al., "RNA interference by expression of short-interfering RNAs and hairpin RNAs in mammalian cells", *Proceedings of the National Academy of Sciences*, vol. 99, 2002, 6047-6052.
Zamore et al., "ATP Requirements and Small Interfering RNA Structure in the RNA Interference Pathway", *Cell*, vol. 107, Nov. 2, 2001, 309-321.
Zamore et al., "RNA interference : listening to the sound of silence", *Nat. Struct. Biol.*, vol. 8, 2001, 746-750.
Zamore et al., "RNAi : double-stranded RNA directs the ATP-dependent cleavage of mRNA at 21 to 23 nucleotide intervals", *Cell*, vol. 101, 2000, 25-33.
Zhang et al., "Influence of different chelators (HYNIC, MAG3 and DTPA) on tumor cell accumulation and mouse biodistribution of technetium-99m labeled to antisense DNA", *Eur. J. Nucl., Med.*, vol. 27, No. 11, 2000, 1700-1707.
Zhang et al., "In vitro investigationk of tumor targeting with 99m Tc-labeled antisense DNA", *J. Nucl. Med.*, vol. 42, No. 11, 2001, 1660-1669.
Zhang et al., "Uptake and distribution of fluorescein-labeled D2 dopaminereceptor antisense oligdeoxynucleotide in mouse brain", *J. Mol. Neurosci.*, vol. 7, 1996, 13-28.
Zhao et al., "Double-stranded RNA Injection Produces Nonspecific Defects in Zebrafish", *Developmental Biology*, vol. 229, 2001, 215-223.
Akashi, M. et al., "Number and location of AUUUA motifs: role in regulating transiently expressed RNAs," Blood, vol. 83, No. 11, 1994, 3182-3187.
Akhtar, S., et. al., The Delivery of Antisense Therapeutics, Advanced Drug Delivery Reviews, 2000, pp. 3-21.
Alahari, S. K. et al., "Inhibition of Expression of the Multidrug Resistance-Associated P-Glycoprotein of by Phosphorothioate and 5' Cholesterol-Conjugated Phosphorothioate Antisense Oligonucleotides," Mol. Pharmacol., 50(4):808-819, 1996.
Allerson, C. et al., "Fully 2'-Modified Oligonucleotide Duplexes with Improved in Vitro Potency and Stability Compared to Unmodified Small Interfering RNA," J. Med. Chem., 48, 2005, 901-904.
Allinquant, B. et al., "Downregulation of Amyloid Precursor Protein Inhibits Neurite Outgrowth in Vitro," The Journal of Cell Biology, vol. 128, No. 5, 1995, pp. 919-927.
Altmann, K H. et al., "Novel Chemistry," Applied Antisense Oligonucleotide Technology, 1998, 73-107.
Altschul, S. et al., "Basic local alignment search tool," J. Mol. Biol., vol. 215, 1990, 403-410.
Altschul, S. et al., "Gapped BLAST and PSI-BLAST: a new generation of protein database search," Nucleic Acids Research, vol. 25, 1997, 3389-3402.

Amann et al., "Modern Methods in Subsurface Microbiology: In Situ Identification of Microorganisms with Nucleic Acid Probes," FEMS Microbiology Review, vol. 20, Issue 3-4, Jul. 1997, 191-200.
Amarasinghe et al., "*Escherichia coli* ribonuclease III: Affinity purification of hexahistidine-tagged enzyme and assays for substrate binding and cleavage," Methods in Enzymology, vol. 342, 2001, 143-158.
Ambion, Inc., "pSilencer siRNA Expression Vector, " Ambion TechNotes, a newsletter from 9(4), 2002.
Ambion, Inc., siRNA target finder for GenBank Accession No. AF007834, Ambion siRNA Target Finder, Austin, TX, Ambion, Jun. 2002: [retrieved on Oct. 18, 2007]. Retrieved from the internet: http://www.ambion.com/.
Amersham Pharmachia Biotech, Kits for Labeling DNA, BioDirectory '98, p. 136, 1998.
Anderson et al., "Human Gene Therapy," Nature, vol. 392, Supplement, Apr. 30, 1998, 25-30.
Aoki, Y. et al., "RNA Interference May be more Potent Than Antisense RNA in Human Cancer Cell Lines," Clinical and Experimental Pharmacology Physiology, vol. 30, 2003, pp. 96-102.
Ashley et al., "Chemical Synthesis of Oligodeoxynucleotide Dumbbells," Biochemistry, 30, 1991, 2927-2933.
ATTC, Catalogue of Cell Lines & Hybridomas, 7th Edition, 1992, 15 pages.
AU 2003208962; Examiner's Report mailed Jul. 25, 2007.
Augustyns, K. et al., "Incorporation of Hexose Nucleoside Analogues into Oligonucleotides: Synthesis, Base-Pairing Properties of Enzymatic Stability," Nucleic Acids Research, vol. 20, No. 18, 1992, 4711-4716.
Aurup, H. et al., "Translational of 2'-Modified mRNA in vitro and in vivo," Nucleic Acids Research, vol. 22, No. 23, 1994, pp. 4963-4968.
Ausubel et al., "Introduction to Expression by Fusion Protein Vectors," Current Protocols in Molecular Biology, 1994, 16.4.1-16. 4.4.
Ausubel et al., "Short Protocols in Molecular Biology," A Compendium of Methods from Current Protocols in Molecular Biology, 2002, 359.
Ausubel et al., Current Protocols in Molecular Biology, Supplement 63, (Table of Contents), 1998.
Averbuch, et al. "Dynamic Adaptive Layer 2 Time Adjustment", Motorola Technology Dev., vol. 30, 1997, pp. 21-22.
Bartzatt, R., "Cotransfection of Nucleic Acids Segments by Sendai Virus Envelopes," Biotechnology and Applied Biochemistry, vol. 11, 1989, 133-135.
Bass, B., "Double-Stranded RNA as a Template for Gene Silencing," Cell, vol. 101, 2000, 235-238.
Beaucage et al. "Advances in the Synthesis of Oligonucleotides by the Phosphoramidite Approach," Tetrahedron, 48:2223-2311, 1992.
Bennett et al., "Antisense oligonucleotides as a tool for gene functionalization and target validation," Biochimica et Biophysica Acta, vol. 1489: 19-30; 1999.
Bennett, C. F. et al., "Cationic lipids enhance cellular uptake and activity of phosphorothioate antisense oligonucleotides," Molecular Pharmacology, vol. 41, 1992, 1023-1033.
Bergan et al., "Electroporation enhances c-myc antisense oligodeoxynucleotide efficacy," Nucleic Acids Research, 21, 1993, 3567-3573.
Bergot, J. et al., "Separation of synthetic phosphorothioate oligonucleotides from their oxygenated (phosphodiester) defect species by strong-anion-exchange high-performance liquid chromatography.," J Chrom., 599, 1992, 35-42.
Bernstein et al., "The Rest is Silence," RNA, vol. 7, Cambridge University Press 2001, 1509-1521.
Bevilacqua et al., "Minor-Groove Recognition of Double-Stranded RNA by the Double-Stranded RNA-Binding Domain from the RNA-Activated Protein Kinase PKR," Biochemistry, vol. 35, Issue 31, Aug. 6, 1996, 9983-9994.
Bjergarde, Kristen et al., "Solid phase synthesis of oligodeoxyribonucleoside phosphorodithioates from thiophosphoramidites," Nucleic Acids Research, vol. 19, 1991, 5843-5850.

(56) References Cited

OTHER PUBLICATIONS

Blake et al, "Hybridization Arrest of Globin Synthesis in Rabbit Reticulocyte Lysates and Cells by Oligodeoxyribonucleoside Methylophosphonates," Biochemstry, vol. 24, No. 22, Oct. 1985, 6139-6145.
Bouloy et al., "Both the 7-Methyl and the 2'-O-Methyl Groups in the Cap of mRNA Strongly Influence Its Ability to Act as Primer for Influenza Virus RNA Transcription," Proceedings of the National Academy of Sciences (PNAS), vol. 77, Issue 7, Jul. 15, 1980, 3951-3956.
Boutorin et al., "Synthesis of alkylating oligonucleotide derivatives containing cholesterol or phenazinium residues at their 3'-terminus and their interaction with DNA within mammalian cells," FEBS Letters, vol. 254, 1989, 129-132.
Boutorine et al., "Reversible Covalent Attachment Of Cholesterol To Oligodeoxyribonucleotides For Studies Of The Mechanisms Of Their Penetration Into Eucaryotic Cells," Biochimie, vol. 75, 1993; 35-41.
Branch, A., "A good antisense molecule is hard to find," TIBS, vol. 23: 45-50, 1998.
Britten et al., "Nucleic Acid Hybridisation: A Practical Approach," Oxford University Press, 1985, 5-7.
Brown et al., "Sequence-Specific Endonucleolytic Cleavage and Protection of mRNA in Xenopus and *Drosophila*," Genes & Development, vol. 7, No. 8, Aug. 1993, 1620-1631.
Bunnell, B. A. et al., "Targeted Delivery of Antisense Oligonucleotides by Molecular Conjugates,"Somatic Cell and Molecular Genetics, vol. 18, No. 6, 1992, 559-569.
Caruthers, M. H. et al., "Chemical and Biochemical Studies with Dithioate DNA," Nucleosides & Nucleotides, 10(1-3), 1991, 47-59.
Chen et al, "Characterization of a Bicistronic Retroviral Vector Composed of the Swine Vesicular Disease Virus Internal Ribosome Entry Site," Journal of Virology, vol. 67, Issue 4, Apr. 1993, 2142-2148.
Chen, C. et al, "High-Efficiency Transformation of Mammalian Cells by Plasmid DNA," Mol. Cell Biol., 7(8), 1987, 2745-2752.
Chen, G. et al., "Antisense oligonucleotides demonstrate a dominant role of c-Ki-RAS proteins in regulating the proliferation of diploid human fibroblasts," The Journal of Biological Chemistry, vol. 271, No. 45, 1996, 28259-28265.
Chiang, M. Y. et al., "Antisense Oligonucleotides Inhibit Intercellular Adhesion Molecule 1 Expression by Two Distinct Mechanisms," J. Biol. Chem., vol. 266, No. 27, 1991, 18162-18171.
Chidambaram, N. et al., "Targeting of Antisense: Synthesis of Steroid-Linked and Steroid-Bridged Oligodeoxynucleotides," Drug Discovery, 3(1):237-33, 1989.
Chu et al., "The Stability of Different Forms of Double-Stranded Decoy DNA in Serum and Nuclear Extracts," Nucleic Acids Research, 20, 1992,5857-5858.
Cioca, D. P. et al., "RNA interference is a functional pathway with therapeutic potential in human myeloid leukemia cell lines," Cancer Gene Therapy, vol. 10, 2003, 125-133.
Clusel; C. et al., "Ex vivo regulation of specific gene expression by nanomolar concentration of double stranded dumbbell oligonucleotides," Nucleic Acids Research, vol. 21, No. 15, Oxford University Press 1993; pp. 3405-213.
Cook, "Medicinal Chemistry Of Antisense Oligonucleotides," Antisense Drug Technology, vol. 2, 2001; pp. 29-56.
Cottrell, T. et al., "Silence of the strands: RNA interference in eukaryotic pathogens," Trends Microbiol., vol. 11, No. 1, 2003, 37-43.
De Clercq et al. "Interferon Induction by two 2' modified bouble helical RNA ploy 2' Fluro-2'-deoxy inosinic-acid poly cytidylic-acid and poly-2' chloro-2'-deoxy inosinic-acid poly cytidylic-acid," European Journal of Biochemistry, vol. 107, No. 1: 279-288; 1980.
Dean, N. M. et al., "Identification and Characterization of Second-Generation Antisense Oligonucleotides," Antisense & Nucleic Acid Drug Development, vol. 7, 1997, 229-233.
Derossi, D. et al., "Trojan peptides: the penetratin system for intracellular delivery," Trends in Cell Biolog., 8, 1998, 84-87.
Diaz et al., "Initiation of plasmid R1 replication in vitro is independent of transcription of host RAN polymerase," Nucleic Acids Research, 12(13):5175-5191, 1984.
Didenko, V. "DNA probes using fluorescence resonance energy transfer (FRET): designs and applications," Biotechniques, 31(5):1106-1121, 2001.
Eckstein et al., "Exogenous Application of Ribozymes for Inhibiting Gene Expression," CIBA Foundation Symposium, vol. 209, 1997, 207-217.
Elliott, G. et al., "Intercellular trafficking and protein delivery by a herpesvirus structural protein," Cell, vol. 88,1997, 223-233.
Emptage et al., "Calcium Stores in Hippocampal Synaptic Boutons Mediate Short-Term Plasticity, Store-Operated Ca2+ Entry, and Spontaneous Transmitter Release" Neuron, 29(1):197-208, 2001.
EP03707687.4; Supplementary European Search Report mailed Apr. 3, 2008.
EP03708928.1; International Search Report mailed Mar. 14, 2007.
EP03708949.7; European Examination Report mailed Jun. 8, 2009.
EP03708949.7; International Search Report mailed Jan. 11, 2008.
EP03708949.7, Decision to Discontinue the Opposition Proceedings mailed Jan. 19, 2015.
EP09166406.0; Extended European Search Report mailed Oct. 28, 2009.
EP10151247.3; Extended European Search Report mailed Jul. 23, 2010.
EP10152725.7; Extended European Search Report mailed Jul. 6, 2010.
EP10152730.7; Extended European Search Report mailed Jun. 30, 2010.
EP10152730.7, Decision to Discontinue the Opposition Proceedings mailed Jan. 19, 2015.
EP10183959.5; Extended European Search Report mailed Jun. 8, 2011.
EP11169151.5; Extended European Search Report mailed Apr. 19, 2012.
EP1478656; Defendant's Observations in Response to Board's Preliminary Opinion with Attachments (New Main Request, Klimkait Opinion & CV); DE 603 29 277.1-08 (EP 1 478 656 B1) filed by Fisher Scientific GmbH, plaintiff; Life Technologies Corporation, proprietor. Sep. 27, 2012 (English Translation).
EP1478656; Defendant's Reply to Plaintiff's Complaint, Regional Court Dusseldorf, Life Technologies Corp/Dharmacon Inc. et al. Mar. 5, 2012 (English Translation).
EP1478656; Grounds for the Objection—Defendant's Response to Nullity Complaint with Attachments; DE 603 29 277.1-08 (EP 1 478 656 B1) filed by Fisher Scientific GmbH, plaintiff; Life Technologies Corporation, proprietor. Apr. 5, 2012 (English Translation).
EP1478656; Nullity Complaint against DE 603 29 277.1-08 (EP 1 478 656 B1) filed by Fisher Scientific GmbH, plaintiff; Life Technologies Corporation, proprietor. English Translation of portions thereof. May 24, 2011 (English Translation).
EP1478656; Opinion/Brief Issued by Federal Patent Court in Nullity Complaint; DE 603 29 277.1-08 (EP 1 478 656 B1) filed by Fisher Scientific GmbH, plaintiff; Life Technologies Corporation, proprietor. Jun. 22, 2012 (English Translation).
EP1478656; Plaintiff's Complaint dated Feb. 7, 2011, Regional Court Dusseldorf, Life Technologies Corp/Dharmacon Inc. et al. (English Translation).
EP1478656; Plaintiff's Reply to Defendant's Grounds of the Objection; DE 603 29 277.1-08 (EP 1 478 656 B1) filed by Fisher Scientific GmbH, plaintiff; Life Technologies Corporation, proprietor. Jul. 27, 2012 (English Translation).
EP1478656; Plaintiff's Response to Defendant's Observations of the Board's Preliminary Opinion with Attachment (Leake Declaration); DE 603 29 277.1-08 (EP 1 478 656 B1) filed by Fisher Scientific GmbH, plaintiff; Life Technologies Corporation, Nov. 8, 2012 (English Translation).
EP1478656; Plaintiff's Response to Defendant's Reply to Plaintiff's Complaint Opinion, Regional Court Dusseldorf, Life Technologies Corp/Dharmacon Inc. et al. Jul. 31, 2012 (English Translation).
EP2128248; Life Technologies Corp.'s Response to Notice of Opposition dated Sep. 19, 2012.

(56) References Cited

OTHER PUBLICATIONS

EP2128248; Notice of Opposition filed by Thermo Fisher Scientific Inc. dated Feb. 2, 2012.
EP2221377; Notice of Opposition filed by Thermo Fisher Scientific Inc. dated Jul. 25, 2012.
Escude, C. et al., "Rational design of a triple helix-specific intercalating ligand," Proc. Natl. Acad. Sci., vol. 95, 1998, 3591-3596.
Escude, C. et al., "Stable triple helices formed by oligonucleotide N3' -> P5' phosphoramidates inhibit transcription elongation," Proc. Natl. Acad. Sci., vol. 93, 1996, 4365-4369.
Fechheimer et al. "Transfection of mammalian cells with plasmid DNA by scrape loading and sonication loading," Proc. Natl. Acad. Sci. USA, vol. 84, 1987, 8463-8467.
Fisher, T. et al., "Intracellular disposition and metabolism of fluorescently-labeled unmodified and modified oligonucleotides microinjected into mammalian cells," Nucleic Acids Research, vol. 21, No. 16, 1993, 3857-3865.
Flanagan, W. M. et al., "A cytosine analog that confers enhanced potency to antisense oligonucleotides," Proc. Natl. Acad. Sci., vol. 96, 1999, 3513-3518.
Fraley et al., "Entrapment of a bacterial plasmid in phospholipid vesicles: potential for gene transfer,"Proc. Natl. Acad. Sci. USA, vol. 76, 1979, 3348-3352.
Freier et al., "The ups and downs of nucleic acid duplex stability: structure-stability studies on chemically-modified DNA:RNA duplexes," Nucleic Acids Research, vol. 25, No. 22, 1997; pp. 4429-4443.
Froham, Michael, "RACE: Rapid amplification of cDNA ends," PCR protocols: A guide to methods and applications (eds. M.A. Innis, D.H. Gelfand, J.J. Sninsky, and T.J. White), pp. 28-38, 1990 Academic Press, Inc.
Gagnor, C. et al., "α-DNA VI: comparative study of α- and β-anomeric oligodeoxyribonucleotides in hybridization to mRNA and in cell free translation inhibition," Nucleic Acids Research, vol. 15, No. 24, 1987, 10419-10436.
GB0500265.4; Examination Report under Section 18(3) mailed May 27, 2005.
GB0500265.4; Examination Report under Section 18(3) mailed Jul. 28, 2006.
GB0500265.4; Examination Report under Section 18(3) mailed Nov. 29, 2005.
Gillam et al., "Defined transversion mutations at a specific position in DNA using synthetic oligodeoxyribonucleotides as mutagens," Nucleic Acids Resarch, 6(9):2973-2985, 1979.
Gillam et al., "Enzymatic synthesis of oligodeoxyribonucleotides of defined sequence," J. Biol. Chem., vol. 253, 1978, 2532-2539.
Ginobbi, P., "Folic acid-polylysine carrier improves efficacy of c-myc antisense oligodeoxynucleotides on human melanoma (M14) cells," Anticancer Research, vol. 17, 1997, 29-35.
Giovannangeli et al., "Oligonucleotide clamps arrest DNA synthesis on a single-stranded DNA target," Proc. Nat. Acad. Sci. USA, vol. 90, 1993, 10013-10017.
Gitlin et al., "Short interfering RNA confers intracellular antiviral immunity in human cells," Nature, vol. 418, 2002, 430-434.
Gopal, T.V. "Gene transfer method for transient gene expression, stable transformation, and cotransformation of suspension cell cultures," Mol. Cell. Biol., vol. 5, 1985, 1188-1190.
Gorman et al., "Recombinant Genomes Which Express Chloramphenicol Acetyltrasferase in Mammalian Cells," Molecular and Cellular Biology, Sep. 1982; pp. 1044-1051.
Gorman, C. M., "High Efficiency Gene Transfer into Mammalian Cells," DNA Cloning, vol. II, Jul. 1985; pp. 143-190.
Gould, S. J. et al., "Firefly luciferase as a tool in molecular and cell biology," Analytical Biochemistry, vol. 175, 1988, 5-13.
Greene, T. W. et al., Protective Groups in Organic Synthesis, 2d, 1991 John Wiley * son, (Contents).
Griffey et al., "Characterization of Oligonucleotide Metabolism In Vivo via Liquid Chromatography/Electrospray Tandem Mass Spectrometry with a Quadrupole Ion Trap Mass Spectrometer," J. Mass. Spectrom., vol. 32(3), 305-313, 1997.

Grotjahn et al., "Ultrafast sequencing of oligodeoxyribonucleotides by FAR-mass spectrometry," Nucleic Acids Research, vol. 10, 1982; pp. 4671-4678.
Grotli, M et al., "2' -O-Propargyl Oligoribonucleotides: Synthesis and Hybridisation," Tetrahedron, vol. 54, No. 22, 1998, 5899-5914.
Gutierrez, A J. et al., "Antisense Gene Inhibition by C-5-Substituted Deoxyuridine-Containing Oligodeoxynucleotides," Biochemistry, vol. 36, 1997, 743-748.
Hames, B. D. et al., "Nucleic acid hybridisation: a practical approach," Oxford University Press 1985, 5-7 (BRITTEN).
Harland at el., "Translation of mRNA injected into Xenopus oocytes is specifically inhibited by antisense RNA," J. Cell. Biol., 101:1094-1099, 1985.
Helene, C. et al., "Control of gene expression by oligonucleotides covalently linked to intercalating agents," Genome, vol. 31,1989, 413-421.
Ho et al., "Preparation of microemulsions using polyglycerol fatty acid esters as surfactant for the delivery of protein drugs," J. Pharm. Sci., 85 1996, 138-143.
Hochuli, et al. "Genetic Approach to Facilitate Purification of Recombinant Proteins with a Novel Metal Chelate Absorbent", Bio/Tech (Nature Biotechnology), vol. 6, 1988, pp. 1321-1325.
Hoke, G. D. et al., "Effects of phosphorothioate capping on antisense oligonucleotide stability, hybridization and antiviral efficacy versus herpes simplex virus infection," Nucleic Acids Research, vol. 19, No. 20, 1991, 5743-5748.
Innis et al., "DNA sequencing with Thermus aquaticus DNA polymerase and direct sequencing of polymerase chain reaction-amplified DNA," Proc. Natl. Acad. Sci. USA, vol. 85, 1988, 9436-9440.
Ishihara, K. et al., "Effects of phospholipid Adsorption on nonthrombogenicity of Polymer with phospholipid polar group," Journal of Biomedical Materials Research, vol. 27, 1993, 1309-1314.
Itakura et al., "Chemical DNA synthesis and recombinant DNA studies," Science, vol. 209, 1980, 1401-1405.
Itakura et al.," Chemical synthesis and sequence studies of deoxyribooligonucleotides which constitute the duplex sequence of the lactose operator of *Escherichia coli*," J. Biol. Chem., 250:4592 1975.
Jarvis, T. C. et al., "Optimizing the Cell Efficacy of Synthetic Ribozymes," J. Biol. Chem., vol. 271, No. 46, 1996, 29107-29112.
Ji et al., "Enhanced gene silencing by the application of multiple specific small interfering RNAs," FEBS Letters, 552:247-252, 2003.
Johnson et al., "Peptide Turn Mimetics," Biotechnology and Pharmacy (eds. Pezzuto et al.), pp. 367-378, 1993 Chapman & Hall, Inc.
Kamata, H. et al., "Amphiphilic peptides enhance the efficiency of liposome-mediated DNA transfection," Nucleic Acids Research, vol. 22, No. 3, 1994, 536-537.
Kaneda et al., "Increased Expression of DNA Cointroduced with Nuclear Protein in Adult Rat Liver,"Science, vol. 243, 1989, 375-378.
Kato, et al, "Expression of Hepatitis B Virus Surface Antigen in Adult Rat Liver," J. Biol. Chem., vol. 266, 1991, 3361-3364.
Kawasaki et al., "Uniformly modified 2'-deoxy-2'-fluoro-phosphorothioate oligonucleotides as nuclease-resistant antisense compounds with high affinity and specificity for RNA targets," Journal of Medicinal Chemistry, American Chemical Society, vol. 36, No. 7: 831-841, 1993.
Kawasaki, H. et al., "Short hairpin type of dsRNAs that are controlled by tRNA(Val) promoter significantly induce RNAi-mediated gene silencing in the cytoplasm of human cells," Nucleic Acids Research, vol. 31, No. 2, 2003, 700-707.
Khorana, "Total synthesis of a gene," Science, vol. 203, 614, 1979.
Klostermeier and Millar, "Time-resolved fluorescence resonance energy transfer: a versatile tool for the analysis of nucleic acids," Biopolymers, 61(3):159-79, 2001-2002.
Kukreti et al., "Extension of the range of DNA sequences available for triple helix formation: stabilization of mismatched triplexes by acridine-containing oligonucleotides," Nucleic Acids Research, vol. 25, No. 21, 1997, pp. 4264-4270.

(56) References Cited

OTHER PUBLICATIONS

Lacoste, J. et al., "Triple helix formation with purine-rich phosphorothioate-containing oligonucleotides covalently linked to an acridine derivative," Nucleic Acids Research, vol. 25, No. 10, 1997, 1991-1998.

Lamond, A. I., "2'-O-Alkyloligoribonucleotides: Probes for Studying the Biochemistry and Cell Biology of RNA Processing," Biochemical Society Transactions, vol. 21, 1993, pp. 1-8.

Laplanche, et al., "Phosphorotiate-modified oligodeoxyribonucleotides. III. NRM and UV spectroscopic studies of the Rp-Rp, Sp-Sp, and Rp-Sp duplexes, [d(GG2AATTCC)2, derived from diastereomeric O-ethyl phosphorothioates," Nucleic Acids Research, vol. 14, No. 22, 1986, 9081-9093.

Lemaitre, M. et al., "Specific antiviral activity of a poly(L-lysine)-conjugated oligodeoxyribonucleotide sequence complimentary to vesticular somatitis virus N protein mRNA initiation site," Proceedings of the National Academy of Sciences USA, vol. 84, 1987, 648-652.

Letsinger, R. et al., "Cholesteryl-conjugated oligonucleotides: Synthesis, properties, and activity as inhibitors of replication of human immunodeficiency virus in cell culture," Proc. Natl. Acad. Sci., 86(17):6553-6556, 1989.

Lewin, B., "Copying mRNA into DNA," Genes, Third Edition, 1987 John Wiley & Sons, 358-359.

Lewis, F.D. et. al., "The Influence of 5' and 3' End Structures on Pre-mRNA Metabolism", Journal of Cell Science, Supp. 19, 1995, pp. 13-19.

Lewis, J. G. et al., "A Serum-Resistant Cytofectin for Cellular Delivery of Antisense Oligodeoxynucleotides and Plasmid DNA," Proceedings of the National Academy of Sciences, vol. 93, 1996, 3176-3181.

Liang et al. "RNA interference targeted to multiple P2X receptor subtypes attenuates zinc-induced calcium entry" Am. J. Physiol. Cell Physiol., vol. 289: C388-396, 2005.

Liang et al., "Oligonucleotide delivery: a cellular prospective," Pharmazi, 1999, pp. 559-566.

Life Technologies Corporation, "Life in the Lab Products, Information and Scientainment for the Lab," Spring 2012 Canada, pp. 1-30.

Ling, et al. "Cutting Edge: Identification of GL50, a Novel B7-Like Protein that Functionality Binds to ICOS Receptor", Journal of Immunology, vol. 164, Issue 4, 2000, pp. 1653-1657.

Ma et al., "Intracellular mRNA cleavage induced through activation of RNase P by nuclease-resistant external guide sequences," Nature Biotechnology, vol. 18, 2000, 58-61.

Majlessl et al., "Advantages of 2'-O-methyl oligoribonucleotlde probes for detecting RNA targets," Nucleic Acids Research, vol. 26, No. 9, 1988, 2224-2229.

Manoharan et al., "Lipidic Nucleic Acids," Tetrahedron Letters, vol. 36(21), 1995, 3651-3654.

Manoharan, "Oligonucleotide in Antisense Drug Technology," Crooke (ed), Marcel Dekker Inc., 2001, 391-469.

Manoharan, "2'-Carbohydrate Modifications in Antisense Oligonucleotide Therapy: Importance of Conformation, Configuration and Conjugation," Biochimica et Biophysica Acta, vol. 1489, 1999, 117-130.

Marchand et al., "Stabilization of triple-helical DNA by a benzopyridoquinoxaline intercalator," Biochemistry, vol. 35, 1996, 5022-5032.

Matteucci, Mark D. et al., "In Pursuit of Antisense," Nature, vol. 384, Supp 1996, 20-23.

McKay, R. A. et al., "Enhanced Activity of an Antisense Oligonucleotide Targeting Murine Protein Kinase C-alpha by the Incorporation of 2'-O-Propyl Modifications," Nucleic Acids Research, vol. 24, No. 3, 1996, 411-417.

McNeal, C. J. et al., "A New Method for Sequencing Fully Protected Oligonucleotides Using 252Cf-Plasma Desorption Mass Spectrometry," J. Am. Chem. Soc., vol. 104, 1982, 976-980.

Monia, B. et al., "Evaluation of 2'-Modified Oligonucleotides containing 2'-Deoxy Gaps as Antisense Inhibitors of Gene Expression," The Journal of Biological Chemistry, vol. 268, No. 19, 1993, 14514-14522.

Monia, B. et al., "Sequence-specific antitumor activity of a phosphorothioate oligodeoxyribonucleotide targeted to Human C-raf kinase supports an antisense mechanism of action in vivo," Proceedings of the National Academy of Sciences, vol. 93, 1996, 15481-15484.

Morris, M., et. al., A New Peptide Vector for Efficient Delivery of Oligonucleotides Into Mammalian Cells, Nucleic Acids Research, 1997, pp. 2730-2736.

Moulds, C. et al., "Site and Mechanism of Antisense Inhibition by C-5 Propyne Oligonucleotides,"Biochemistry, vol. 34, 1995, 5044-5053.

Murphy et al., "A combinatorial approach to the discovery of efficient cationic peptoid reagents for gene delivery," Proceedings of the National Academy of Sciences USA, vol. 95, 1998, 1517-1522.

Myers et al., "Optimal Alignments in Linear Space," Cabios, vol. 4, 1989, 11-17.

Natarajan et al., "Cis and Trans Activation of Adenovirus Iva2 Gene Transcription," Nucleic Acids Research, vol. 13, No. 11, 1985, 4067-4083.

Nicolau et al. "Liposome-Mediated DNA Transfer in Eukaryotic Cells," Biochim. Biophys. Acta, 721:185-190, 1982.

Nicolau et al. "Liposomes as Carriers for in Vivo Gene Transfer and Expression," Methods Enzymology, 149:157-176, 1987.

Nielsen, D. et al., "Preparation of Capped RNA Transcripts Using T7 RNA Polymerase," Nucleic Acids Research, 14(14), 1986, 5936.

Nielsen et al., "Sequence-Selective Recognition of DNA by Strand Displacement with a Thymidine-Substituted Polyamide," Science, vol. 254, 1991, 1497-1500.

Oberhauser et al., "Effective Incorporation Of 2'-O-Methyl-Oligoribonucleotioes Into Liposomes Ano Enhanced Cell Association Through Modification With Thiocholesterol," Nucleic Acids Research, 20(3), 1992, 533-538.

Ohara et al., "One-sided polymerase chain reaction: The amplification of cDNA," Proc. Natl. Acad. Sci. USA, 86:5673-5677, 1989.

Omirulleh et al. "Activity of a chimeric promoter with the doubled CaMV 35S enhancer element in protoplast-derived cells and transgenic plants in maize," Plant Mol. Biol., 21(3):415-428, 1993.

Ortiagao et al., "Antisence Effect of Oligodeoxynucleotides with Inverted Terminal Internucleotidic Linkages: A Minimal Modification Protecting against Nucleolytic Degradation," Antisense Res. Dev., 2 1992, 129-146.

Pagratis et al., "Potent 2'-amino-, and 2'-fluoro-2'-deoxyribonucleotide RNA inhibitors of keratinocyte growth factor," Nature Biotechnology, vol. 15, 1997, 68-73.

PCT/US03/03208; International Preliminary Examination Report mailed Apr. 26, 2004.

PCT/US03/03208; International Search Report mailed Feb. 13, 2004.

PCT/US03/03223; International Search Report mailed May 3, 2004.

Pooga et al., "Cell penetrating PNA constructs regulate galanin receptor levels and modify pain transmission in vivo," Nature Biotechnology, vol. 16, 1998, 857-861.

Potrykus et al., "Molecular and general genetics of a hybrid foreign gene introduced into tobacco by direct gene transfer," Mol. Gen. Genet., 199(2):169-77, 1985.

Prochiantz, A., "Getting hydrophilic compounds into cells: lessons from homeopeptides," Current Opinion in Neurobiology, vol. 6, 1996, 629-634.

Ratajczak et al., "In vivo treatment of human leukemia in a scid mouse model with c-myb antisense oligodeoxynucleotides," Proceedings of the National Academy of Sciences, vol. 89, 1992, 11823-11827.

Reichhart, J M. et al., "Splice-Activated UAS Hairpin Vector Gives Complete RNAi Knockout of Single or Double Target Transcripts in *Drosophilia melanogaster*," Genesis, vol. 34., No. 1-2, 2002, 160-164.

Rippe et al., "DNA-Mediated Gene Transfer into Adult Rat Hepatocytes in Primary Culture," Mol. Cell. Biol., 10:689-695, 1990.

(56) References Cited

OTHER PUBLICATIONS

Sambrook et al., "Protocol for the Synthesis of the First Strand of cDNA," Molecular Cloning, a Laboratory Manual, Second Edition, Cold Spring Harbor Laboratory Press, pp. 8.60-8.63, 1989.
Schell et al., "Uptake of polynucleotides by mammalian cells.," Biochemical et Biophysica Acta, vol. 340, 1974, 323-333.
Selden et al., "Human Growth Hormone as a Reporter Gene in Regulation Studies Employing Transient Gene Expression," Mol Cell Biol., vol. 6, No. 9, 1986, 3173-3179.
Semple et al., "Efficient Encapsulation of Antisense Oligonucleotides in Lipid Vesicles Using Ionizable Aminolipids: Formation of Novel Small Multilamellar Vesicle Structures," Biochimica et Biophysica Acta, vol. 1510, 2001, 152-166.
Sergeeva et al., "Comparative Study of Modification of DNA and RNA by Oligo(2'-O-Methylribonucleotide) Derivatives," Nucleosides, Nucleotides and Nucleic Acids, vol. 17, No. 9-11: 2153-2156, 1998.
Sharp et al., "RNA interference," Science, 287:2431-2433, 2000.
Shi et al., "Mammalian RNAi for the masses," Trends Genet., vol. 19, 2003, 9-12.
Shoeman, R.L. et al., "Fluorescence Microscopic Comparison of the Binding of Phosphodiester and Phosphorothioate (Antisense) Oligodeoxyribonucleotides to Subcellular Structures, Including Intermediate Filaments, the Endoplasmic Reticulum, and the Nuclear Interior," Antisense & Nuc. Acid Drug Dev., vol. 7, 1997, 291-308.
Shuey et al., "RNAi: gene-silencing in therapeutic intervention," Drug Discov. Today, vol. 7, No. 20, 2002, 1040-1046.
Simeoni et al., "Peptide-Based Strategy for siRNA Delivery into Mammalian Cells," Methods in Molecular Biology, vol. 309: RNA Silencing: Methods and Protocols, 2005, 251-260.
Siomi et al., "Identification of Components of RNAi Pathways Using the Tandem Affinity Purification Method," RNA Silencing, Methods and Protocols, vol. 309, Humana Press 2005; pp. 1-9.
Sioud et al., "Strategies for the Design of Random siRNA Libraries and the Selection of anti-GFP siRNAs," Methods in Molecular Biology, vol. 309: RNA Silencing: Methods and Protocols, 2005, 83-91.
Sioud, M., "siRNA Delivery In Vivo," Methods in Molecular Biology, vol. 309: RNA Silencing: Methods and Protocols, 2005, 237-249.
Sonveaux, E., "Protecting Groups in Oligonucleotide Synthesis," Methods in Molecular Biology, vol. 26: Protocols for Oligonucleotide Conjugates, 1994, 1-71.
Soutschek et al., "Therapeutic silencing of an endogenous gene by systemic administration of modified siRNAs," Nature, vol. 432, 2004, 173-178.
Spänkuck-Schmitt et al., "Effect of RNA Silencing of Polo-Like Kinase-1 (PLK1) on Apoptosis and Spindle Formation in Human Cancer Cells," Journal of the National Cancer Institute, 94(24):1863-1877, Dec. 18, 2002.
Sproat et al., "Highly Efficient Chemical Synthesis of 2'-0-methylioligoribunocleotides and Tetrabiotinylated Derivatives;Novel Probes That are Resistant to Degradation by RNA or DNA Specific Nucleases," Nucleic Acids Research, 17(9):3373-3386, 1989.
Stec et al., "Automated Solid-Phase Synthesis, Separation, and Sterochemistry of Phosphorothioate Analogues of Oligodeoxyribonucleotides," J. Am. Chem. Soc., vol. 106,1984, pp. 6077-6079.
Stec et al., "Reversed-phase high-performance liquid chromatographic separation of diastereomeric phosphorothioate analogues of oligodeoxyribonucleotides and other backbone-modified congeners of DNA," J. Chromatog., vol. 326, 1985, 263-280.
Stec et al., "Solid-Phase Synthesis, Separation, and Sterochemical Aspects of P-Chiral Methane and 4,4'-Dimethoxytriphenylmethanephosphonate Analogues of Oligodeoxyribonucleotides," J. Org. Chem., vol. 50, 1985, 3908-3913.

Stein et al., "A Specificity Comparison of Four Antisense Types: Morpholino, 2'-O-methyl RNA, DNA, and Phosphorothioate DNA," Antisense & Nucleic Acid Drug Development, vol. 7, 1997, pp. 151-157.
Stein et al., "Antisense Oligonucleotides as Therapeutic Agents—Is the Bullet Really Magical?," Science, vol. 261, 1993, 1004-1012.
Stein et al., "Two problems in antisense biotechnology: in vitro delivery and the design of antisense experiments," Biochimica et Biophyica Acta, vol. 1489, 1999, 45-52.
Subramaniam et al., "nos-1 and nos-2, two genes related to *Drosphila nanos*, regulate primordial germ cell development and survival in Caenorhabditis elegans," Development, vol. 126, No. 21: 4861-4871, 1999.
Summerton, "Morpholino Antisense Oligomers: Design, Preparation and Properties," Antisense & Nuc. Acid Drug Dev., 7, 1997, 187-195.
Summerton, et al. "Morphiolino and Phosphorothioate Antisense Oligomers Compared in Cell-Free and In-Cell Systems", Antisense & Nucleic Acid Drug Development, vol. 7, Issue 2, 1997, pp. 63-70.
Sun Qi et al., "Complex genetic interactions among four receptor tyrosine phosphates regulate axon guidance in *Drosophila*," Molecular and Cellular Neuroscience, vol. 17, No. 2: 274-291; 2001.
Theus et al., "A Simple Assay for Determining the Capping Efficiencies of RNA Polymerases Used for In Vitro Transcription," BioTechniques, vol. 9, No. 5, 1990, 610-615.
Thuong et al. "Oligo(Alpha-Deosynucleotide)s Covalently Linked to Intercalating Agents: Differential Binding to Ribo- and Deoxyribopolynucleotides and Stability Towards Nuclease Digestion," Proc Nat Acad Sci USA, vol. 84, 1987, 5129-5133.
Troy et al., "Downregulation of Cu/Zn superoxide dismutase leads to cell death via the nitric oxide-peroxynitrite pathway," The Journal of Neuroscience, vol. 16, No. 1, 1996, 253-261.
Tuschl et al., "Review of siRNA Application Written at Dr. Tuschl's Lab—http//www.mpibpc/gwdg.de/abteilunger/100/105/sirna. html," p. 105, Aug. 26, 2001.
Tuschl, T., et. al., The siRNA user guide, Review of siRNA application written at Dr. Tuschl's Lab—http://www.mpibpc.gwdg. de/abteilungen/100/105/sirna.html, 2001, pp. 1-5.
Uhlmann et al., "Antisense Oligonucleotides: A New Therapeutic Principle," Chemical Reviews, vol. 90, No. 4: 543-583, 1990.
Verma et al., "Gene Therapy—Promises, Problems and Prospects," Nature, vol. 389, 1997, 239-242.
Viari et al., "Sequence Analysis of Unprotected Tri-Deoxyribonucleoside Diphosphates by 252Cf-Plasma Desorption Mass Spectrometry," Biomed. Environ. Mass Spectrom., vol. 14, 1987, 83-90.
Vlassov et al., "Transport of oligonucleotides across natural and model membranes," Biochimica et Biophysica Acta, vol. 1197, 1994, 95-108.
Wagner, R. W. et al., "Antisense Gene Inhibition by Oligonucleotides Containing C-5 Propyne Pyrimidines," Science, vol. 260, 1993, 1510-1513.
Wagner, R. W. et al., "Potent and selective inhibition of gene expression by an antisense heptanucleotide," Nature Biotechnology, vol. 14, 1996, 840-844.
Wagner, R. W., "The State of The Art in Antisense Research," Nature Medicine, vol. 1, No. 11, 1995, 1116-1118.
Walker et al., "Isothermal in vitro amplification of DNA by restriction enzyme / DNA polymerase system," Proc. Natl. Acad. Sci. USA, 89:392-396, 1992.
Wilson, J.M., "Gene therapy for Cystic Fibrosis: Challenges and Future Directions," Journal of Clinical Investigation, vol. 96, 1995, 2547-2554.
Wong et al., "Appearance of beta-lactamase activity in animal cells upon liposome-mediated gene transfer," Gene, 10, 1980, 87-94.
Yamakawa et al., "Properties and Anti-HIV Activity of Nicked Dumbbell Oligonucleotides," Nucleosides & Nucleotides, 15 (1-3), 1996, 519-529.
Yang et al., "Evidence that processed small dsRNAs may mediate sequence-specific mRNA degradation during RNAi in *Drosophila* embryos," Current Biology, vol. 10, No. 19, 2000, 1191-120.

(56) References Cited

OTHER PUBLICATIONS

Yang, et al. "Computational Molecular Evolution", Oxford University Press, USA (Oxford Series in Ecology and Evolution), 2006.

Zabner et al., "Cellular and Molecular Barriers to Gene Transfer by a Cationic Lipid," Journal of Biological Chemistry, 270(32):18997-19007, Aug. 1995.

Zamore, "Thirty-Three Years Later, a Glimpse at the Ribonuclease III Active Site," Molecular Cell, 8(6):1158-1160, Dec. 1, 2001.

Zuckermann et al., "Design, construction and application of a fully automated equimolar peptide mixture synthesizer," Int. J. Peptide Protein Res., vol. 40, 1992, 497-506.

Zuckermann, et al. "Efficient Mthod for the Preparation of Peptoids [Oligo(N-Substituted Glycines)] by Submonomer Solid-Phase Synthesis", Journal of the American Chemical Society, vol. 114, No. 26, 1996, pp. 10646-100647.

Figure 7
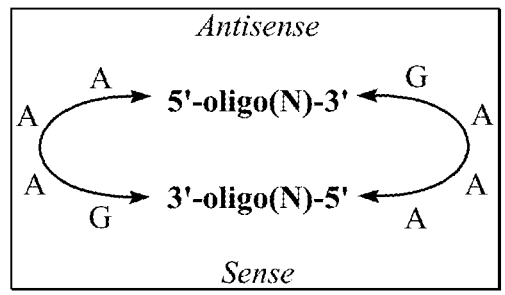
Figure 8
```
5'-(Z)2-8-(N)15-40-(M)2-8-3'        (Antisense)
3'-(Z)2-8-(N)15-40-(M)2-8-5'        (Sense)
```
Figure 9
```
GGCCCUUCUGUCUUGAACAUGAGUU  G A A
                                  A
CCGGGaaGaCaGaaCTTGTaCTCAA A      
                           A A G
```
Figure 10
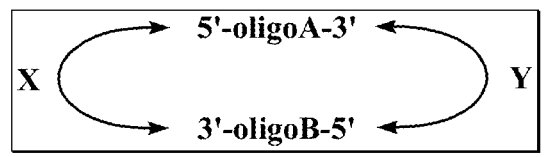

*Effect of structural changes on efficacy of siRNAs targeting p53: 21-mers vs. 27-mers with and without 3'-deoxy TT overhangs.*

*Effect of structural changes on the efficacy of siRNAs targeting β-3-integrin: 21-mer v. 27-mer.*

*Effect of p53-targeted and non-targeted siRNAs on PKR expression in A549 cells.*

*Effect of β-3-integrin targeted 21-mer and 27-mers on PKR expression in HMVEC cells.*

*Effect of 5' vs. 3' modification on activity.*

*Effect of the size of the modifying group on activity of the double-stranded RNA duplex.*

*Effect of 2'-O-methyl modified siRNAs on p53 expression.*

*(Left to right: first three targeted, next three matched controls, then one targeted, and three additional controls.)*

*Inhibition of p53 by 32- and 37-mer blunt-end siRNAs.*

DOUBLE-STRANDED OLIGONUCLEOTIDES

RELATED APPLICATIONS

This application is a continuation of U.S. Ser. No. 13/277,957 filed on Oct. 20, 2011, which is a continuation application of U.S. Ser. No. 12/062,380 filed on Apr. 3, 2008, now abandoned, which is a continuation application of U.S. Ser. No. 11/049,636 filed on Feb. 2, 2005, now abandoned, which claims the benefit of U.S. Provisional Application Nos. 60/615,408 filed on Sep. 30, 2004, and 60/540,552 filed on Feb. 2, 2004. U.S. Ser. No. 11/049,636 is also a continuation-in-part of U.S. Ser. No. 10/357,529 filed Feb. 3, 2003, now abandoned, and Ser. No. 10/357,826 filed Feb. 3, 2003, now abandoned, both of which claim the benefit of U.S. Provisional Application Nos. 60/353,203 filed on Feb. 1, 2002, 60/436,238 filed Dec. 23, 2002, 60/438,608 filed Jan. 7, 2003, and 60/353,381 filed Feb. 1, 2002. The entire contents of the aforementioned applications are hereby expressly incorporated herein by reference.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

BACKGROUND OF THE INVENTION

Complementary oligonucleotide sequences are promising therapeutic agents and useful research tools in elucidating gene function. However, oligonucleotide molecules of the prior art are often subject to nuclease degradation when applied to biological systems. Therefore, it is often difficult to achieve efficient inhibition of gene expression (including protein synthesis) using such compositions.

In order to maximize the usefulness, such as the potential therapeutic activity and in vitro utility, of oligonucleotides that are complementary to other sequences of interest, it would be of great benefit to improve upon the prior art oligonucleotides by designing improved oligonucleotides having increased stability both against serum nucleases and cellular nucleases and nucleases found in other bodily fluids.

SUMMARY OF THE INVENTION

The instant invention is based, at least in part, on the discovery that double-stranded oligonucleotides comprising an antisense oligonucleotide and a protector oligonucleotide, are capable of inhibiting gene function. Thus, the invention improves the prior art antisense sequences, inter alia, by providing oligonucleotides which are resistant to degradation by cellular nucleases.

Accordingly, the invention provides optimized oligonucleotide compositions and methods for making and using both in in vitro, and in vivo systems, e.g., therapeutically.

In one aspect, the invention pertains to a double-stranded oligonucleotide composition having the structure depicted in FIG. 1, where (1) N is a nucleomonomer in complementary oligonucleotide strands of equal length and where the sequence of Ns corresponds to a target gene sequence and (2) X and Y are each independently selected from a group consisting of nothing; from about 1 to about 20 nucleotides of 5' overhang; from about 1 to about 20 nucleotides of 3' overhang; and a loop structure consisting from about 4 to about 20 nucleomonomers, where the nucleomonomers are selected from the group consisting of G and A. The invention further includes compositions such as reaction mixtures comprising such double-stranded oligonucleotides, as well as methods for using such double-stranded oligonucleotides.

An "overhang" is a relatively short single-stranded nucleotide sequence on the 5'- or 3'-hydroxyl end of a double-stranded oligonucleotide molecule (also referred to as an "extension," "protruding end," or "sticky end").

In one embodiment, the number of Ns in each strand of the duplex is between about 12 and about 50. In other embodiments, the number of Ns in each strand of the duplex is between about 12 and about 40 (i.e., in the structure above, oligo(N) has between about 12 and about 50 nucleomonomers); or between about 15 and about 35; or more particularly between about 20 and about 30; or even between about 21 and about 25.

In one embodiment, X is a sequence of about 4 to about 20 nucleomonomers which form a loop, wherein the nucleomonomers are selected from the group consisting of G and A.

In one embodiment, two of the Ns are unlinked, i.e., there is no phosphodiester bond between the two nucleomonomers. In one embodiment, the unlinked Ns are not in the antisense sequence.

In one embodiment, the nucleotide sequence of the loop is GAAA.

In another aspect, the invention pertains to a double-stranded oligonucleotide composition having the structure depicted in FIG. 2, where (1) N is a nucleomonomer in complementary oligonucleotide strands of equal length where the sequence of Ns corresponds to a target gene sequence; and (2) Z is a nucleomonomer in complementary oligonucleotide strands of between about 2 and about 8 nucleomonomers in length and where the sequence of Z optionally corresponds to the target sequence; and (3) where M is a nucleomonomer in complementary oligonucleotide strands of between about 2 and about 8 nucleomonomers in length and where the sequence of Ms optionally corresponds to the target sequence. Although the sequences of N nucleomonomers should be of the same length, the sequences of Z and M nucleomonomers may optionally be of the same length. The invention further includes compositions such as reaction mixtures comprising such double-stranded oligonucleotides, as well as methods for using such double-stranded oligonucleotides.

In one embodiment, Z and M are nucleomonomers selected from the group consisting of C and G.

In one embodiment, the sequence of Z or M is CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC, or CCGG.

In another aspect, the invention pertains to a double-stranded oligonucleotide composition having the structure depicted in FIG. 3, where (1) N is a nucleomonomer in complementary oligonucleotide strands of equal length and where the sequence of Ns corresponds to a target gene sequence and (2) X is selected from the group consisting of nothing; 1-20 nucleotides of 5' overhang; 1-20 nucleotides of 3' overhang. The invention further includes compositions such as reaction mixtures comprising such double-stranded oligonucleotides, as well as methods for using such double-stranded oligonucleotides.

In some embodiments, X is a loop structure consisting of from about 4 to about 20 nucleomonomers, where the nucleomonomers are selected from the group consisting of G and A.

In the structure above, M is a nucleomonomer in complementary oligonucleotide strands of between about 2 and about 8 nucleomonomers in length which optionally correspond to the target sequence. In one embodiment, M is a nucleomonomer selected from the group consisting of contain C and G.

In one embodiment, the sequence of M is CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC, or CCGG.

In another aspect, the invention pertains to a double-stranded oligonucleotide composition having the structure depicted in FIG. 4, where (1) N is a nucleomonomer in complementary oligonucleotide strands of equal length and which correspond to a target gene sequence and (2) Y is selected from the group consisting of nothing; 1-20 nucleotides of 5' overhang; 1-20 nucleotides of 3' overhang; a loop consisting of a sequence of from about 4 to about 20 nucleomonomers, where the nucleomonomers are all either G's or A's and (3) where Z is a nucleomonomer in complementary oligonucleotide strands of between about 2 and about 8 nucleomonomers in length and which comprise a sequence which can optionally correspond to the target sequence. The invention further includes compositions such as reaction mixtures comprising such double-stranded oligonucleotides, as well as methods for using such double-stranded oligonucleotides.

In one embodiment, Zs are nucleomonomers selected from the group consisting of C and G.

In one embodiment, the sequence of Z is CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC, or CCGG.

In another aspect, the invention pertains to a method of regulating gene expression in a cell, comprising forming a double-stranded oligonucleotide composition as described herein and contacting a cell with the double-stranded duplex, to thereby regulate gene expression in a cell.

In one embodiment, the invention pertains to a method of increasing the nuclease resistance of an antisense sequence, comprising forming a double-stranded oligonucleotide composition as described herein, such that a double-stranded duplex is formed, wherein the nuclease resistance of the antisense sequence is increased compared to a double-stranded, unmodified RNA molecule.

In other embodiments, the invention includes methods for introducing one or more double-stranded nucleic acid molecule into cells (e.g., eukaryotic cells). In particular embodiments, such methods include those comprising contacting cells (e.g., eukaryotic cells) with one or more double-stranded nucleic acid molecule. In more specific embodiments, at least the first two (e.g., the first two, the first three, the first four, the first five, etc.) nucleotides at the 5' terminus of the first strand of the one or more double-stranded nucleic acid molecule are chemically modified at the 2' positions and/or at least the first two nucleotides at the 5' terminus of the second strand of the one or more double-stranded nucleic acid molecule are chemically modified at the 2' positions. In additional specific embodiments, the double-stranded nucleic acid molecule may be between 18 and 30, between 20 and 30, or between 22 and 30 nucleosides in length. Further, the double-stranded nucleic acid molecule may be 25 nucleosides in length. The invention further includes compositions (e.g., double-stranded nucleic acid molecule, reaction mixtures, etc.) used in these methods.

In various embodiments of the invention (e.g., those described in the preceding paragraph), the double-stranded nucleic acid molecule may contain an overhang (e.g., a 3' overhang and/or a 5' overhang) of at least one (e.g., one, two, three, four, five, etc.) nucleoside on at least one end (e.g., one end or both ends). Additionally, the nucleosides of the overhang(s) may be deoxy nucleosides such as deoxy-T. In specific embodiments, the overhang(s) may be or contain deoxy T-deoxy T.

Further, when nucleic acid molecules in compositions of the invention or used in methods of the invention are chemically modified at one or more 2' position, the 2' chemical modification(s) may be a 2'-O-methyl modification, a 2'-O-propyl modification, a 2'-O-ethyl modification, a 2'-fluoro modification, or a combination of such modifications. Additionally, 2' chemical modification on such nucleic acid molecules may be located on ribose sugars, deoxyribose sugars, or a combination of these sugars.

Further, nucleic acid molecules of the invention may be combined with one or more transfection reagent to form a composition. Additionally, such compositions may be contacted with cells (e.g., eukaryotic cells). Transfection reagents used in such methods and compositions may comprise one or more cationic lipid. One example of a transfection reagent which may be used in the practice of the invention is LIPOFECTAMINE 2000™. The invention thus includes methods which employ and compositions which contain transfection reagents.

The invention additionally includes methods by which nucleic acid molecules (e.g., double-stranded nucleic acid molecules) may be introduced into eukaryotic cells by electroporation.

Further, when double-stranded nucleic acid molecules (e.g., double-stranded RNA molecules) are used in the practice of the invention, one strand of these double-stranded nucleic acid molecules may be complementary to all or part of the nucleotide sequence of an RNA (e.g., an mRNA) which is expressed in a cell (e.g., a eukaryotic cell into which the double-stranded nucleic acid molecules are introduced). When the RNA is a mRNA, introduction of double-stranded nucleic acid molecules in cells may inhibit expression of protein from such RNA. Thus, the invention includes methods for inhibiting gene expression.

Methods of stabilizing oligonucleotides, particularly antisense oligonucleotides, by formation of a oligonucleotide compositions comprising at least 3 different oligonucleotides, are disclosed in co-pending application U.S. application Ser. No. 10/357,826. This application and all of its teachings is hereby expressly incorporated herein by reference in its entirety.

BRIEF DESCRIPTION OF THE DRAWINGS

FIG. 7 A depiction of an exemplary composition.
FIG. 8 A depiction of an exemplary composition.
FIG. 9 A depiction of an exemplary composition. (SEQ ID NO:13)
FIG. 10 A depiction of an exemplary composition.

DETAILED DESCRIPTION OF THE INVENTION

Figure 1:
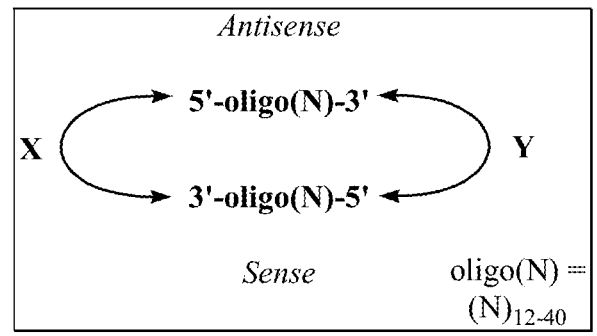
FIG. 1 A depiction of an exemplary composition.
Figure 2:
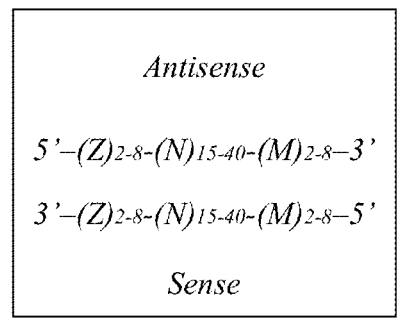
FIG. 2 A depiction of an exemplary composition.

The instant invention advances the prior art by providing double-stranded oligonucleotide compositions for use, both in vitro and in vivo, e.g., therapeutically, and by providing methods of making and using the double-stranded antisense oligomer compositions.

Double-Stranded Oligonucleotide Compositions

Double-stranded oligonucleotides of the invention are capable of inhibiting the synthesis of a target protein, which is encoded by a target gene. The target gene can be endogenous or exogenous (e.g., introduced into a cell by a virus or using recombinant DNA technology) to a cell. As used herein, the term "target gene" includes polynucleotides comprising a region that encodes a polypeptide or polynucleotide region that regulates replication, transcription, translation, or other process important in expression of the target protein; or a polynucleotide comprising a region that encodes the target polypeptide and a region that regulates expression of the target polypeptide; or non-coding regions such as the 5' or 3' UTR or introns. Accordingly, the term "target gene" as used herein may refer to, for example, an mRNA molecule produced by transcription from a gene of interest. Furthermore, the term "correspond," as in "an oligomer corresponds to a target gene sequence," means that the two sequences are complementary or homologous or bear such other biologically rational relationship to each other (e.g., based on the sequence of nucleomonomers and their base-pairing properties).

The "target gene" to which an RNA molecule of the invention is directed may be associated with a pathological condition. For example, the gene may be a pathogen-associated gene, e.g., a viral gene, a tumor-associated gene, or an autoimmune disease-associated gene. The target gene may also be a heterologous gene expressed in a recombinant cell or a genetically altered organism. By determining or modulating (e.g., inhibiting) the function of such a gene, valuable information and therapeutic benefits in medicine, veterinary medicine, and biology may be obtained.

The term "oligonucleotide" includes two or more nucleomonomers covalently coupled to each other by linkages (e.g., phosphodiesters) or substitute linkages. In one embodiment, it may be desirable to use a single-stranded nucleic acid molecule which forms a duplex structure (e.g., as described in more detail below). For example, in one embodiment, the oligonucleotide can include a nick in either the sense of the antisense sequence.

The term "antisense" refers to a nucleotide sequence that is inverted relative to its normal orientation for transcription and so expresses an RNA transcript that is complementary to a target gene mRNA molecule expressed within the host cell (e.g., it can hybridize to the target gene mRNA molecule through Watson-Crick base pairing). An antisense strand may be constructed in a number of different ways, provided that it is capable of interfering with the expression of a target gene. For example, the antisense strand can be constructed by inverting the coding region (or a portion thereof) of the target gene relative to its normal orientation for transcription to allow the transcription of its complement, (e.g., RNAs encoded by the antisense and sense gene may be complementary). Furthermore, the antisense oligonucleotide strand need not have the same intron or exon pattern as the target gene, and noncoding segments of the target gene may be equally effective in achieving antisense suppression of target gene expression as coding segments.

Accordingly, one aspect of the invention is a method of inhibiting the activity of a target gene by introducing an RNAi, also referred to as RNA interference, agent into a cell, such that the dsRNA component of the RNAi agent is targeted to the gene. In one embodiment, an RNA oligonucleotide molecule may contain at least one nucleomonomer that is a modified nucleotide analogue. The nucleotide analogues may be located at positions where the target-specific activity, e.g., the RNAi mediating activity is not substantially effected, e.g., in a region at the 5'-end or the 3'-end of the double-stranded molecule, where the overhangs may be stabilized by incorporating modified nucleotide analogues.

In another aspect, double-stranded RNA molecules known in the art can be used in methods of the present invention. Double-stranded RNA molecules known in the art may also be modified according to the teachings herein in conjunction with such methods, e.g., by using modified nucleomonomers. For example, see U.S. Pat. No. 6,506,559; U.S. 2002/0,173,478 A1; U.S. 2002/0,086,356 A1; Shuey, et al., "RNAi: gene-silencing in therapeutic intervention." Drug Discov. Today 2002 Oct. 15; 7(20):1040-6; Aoki, et al., "Clin. Exp. Pharmacol. Physiol. 2003 January; 30(1-2):96-102; Cioca, et al., "RNA interference is a functional pathway with therapeutic potential in human myeloid leukemia cell lines. Cancer Gene Ther. 2003 February; 10(2):125-33.

Further examples of double-stranded RNA molecules include those disclosed in the following references: Kawasaki, et al., "Short hairpin type of dsRNAs that are controlled by tRNA(Val) promoter significantly induce RNAi-mediated gene silencing in the cytoplasm of human cells." Nucleic Acids Res. 2003 Jan. 15; 31(2):700-7; Cottrell, et al., "Silence of the strands: RNA interference in eukaryotic pathogens." Trends Microbiol. 2003 January; 11(1):37-43; Links, "Mammalian RNAi for the masses." Trends Genet. 2003 January; 19(1):9-12; Hamada, et al., "Effects on RNA interference in gene expression (RNAi) in cultured mammalian cells of mismatches and the introduction of chemical modifications at the 3'-ends of siRNAs." Antisense Nucleic Acid Drug Dev. 2002 October; 12(5):301-9; Links, "RNAi and related mechanisms and their potential use for therapy." Curr. Opin. Chem. Biol. 2002 December; 6(6):829-34; Kawasaki, et al., "Short hairpin type of dsRNAs that are controlled by tRNA(Val) promoter significantly induce RNAi-mediated gene silencing in the cytoplasm of human cells." Nucleic Acids Res. 2003 Jan. 15; 31(2):700-7).

A nick is two non-linked nucleomonomers in an oligonucleotide. A nick can be included at any point along the sense or antisense nucleotide sequence. In a preferred embodiment, a nick is in the sense sequence. In another preferred embodiment, the nick is at least about four nucleomonomers in from an end of the duplexed region of the oligonucleotide (e.g., is at least about four nucleomonomers away from the 5' or 3' end of the oligonucleotide or away from a loop structure. For example, in one embodiment, the nick is present in the middle of the sense strand of the duplex molecule (e.g., if the sense sequence of the duplex is 30 nucleomonomers in length, nucleomonomers 14 and 15 or 15 and 16 are unlinked). In an embodiment, a nick may optionally be ligated to form a circular nucleic acid molecule.

Figure 5:
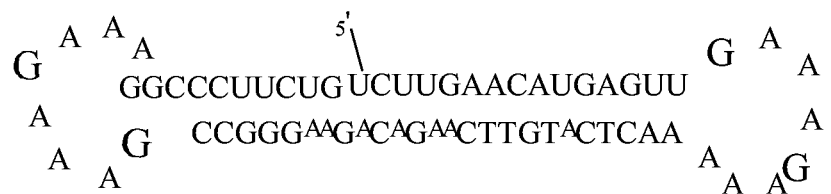
FIG. 5 A depiction of an exemplary composition. (SEQ ID NO:1)
FIG. 6 Shows an exemplary high affinity nucleomonomer.

For example, in the structure shown in FIG. 5, the indicated U nucleomonomer is not bonded to the neighboring nucleomonomer, e.g., by a phosphodiester bond. The 5' OH of the nick may optionally be phosphorylated to allow enzymatic ligation of the oligonucleotide into a circle.

As used herein, the term "nucleotide" includes any monomeric unit of DNA or RNA containing a sugar moiety (pentose), a phosphate, and a nitrogenous heterocyclic base. The base is usually linked to the sugar moiety via the glycosidic carbon (at the 1' carbon of pentose) and that combination of base and sugar is called a "nucleoside." The base characterizes the nucleotide with the four customary bases of DNA being adenine (A), guanine (G), cytosine (C) and thymine (T). Inosine (I) is an example of a synthetic base that can be used to substitute for any of the four, naturally-occurring bases (A, C, G, or T). The four RNA bases are A, G, C, and uracil (U). Accordingly, an oligonucleotide may be a nucleotide sequence comprising a linear array of nucleotides connected by phosphodiester bonds between the 3' and 5' carbons of adjacent pentoses. Other modified nucleosides/nucleotides are described herein and may also be used in the oligonucleotides of the invention.

Oligonucleotides may comprise, for example, oligonucleotides, oligonucleosides, polydeoxyribonucleotides (containing 2'-deoxy-D-ribose) or modified forms thereof, e.g., DNA, polyribonucleotides (containing D-ribose or modified forms thereof), RNA, or any other type of polynucleotide which is an N-glycoside or C-glycoside of a purine or pyrimidine base, or modified purine or pyrimidine base. The term oligonucleotide includes compositions in which adjacent nucleomonomers are linked via phosphorothioate, amide or other linkages (e.g., Neilsen, P. E., et al. 1991. *Science.* 254:1497). Generally, the term "linkage" refers to any physical connection, preferably covalent coupling, between two or more nucleic acid components, e.g., catalyzed by an enzyme such as a ligase.

In addition to its art-recognized meaning (e.g., a relatively short length single or double-stranded sequences of deoxyribonucleotides or ribonucleotides linked via phosphodiester bonds), the term "oligonucleotide" includes any structure that serves as a scaffold or support for the bases of the oligonucleotide, where the scaffold permits binding to the target nucleic acid molecule in a sequence-dependent manner.

Oligonucleotides of the invention are isolated. The term "isolated" includes nucleic acid molecules which are synthesized (e.g., chemically, enzymatically, or recombinantly) or are naturally occurring but separated from other nucleic acid molecules which are present in a natural source of the nucleic acid. Preferably, a naturally occurring "isolated" nucleic acid molecule is free of sequences which naturally flank the nucleic acid molecule (i.e., sequences located at the 5' and 3' ends of the nucleic acid molecule) in a nucleic acid molecule in an organism from which the nucleic acid molecule is derived.

The term "nucleomonomer" includes a single base covalently linked to a second moiety. Nucleomonomers include, for example, nucleosides and nucleotides. Nucleomonomers can be linked to form oligonucleotides that bind to target nucleic acid sequences in a sequence specific manner.

In one embodiment, modified (non-naturally occurring) nucleomonomers can be used in the oligonucleotides described herein. For example, nucleomonomers may be based on bases (purines, pyrimidines, and derivatives and analogs thereof) bound to substituted and unsubstituted cycloalkyl moieties, e.g., cyclohexyl or cyclopentyl moieties, and substituted and unsubstituted heterocyclic moieties, e.g., 6-member morpholino moieties or, preferably, sugar moieties.

Sugar moieties include natural, unmodified sugars, e.g., monosaccharides (such as pentoses, e.g., ribose, deoxyribose), modified sugars and sugar analogs. Possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like. One particularly useful group of modified nucleomonomers are 2'-O-methyl nucleotides, especially when the 2'-O-methyl nucleotides are used as nucleomonomers in the ends of the oligomers. Such 2'O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a nonnaturally occurring base (instead of a naturally occurring base) such as uridines or cytidines modified at the 5-position, e.g., 5-(2-amino)propyl uridine and 5-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alkoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

In one embodiment, sense oligomers may have 2' modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). Likewise, the antisense strand may have 2' modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). In preferred aspects, such 2'-modifications are in the sense RNA strand or the sequences other than the antisense strand.

To further maximize endo- and exonuclease resistance, in addition to the use of 2' modified nucleomonomers in the ends, inter-nucleomonomer linkages other than phosphodiesters may be used. For example, such end blocks may be used alone or in conjunction with phosphothioate linkages between the 2'-O-methyl linkages. Preferred 2'-modified nucleomonomers are 2'-modified C and U bases.

Although the antisense strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

One particular example of a composition of the invention has end-blocks on both ends of a sense oligonucleotide and only the 3' end of an antisense oligonucleotide. Without wishing to be bound by theory, the inventors believe that a 2'-O-modified sense strand works less well than unmodified because it is not efficiently unwound. Accordingly, another embodiment of the invention includes duplexes in which nucleomonomer-nucleomonomer mismatches are present in a sense 2'-O-methyl strand (and are thought to be easier to unwind).

Accordingly, for a given first oligonucleotide strand, a number of complementary second oligonucleotide strands are permitted according to the invention. For example, in the following Tables, a targeted and a non-targeted oligonucleotide are illustrated with several possible complementary oligonucleotides. The individual nucleotides may be 2'-OH RNA nucleotides (R) or the corresponding 2'-O-methyl nucleotides (M), and the oligonucleotides themselves may contain mismatched nucleotides (lower case letters).

Targeted Oligonucleotide:

First Strand:
(SEQ ID NO: 2)
CCCUUCUGUCUUGAACAUGAG

Second Strand:
(SEQ ID NO: 3)
CTgATGTTCAAGACAGAAcGG
(methyl groups →) MMMMMMMMMMMMMMMMMMMMM (SEQ ID NO: 4)
CTgATGTTCAAGACAGAAcGG
RRRRRRRRRRRRRRRRRRRDD (SEQ ID NO: 5)
CTCAUGUUCAAGACAGAAGGG
RRRRRMMMMMMMMMRRRRRR (SEQ ID NO: 6)
CTCAUGUUCAAGACAGAAGGG
MMMMMRRRRRRRRRMMMMMM (SEQ ID NO: 7)
CTCAUGUUCAAGACAGAAGGG
RMRMRMRMRMRMRMRMRMRMR Non-Targeted Oligonucleotide:

First Strand:
(SEQ ID NO: 8)
GAGTACAAGTTCTGTCTTCCC

Second Strand:
(SEQ ID NO: 9)
GGcAAGACAGAACTTGTAgTC
(methyl groups →) MMMMMMMMMMMMMMMMMMMMM (SEQ ID NO: 10)
GGGAAGACAGAACTTGTACTC
RRRRRRMMMMMMMMMRRRRRR (SEQ ID NO: 11)
GGGAAGACAGAACTTGTACTC
MMMMMMRRRRRRRRRMMMMMM (SEQ ID NO: 12)
GGGAAGACAGAACTTGTACTC
RMRMRMRMRMRMRMRMRMRMR Another example of further modifications that may be used in conjunction with 2'-O-methyl nucleomonomers are modification of the sugar residues themselves, for example alternating modified and unmodified sugars, particularly in the sense strand.

The invention further includes double stranded nucleic acid molecules (e.g., RNA molecules) which have structures defined by the following formula:

| First Strand | $X_{15-30}$ |
|---|---|
| Second Strand | $A_{0-25}X_{0-25}B_{0-25}$ |

In the formula set out above, X, A, and B are nucleotides (e.g., A, G, C, U, etc.). Also, either of the first strand or the second strand may be a sense strand. As a results, either of the first strand or the second strand may be an antisense strand. Further, X is typically a nucleotide which has no modifications on the base or sugar. Further, A and/or B are nucleotides which may independently contain one or more base or sugar modifications. These modifications may be any modifications known in the art or described elsewhere herein. Examples of sugar modifications include ribose modifications at the 2' position such as 2'-O-propyl (P), 2'-O-methyl (M), 2'-β-ethyl (E), and 2'-fluoro (F). Generic examples of nucleic acid molecules of the invention include those with the following:

XXXXXXXXXXXXXXXXXXXX

AXXXXXXXXXXXXXXXXXXXB

XXXXXXXXXXXXXXXXXXXX

AAXXXXXXXXXXXXXXXXXBB

XXXXXXXXXXXXXXXXXXXX

AAAXXXXXXXXXXXXXXXBBB

XXXXXXXXXXXXXXXXXXXX

AAAAXXXXXXXXXXXXXBBBB

XXXXXXXXXXXXXXXXXXXX

AAAAXXXXXXXXXXXXXXXBB

XXXXXXXXXXXXXXXXXXXX

-continued

```
AAXXXXXXXXXXXXXXBBBBB

XXXXXXXXXXXXXXXXXXXX

AAAAAAAAAAAAAAAAAAAA

XXXXXXXXXXXXXXXXXXXX

AAAAAAAXXXBBBBBBBBBB
```

Examples of nucleic acid molecules of the invention which contain specific modifications include those with the following modifications, in which X represents an unmodified nucleotide, P represents 2'-O-propyl, M represents 2'-O-methyl, E represents 2'-O-ethyl, and F represents 2'-fluoro:

```
XXXXXXXXXXXXXXXXXXXXXXXX

PPMMXXXXXXXXXXXXXXXXXEEMMM

XXXXXXXXXXXXXXXXXXXXXXXX

EEEEXXXXXXXXXXXXXXXXXEEMMM

XXXXXXXXXXXXXXXXXXXXXXXX

PPEEXXXXXXXXXXXXXXXXXEEMMM

XXXXXXXXXXXXXXXXXXXXXXXX

EEEEEXXXXXXXXXXXXXXXXEEEEE

XXXXXXXXXXXXXXXXXXXXXXXX

PPPPPPPXXXXXXXXXXXXPPPPPPP

XXXXXXXXXXXXXXXXXXXXXXXX

FFPPPXXXXXXXXXXXXXXXXPPPFF

XXXXXXXXXXXXXXXXXXXXXXXX

MPPPPPPPPPPPPPPPXXXPPPPM

XXXXXXXXXXXXXXXXXXXXXXXX

FFFFFXXXXXXXXXXXXXXXXFFFFF

XXXXXXXXXXXXXXXXXXXXXXXX

PEEPEEMPXXXXXXXXXXPMEEPEEP

XXXXXXXXXXXXXXXXXXXXXXXX

MEXXXXXXXXXXXXXXMMMMMMMM

XXXXXXXXXXXXXXXXXXXXXXXX

MXXXXXXXXXXXXXXXXMMMMMMMM

XXXXXXXXXXXXXXXXXXXXXXXX

EEXXXXXXXXXXXXXXXXXEEEEEEEE
```

In some embodiments, the length of the sense strand can be 29, 28, 27, 26, 25, 24, 23, 22, 21, 20, 19, or 18 nucleotides. Similarly, the length of the antisense strand can be 29, 28, 27, 26, 25, 24, 23, 22, 21, 20, 19, or 18 nucleotides. Further, when a double-stranded nucleic acid molecule is formed from such sense and antisense molecules, the resulting duplex may have blunt ends or overhangs of 0, 1, 2, 3, 4, 5, 6, 7, 8, 9, 10, 11, 12, 13, or 14 nucleotides on one end or independently on each end. Further, double stranded nucleic acid molecules of the invention may be composed of a sense strand and an antisense strand wherein these strands are of lengths described above, and are of the same or different lengths, but share only 10, 11, 12, 13, 14, 15, 16, 17, 18, 19, or 20 nucleotides of sequence complementarity. By way of illustration, in a situation where the sense strand is 20 nucleotides in length and the antisense is 25 nucleotides in length and the two strands share only 15 nucleotides of sequence complementarity, a double stranded nucleic acid molecules may be formed with a 10 nucleotide overhang on one end and a 5 nucleotide overhang on the other end.

Double-stranded oligonucleotides of the invention include STEALTH™ RNAs which may be obtained from either Sequitur Inc. (Natick, Mass.), recently acquired by Invitrogen Corporation (Carlsbad, Calif.) or Invitrogen Corporation directly. STEALTH™ RNAs are often synthesized based upon nucleotide sequence information provided by purchasers. In particular instances, purchasers may provide the nucleotide sequence of an RNA transcript for which "knockdown" is desired and Invitrogen Corporation then selects suitable STEALTH™ RNA for the particular application or purchasers may provide the actual sequence of the STEALTH™ RNAs to be used in the "knockdown" process. Typically, in the second instance, the nucleotide sequences provided by purchasers are between 20 and 30 nucleotides in length. A more detailed description of business method aspects of the invention is set out elsewhere herein. However, these business methods typically include, in part, providing STEALTH™ RNA, as well as protocols and additional reagents and compounds for purchasers to use the purchased STEALTH™ RNA for knocking down gene expression.

As a further example, the use of 2'-O-methyl RNA may be used beneficially in circumstances in which it is desirable to minimize cellular stress responses. RNA having 2'-β-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This RNAi ("stealth RNA") is useful, for example, for avoiding the interferon or other cellular stress responses, both in short RNAi (e.g., siRNA) sequences that induce the interferon response, and in longer RNAi sequences that may induce the interferon response.

An especially advantageous use of the present invention is in gene function studies in which multiple RNAi sequences are used. According to present methods known in the art, frequently there is no way of predicting which nucleic acid sequences might induce a stress response, including the interferon response, and in this regard the present invention significantly advances the state of the art. For example, if all of the multiple sequences are partially 2'-β-methylated, the stress response, including interferon response, may be avoided, and thus avoid confounding results in which some sequences affect cellular phenotype independent of the target gene inhibition. Other chemical modifications in addition to 2'-O-methylation may also achieve this effect.

For example, modified sugars include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($-OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O$ $(CR'R'')_{0-3}H$, $(CR'R'')_{0-3}S(O)_{0-2}R'$, $(CR'R'')_{0-3}O$ $(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—$(PO_2^-)$—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47).

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—CH2-CH2-O-)phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, the sense strand of an oligonucleotide comprises a 5' group that allows for RNAi activity but which renders the sense strand inactive in terms of gene targeting. Preferably, such a 5' modifying group is a phosphate group or a group larger than a phosphate group. Oligonucleotides of this type often exhibit increased specificity for a target gene in a cell that corresponds to the nucleotide sequence of the antisense strand. This is because the sense strand in such an oligonucleotide is often rendered incapable of mediating cleavage of any nucleotide sequence it might bind to nonspecifically and thus will not inactivate any other genes in the cell. Thus, observed decrease in the expression of a gene within a cell transfected with such an oligonucleotide will often be attributed to the direct or indirect effect of the antisense strand. The term "specificity for a target gene," as used herein means the extent to which an effect of an oligonucleotide on a cell can be attributed directly or indirectly to the inhibition of expression of a target gene by an antisense nucleotide sequence present in said oligonucleotide.

Thus, according to another embodiment, the invention provides a method of increasing the specificity of an oligonucleotide for a target gene in a cell, wherein said oligonucleotide comprises a sense strand and an antisense strand, wherein both the sense strand and the antisense strand are capable of binding to corresponding nucleotide sequences if present in said cell, said method comprising the step of modifying the 5' terminal hydroxy moiety of said sense strand with a phosphate group or a group larger than a phosphate group prior to contacting said oligonucleotide with said cell so as to render said sense strand incapable of mediating cleavage of any nucleotide sequence it might bind to non-specifically and thus will not inactivate any other genes in the cell.

The invention also provides an improvement in a method of regulating the expression of a target gene in a cell, comprising contacting a cell with an oligonucleotide comprising a sense strand and an antisense strand, wherein both the sense strand and the antisense strand are capable of binding to corresponding nucleotide sequences if present in said cell, said improvement comprising the step of modifying the 5' terminal hydroxy moiety of said sense strand with a phosphate group or a group larger than a phosphate group prior to contacting said oligonucleotide with said cell so as to render said sense strand incapable of binding to corresponding nucleotide sequences if present in said cell.

In another embodiment, the antisense strand of an oligonucleotide comprises a 5' phosphate group or a group larger than a phosphate group. Oligonucleotides in accordance with this aspect of the invention which comprise such a modification of the antisense strand typically cannot inactivate a target gene that corresponds to the nucleotide sequence of said antisense strand. However, such modified oligonucleotides are extremely useful as controls for non-specific effects caused by a corresponding oligonucleotide that lacks such a 5' modification on the antisense strand. Non-specific effects include all effects on the cell by an oligonucleotide except those caused directly or indirectly by the inactivation of a target gene by a corresponding nucleotide sequence present in the antisense strand of said oligonucleotide.

Thus, according to a related embodiment, the invention provides a method of determining the non-specific effects of a test oligonucleotide transfected into a population of cells, wherein said test oligonucleotide comprises a sense strand, an antisense strand and at least one modified oligonucleotide, said method comprising the steps of: a) providing an oligonucleotide having the same nucleotide sequence and modifications as said test oligonucleotide and additionally comprising a 5' modification on the antisense strand, wherein said 5' modification is a phosphate group or a group larger than a phosphate group; b) transfecting said population of cells with the oligonucleotide provided in step a); and c) determining the effect of the oligonucleotide provided in step a) on said population of cells.

In particular embodiments, the invention comprises methods for measuring uptake of nucleic acid molecules (e.g., double-stranded nucleic acid molecules) by cells (e.g., eukaryotic cells). In particular embodiments, such methods comprise: (a) contacting a cell or population of cells (e.g., eukaryotic cells) with a detectably labeled nucleic acid molecule or a population of detectably labeled nucleic acid molecules (e.g., a mixture of detectably labeled nucleic acid molecules such as double-stranded nucleic acid molecules which differ in nucleotide sequence) under conditions which allow for some or all of the nucleic acid molecules to enter then cell or cells; (b) quantifying the amount of detectably labeled which has entered either (i) the cell or (ii) some or all of the cells of the population, for example by exposing the cells to one or more wavelengths of light which excite one or more label (e.g., one or more fluorescent label); and (c) measuring one or more signal (e.g., one or more fluorescent or other signal) generated from the label(s) in the cells. In more specific embodiments, the double-stranded nucleic acid molecule may contain one or more bound (e.g., covalently bound) label (e.g., one or more fluorescent label). In additional specific embodiments, the double-stranded nucleic acid molecule may be between 18 and 30, between 20 and 30, or between 22 and 30 nucleosides in length. Further, the double-stranded nucleic acid molecule may be 25 nucleosides in length.

The detectable label employed may be any suitable label known in the art and include radiolabels, chemiluminescent, and fluorescent labels. In many instances, the label will be of a type which does not substantially alter the uptake of the nucleic acid molecules to which they are attached by cells.

In particular embodiments, one or more label may be located on one or both 3' ends and/or on one or both 5' ends of the double-stranded nucleic acid molecules.

Additionally, the signal(s) generated by the label(s) may be measured by any number of ways, including visually (e.g., by microscopy) or fluorescent activated cell sorting (FACS). In any event, measurement of the signal(s) generated label(s) may be used to determine (a) the number or percentage of cells which have taken up the label(s), (b) the amount of one or more label taken up by individual cells or groups of cells, or (c) both (a) and (b).

Labels used in methods and compositions of the invention vary considerably but will often be labels which are readily detectable. Examples of such labels include the fluorescent labels FITC and 6-carboxyfluorescein.

Methods of the invention further include those where cells are contacted with one or more labels for a particular period of time (e.g., one hour, two hours, three hours, four hours, five hours, six hours, seven hours, eight hours, nine hours, ten hours, from about one hour to about ten hours, from about three hours to about eight hours, from about four hours to about seven hours, etc.) and then the cells are examined for the presence of the label.

The invention additionally includes methods for determining the ratio of viable to non-viable cells (e.g., eukaryotic cells) in populations of cells. In particular aspects, such methods include those which comprise (a) contacting cells of a population with a double-stranded nucleic acid molecule, (b) contacting the cells of the population of (a) with a dye which preferentially stains non-viable cells, and (c) comparing the number of stained cells to the number of unstained cells to arrive at the ratio of viable to non-viable cells in the population. In specific embodiments, step (b) above may performed, ten hours, twelve hours, twenty hours, twenty-four hours, thirty hours, forty hours, forty-eight hours, from about ten hours to about forty-eight hours, from about twelve hours to about twenty-four hours, or from about sixteen hours to about thirty hours after step (a).

According to another related embodiment, the invention provides a kit for determining the non-specific effect on a cell of a test oligonucleotide transfected into said cell, wherein said test oligonucleotide comprises a sense strand, an antisense strand and at least one modified oligonucleotide, said kit comprising a first vessel containing an oligonucleotide having the same nucleotide sequence and modifications as said test oligonucleotide and additionally comprising a 5' modification on said antisense strand, wherein said 5' modification is a phosphate group or a group larger than a phosphate group; and instructions for using said 5'-modified oligonucleotide to determine the non-specific effect on said cell of said test oligonucleotide transfected into said cell. In a preferred embodiment, the kit additionally comprises one or more of the following: an independent vessel containing a dye which distinguishes live cells from dead cells in said cell population; an independent vessel comprising an oligonucleotide known to inhibit a gene expressed in said cell population; an independent vessel containing said test oligonucleotide; and an independent vessel comprising an oligonucleotide having the same nucleotide sequence and modifications as said test oligonucleotide and additionally comprising a 5' detectable end blocking group on the sense strand.

In yet another embodiment, the invention provides an oligonucleotide of the invention that comprises at least one modified RNA nucleotide and a detectable moiety on one or both of the sense strand and the antisense strand. The term "detectable moiety", as used herein, refers to a chemical moiety that renders the oligonucleotide detectable (e.g., visibly detectable) within a cell. In many instances, the detectable moiety is a fluorescent molecule. In some instances, the detectable moiety is a fluorescent or chemiluminescent fluorophore. In particular instances, the detectable moiety is FITC. In another instance, the detectable moiety is a 5'- or 3'-end blocking group located on one or both of the sense and the antisense strand. In one instance, at least one RNA nucleotide in this oligonucleotide contains at least one chemical modification. These modified RNA nucleotides may contain one or more 2'-fluoro, 2'-O-methyl, 2'-O-ethyl, and/or 2'-O-propyl groups. In particular instances, (1) all of the nucleotides of the antisense strand and/or the sense strand contain 2'-fluoro, 2'-O-methyl, 2'-O-ethyl, and/or 2'-O-propyl groups and (2) the antisense and/or the sense strand contains FITC as a 3'- and/or 5'-end blocking group. In particular embodiments, the entire sense strand is 2'-fluoroated, 2'-O-methylated, 2'-O-ethylated, or 2'-O-propylated and both the sense and antisense strands contain FITC as a 3'- or 5'-end blocking group.

Oligonucleotides of the invention that comprise a detectable moiety can serve as a control for the uptake of corresponding oligonucleotides having the same nucleotide sequence (with or without some or all of the modifications on the nucleotides present in the blocked oligonucleotide), but lacking the detectable moiety. Oligonucleotides comprising a detectable moiety are particularly useful in establishing optimal transfection conditions for cells that will be treated with the corresponding unblocked or undetectable oligonucleotide. When a detectable moiety present on the antisense strand which corresponds to a target gene is a 5'-end blocking group, that antisense strand is incapable of inhibiting the expression of that target gene. If the detectable moiety is present elsewhere on the antisense strand and/or anywhere on the sense strand, the oligonucleotide may still be capable of inhibiting expression of the target gene, as well as being detected. An oligonucleotide capable of inhibiting expression of a target gene is referred to as an "active oligonucleotide." The invention includes active oligonucleotides and compositions comprising such active oligonucleotides.

Some detectable moiety-containing oligonucleotides of the invention can be detected in a cell nucleus for at least 72 hours following transfection. Moreover, oligonucleotides comprising a detectable moiety, when used in parallel with a corresponding active oligonucleotide (or, alternatively, if the oligonucleotide comprising a detectable moiety is itself active), provide the best control for any variation in transfection conditions and reagents on the day that transfection is performed. Also, the persistence of these detectable oligonucleotides in the cell is typically highly correlated with siRNA activity of a corresponding active oligonucleotide.

Thus, according to a related embodiment, the invention provides a method of determining the uptake of a test oligonucleotide by a population of cells using a transfection protocol, wherein the test oligonucleotide comprises a sense strand, an antisense strand and at least one modified oligonucleotide, the method comprising the steps of: a) providing an oligonucleotide having (i) the same nucleotide sequence as the test oligonucleotide, (ii) the same number of and/or type of modifications, a different number of and/or type of modifications, or no modifications, and (iii) a detectable moiety on one or both of the sense and antisense strands; b) using the transfection protocol to transfect said population of cells with the oligonucleotide provided in step a); and c) using detecting means to determine the number of cells in said population transfected with oligonucleotide provided in step a). In one embodiment, the test oligonucleotide additionally comprises a detectable moiety, is an active oligonucleotide and is the oligonucleotide provided in step a).

The term "detecting means," as used herein, encompasses any method of detection that would allow one to quantitatively or qualitatively the presence of the oligonucleotide comprising a detectable moiety within a cell. For example, if the detectable moiety is a fluorescent label, then detecting means would comprise the use of light source having a wavelength to cause excitation of said fluorescent label and either a fluorescent microscope fitted with a filter appropriate to observe the emission from said excited fluorescent label or a fluorescence activated cell sorter.

According to another related embodiment, the invention provides a kit for optimizing the uptake of a test oligonucleotide by a population of cells, wherein said test oligonucleotide comprises a sense strand, an antisense strand and at least one modified oligonucleotide, said kit comprising a first vessel containing an oligonucleotide having the same nucleotide sequence and modifications as said test oligonucleotide and additionally comprising a detectable moiety on one or both of said sense and antisense strands and instructions for using said detectable moiety-containing oligonucleotide to determine uptake of said test oligonucleotide by said population of cells. In a preferred embodiment, the kit additionally comprises one or more of the following: an independent vessel containing a dye which distinguishes live cells from dead cells in said cell population; an independent vessel comprising an oligonucleotide known to inhibit a gene expressed in said cell population; an independent vessel containing said test oligonucleotide; and an independent vessel containing an oligonucleotide having the same nucleotide sequence and modifications as said test oligonucleotide and additionally comprising a 5' modification on the antisense strand, wherein said 5' modification is a phosphate group or a group larger than a phosphate group, and said 5' modification inactivates said oligonucleotide.

In each of the kit embodiments, the detectable moiety is preferably FITC. In kit embodiments that include an independent vessel containing a dye that distinguishes live cells from dead cells in said cell population, the dye is preferably dead red stain (Molecular Probes, Eugene Oreg., ethidium homodimer cat. no. E-1169).

In one embodiment, the oligonucleotides included in the composition are high affinity oligonucleotides. The term "high affinity" as used herein includes oligonucleotides that have a Tm (melting temperature) of or greater than about 60° C., greater than about 65° C., greater than about 70° C., greater than about 75° C., greater than about 80° C. or greater than about 85° C. The Tm is the midpoint of the temperature range over which the oligonucleotide separates from the target nucleotide sequence. At this temperature, 50% helical (hybridized) versus coil (unhybridized) forms are present. Tm is measured by using the UV spectrum to determine the formation and breakdown (melting) of hybridization. Base stacking occurs during hybridization, which leads to a reduction in UV absorption. Tm depends both on GC content of the two nucleic acid molecules and on the degree of sequence complementarity. Tm can be determined using techniques that are known in the art (see for example, Monia et al. 1993. *J. Biol. Chem.* 268:145; Chiang et al. 1991. *J. Biol. Chem.* 266:18162; Gagnor et al. 1987. *Nucleic Acids Res.* 15:10419; Monia et al. 1996. *Proc. Natl. Acad. Sci.* 93:15481; Publisis and Tinoco. 1989. *Methods in Enzymology* 180:304; Thuong et al. 1987. *Proc. Natl. Acad. Sci. USA* 84:5129).

In one embodiment, an oligonucleotide can include an agent which increases the affinity of the oligonucleotide for its target sequence. The term "affinity enhancing agent" includes agents that increase the affinity of an oligonucleotide for its target. Such agents include, e.g., intercalating agents and high affinity nucleomonomers. Intercalating agents interact strongly and nonspecifically with nucleic acids. Intercalating agents serve to stabilize RNA-DNA duplexes and thus increase the affinity of the oligonucleotides for their targets. Intercalating agents are most commonly linked to the 3' or 5' end of oligonucleotides. Examples of intercalating agents include acridine, chlorambucil, benzopyridoquinoxaline, benzopyridoindole, benzophenanthridine, and phenazinium. The agents may also impart other characteristics to the oligonucleotide, for example, increasing resistance to endonucleases and exonucleases.

Figure 6:
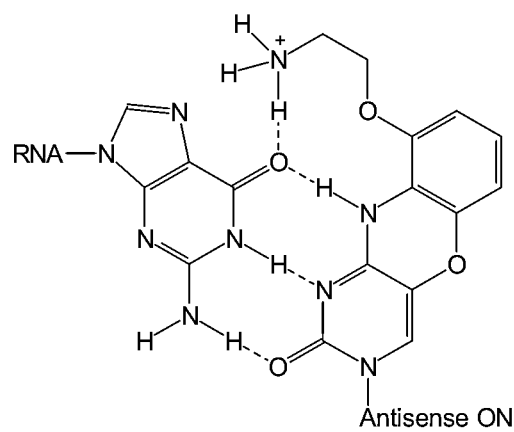

In one embodiment, a high affinity nucleomonomer is incorporated into an oligonucleotide. The language "high affinity nucleomonomer" as used herein includes modified bases or base analogs that bind to a complementary base in a target nucleic acid molecule with higher affinity than an unmodified base, for example, by having more energetically favorable interactions with the complementary base, e.g., by forming more hydrogen bonds with the complementary base. For example, high affinity nucleomonomer analogs such as aminoethoxy phenoxazine (also referred to as a G clamp), which forms four hydrogen bonds with guanine are included in the term "high affinity nucleomonomer." A high affinity nucleomonomer is illustrated in FIG. 6 (see, e.g., Flanagan, et al., 1999. *Proc. Natl. Acad. Sci.* 96:3513).

Other exemplary high affinity nucleomonomers are known in the art and include 7-alkenyl, 7-alkynyl, 7-heteroaromatic-, or 7-alkynyl-heteroaromatic-substituted bases or the like which can be substituted for adenosine or guanosine in oligonucleotides (see, e.g., U.S. Pat. No. 5,594, 121). Also, 7-substituted deazapurines have been found to impart enhanced binding properties to oligonucleotides, i.e., by allowing them to bind with higher affinity to complementary target nucleic acid molecules as compared to unmodified oligonucleotides. High affinity nucleomonomers can be incorporated into the oligonucleotides of the instant invention using standard techniques.

In another embodiment, an agent that increases the affinity of an oligonucleotide for its target comprises an intercalating agent. As used herein, the language "intercalating agent" includes agents which can bind to a DNA double helix. When covalently attached to an oligonucleotide of the invention, an intercalating agent enhances the binding of the oligonucleotide to its complementary genomic DNA target sequence. The intercalating agent may also increase resistance to endonucleases and exonucleases.

Exemplary intercalating agents are taught by Helene and Thuong (1989. *Genome* 31:413), and include e.g., acridine derivatives (Lacoste et al. 1997. *Nucleic Acids Research.* 25:1991; Kukreti et al. 1997. *Nucleic Acids Research.* 25:4264); quinoline derivatives (Wilson et al. 1993. *Biochemistry* 32:10614); and benzo[f]quino[3,4-b]quinoxaline derivatives (Marchand et al. 1996. *Biochemistry.* 35:5022; Escude et al. 1998. *Proc. Natl. Acad. Sci.* 95:3591).

Intercalating agents can be incorporated into an oligonucleotide using any convenient linkage. For example, acridine or psoralen can be linked to the oligonucleotide through any available —OH or —SH group, e.g., at the terminal 5' position of the oligonucleotide, the 2' positions of sugar moieties, or an OH, $NH_2$, COOH, or SH incorporated into the 5-position of pyrimidines using standard methods.

In one embodiment, when included in an RNase H activating antisense nucleotide sequence, an agent that increases the affinity of an oligonucleotide for its target is not positioned adjacent to an RNase activating region of the oligonucleotide, e.g., is positioned adjacent to a non-RNase activating region. Preferably, the agent that increases the affinity of an oligonucleotide for its target is placed at a distance as far as possible from the RNase activating domain of the chimeric antisense sequence such that the specificity of the chimeric antisense sequence is not altered when compared with the specificity of a chimeric antisense sequence which lacks the intercalating compound. In one embodiment, this can be accomplished by positioning the agent adjacent to a non-RNase activating region. The specificity of the oligonucleotide can be tested by demonstrating that transcription of a non-target sequence, preferably a non-target sequence which is structurally similar to the target (e.g., has some sequence homology or identity with the target sequence but which is not identical in sequence to the target), is not inhibited to a greater degree by an oligonucleotide comprising an affinity enhancing agent than by an oligonucleotide directed against the same target that does not comprise an affinity enhancing agent.

Double-stranded oligonucleotides of the invention may be formed by a single, self-complementary nucleic acid strand or two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence.

Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

When comprised of two separate complementary nucleic acid molecules, the individual nucleic acid molecules can be of different lengths.

In one embodiment, a double-stranded oligonucleotide of the invention is double-stranded over its entire length, i.e., with no overhanging single-stranded sequence at either end of the molecule, i.e., is blunt-ended. In another embodiment, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide.

In one embodiment, the double-stranded duplex constructs of the invention can be further stabilized against nucleases by forming loop structures at the 5' or 3' end of the sense or antisense strand of the construct. For example, the construct can take the form shown in FIG. 1, where the Ns are nucleomonomers in complementary oligonucleotide strands (i.e., the top N strand is complementary to the bottom N strand) of equal length (e.g., between about 12 and about 40 nucleotides in length) and X and Y are each independently selected from a group consisting of nothing (i.e., the construct is a blunt ended construct with no loops and no overhang); from about 1 to about 20 nucleotides of 5' overhang; from about 1 to about 20 nucleotides of 3' overhang; a GAAA loop (tetra-loop); and a loop consisting from about 4 to about 20 nucleomonomers (where the nucleomonomers are all either G's or A's).

The sequence of Ns corresponds to the target gene sequence (e.g., is homologous or identical to a nucleotide sequence that is sense or antisense to the target gene sequence), while the nucleotide sequence of the loop structure does not correspond to the target gene sequence.

For example, such loops can comprise all G's and A's and be from about 4 to about 20 nucleotides in length. In one embodiment, such a loop can be a tetra-loop having a sequence GAAA as depicted in FIG. 7.

In one embodiment, the number of Ns is about 27.

In embodiments in which loops are at one or both ends of the construct, the oligonucleotide can be divided by having a "nick" which is two non-linked nucleomonomers at any point along the sense or antisense strand, but preferably along the sense strand. Preferably, the nick is at least four bases from the nearest end of the duplexed region (to provide enough thermodynamic stability).

In another embodiment, a construct of the invention can take the form depicted in FIG. 8, where the Ns are complementary nucleomonomers in oligonucleotide strands of equal length (e.g., between 12-40 nucleomonomers in length); Zs are nucleomonomers in complementary oligonucleotide strands of between about 2 and about 8 nucleomonomers in length and which comprise a sequence which can optionally correspond to the target sequence; and where Ms are nucleomonomers in complementary oligonucleotide strands of between about 2 and about 8 nucleomonomers in length and which can optionally correspond to the target sequence.

Preferably, the Zs and Ms are nucleomonomers selected from the group consisting of C's and G's to make the end of the duplex more thermodynamically stable. Ends of duplexes can become single stranded transiently, and since duplex RNA is more stable than single-stranded RNA, the enhanced stability of the duplex on the ends will result in higher nuclease stability.

A preferred sequence for Z or M in the antisense strand is from 2-8 nucleomonomers in length or preferably from 3-4 nucleomonomers in length, e.g., (from 5' to 3') CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC, or CCGG. The complementary strand would have the corresponding complementary sequence.

Figure 3:
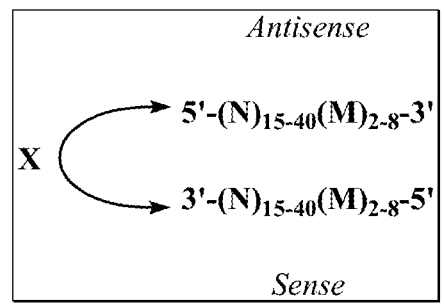
FIG. 3 A depiction of an exemplary composition.

In still another embodiment, a construct of the invention has the form depicted in FIG. 3, where Ns are nucleomonomers in complementary oligonucleotide strands (i.e., the top N strand is complementary to the bottom N strand) of equal length (e.g., from between about 12 to about 40 nucleomonomers in length) and X is selected from the group consisting of nothing (i.e., leaving blunt ends with no loop or overhang); 1-20 nucleotides of 5' overhang; 1-20 nucleotides of 3' overhang; a GAAA loop (tetra-loop); and a loop consisting of from about 4 to about 20 nucleomonomers (where the nucleomonomers are all either G's or A's) and where Ms are nucleomonomers in complementary oligonucleotide strands of between about 2 and about 8 nucleomonomers in length (which can optionally correspond to the target sequence). Preferably, Ms are nucleomonomers selected from the group consisting of contain C's and G's.

A preferred sequence for M in the antisense strand is from 2-8 nucleomonomers in length or preferably from 3-4 nucleomonomers in length, e.g., (from 5' to 3') CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC, or CCGG and the corresponding complement on the opposite strand.

Figure 4:
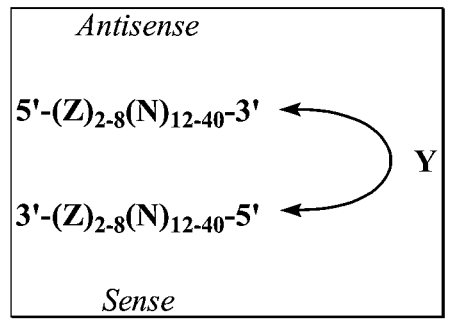
FIG. 4 A depiction of an exemplary composition.

In another embodiment, the construct can take the form depicted in FIG. 4, where Ns are nucleomonomers in complementary oligonucleotide strands of equal length (e.g., from between about 12 to about 40 nucleomonomers in length) and Y is selected from the group consisting of nothing (i.e., leaving blunt ends with no loop or overhang; 1-20 nucleotides of 5' overhang; 1-20 nucleotides of 3' overhang; a GAAA loop (tetra-loop); and a loop consisting of a sequence of from about 4 to about 20 nucleomonomers (where the nucleomonomers are all either Gs or A's) and where Zs are nucleomonomers in complementary oligonucleotide strands of between about 2 and about 8 nucleomonomers in length and which comprise a sequence which can optionally correspond to the target sequence. Preferably, the Zs are nucleomonomers selected from the group consisting of Cs and Gs to make the end of the duplex more stable.

A preferred sequence for Z in the antisense strand is from 2-8 nucleomonomers in length or preferably from 3-4 nucleomonomers in length, e.g., (from 5' to 3') CC, GG, CG, GC, CCC, GGG, CGG, GCC, GCG, CGC, CGGG, GCCC, CCCC, GGGG, GCGC, CGCG, GGGC, CCCG, CGGG, GCCC, GGCC or CCGG (and the corresponding complement on the opposite strand). For example, in the structure shown in FIG. 9, GGCC on the end (and its complement) confers additional stability.

The invention also relates to a double-stranded oligonucleotide composition having the following structure depicted in FIG. 10, wherein (1) oligoA is an oligonucleotide of a number of nucleomonomers; (2) oligoB is an oligonucleotide that has the same number of nucleomonomers as oligoA and that is complementary to oligoA; (3) either oligoA or oligoB corresponds to a target gene sequence.

In this structure, X may be selected from (a) nothing; (b) an oligonucleotide of about 1 to about 20 nucleotides covalently bonded to the 5' end of oligoA and constituting a 5' overhang; (c) an oligonucleotide of about 1 to about 20 nucleotides covalently bonded to the 3' end of oligoB and constituting a 3' overhang; (d) and an oligonucleotide of about 4 to about 20 nucleomonomers covalently bonded to the 3' end of oligoB and the 5' end of oligoA and constituting a loop structure, where the nucleomonomers are selected from the group consisting of G and A.

Similarly, Y may be selected from (a) nothing; (b) an oligonucleotide of about 1 to about 20 nucleotides covalently bonded to the 5' end of oligoB and constituting a 5' overhang; (c) an oligonucleotide of about 1 to about 20 nucleotides covalently bonded to the 3' end of oligoA and constituting a 3' overhang; (d) and an oligonucleotide of about 4 to about 20 nucleomonomers covalently bonded to the 3' end of oligoA and the 5' end of oligoB and constituting a loop structure, where the nucleomonomers are selected from the group consisting of G and A.

Figure 11:
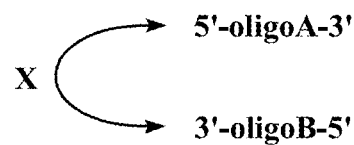
FIG. 11 A depiction of an exemplary composition.

Similarly, the invention includes a double-stranded oligonucleotide composition having the structure depicted in FIG. 11, wherein (1) oligoA is 5'-(N)$_{15-40}$-(M)$_{2-8}$-3' and oligoB is 5'-(N)$_{15-40}$-(M)$_{2-8}$-3', wherein each of N and M is independently a nucleomonomer; (2) both of the sequences of Ns are complementary oligonucleotide strands of equal length having between about 15 and 40 nucleomonomers; (3) at least one of the sequences of Ns, optionally with some or all of the flanking Ms, corresponds to a target gene sequence. Both of the sequences of Ms are complementary oligonucleotide strands of between about 2 and about 8 nucleomonomers in length. The two M strands are optionally of the same length.

The group X indicated by the curved line is selected from (a) nothing; (b) an oligonucleotide of about 1 to about 20 nucleotides covalently bonded to the 5' end of oligoA and constituting a 5' overhang; (c) an oligonucleotide of about 1 to about 20 nucleotides covalently bonded to the 3' end of oligoB and constituting a 3' overhang; (d) and an oligonucleotide of about 4 to about 20 nucleomonomers covalently bonded to the 3' end of oligoB and the 5' end of oligoA and constituting a loop structure, where the nucleomonomers are selected from the group consisting of G and A.

Figure 12:
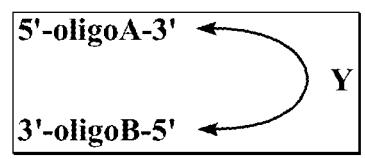
FIG. 12 A depiction of an exemplary composition.

Likewise, the invention pertains to a double-stranded oligonucleotide composition having the structure depicted in FIG. 12, wherein (1) oligoA is 5'-(Z)$_{2-8}$—(N)$_{12-40}$-3' and oligoB is 5'-(Z)$_{2-8}$—(N)$_{12-40}$-3', wherein each of N and Z is independently a nucleomonomer; (2) both of the sequences of Ns are complementary oligonucleotide strands of equal length having between about 12 and 40 nucleomonomers; (3) at least one of the sequences of Ns, optionally with some or all of the flanking Zs, corresponds to a target gene sequence. Both of the sequences of Zs are complementary oligonucleotide strands of between about 2 and about 8 nucleomonomers in length. The two Z strands are optionally of the same length.

Here, Y is selected from (a) nothing; (b) an oligonucleotide of about 1 to about 20 nucleotides covalently bonded to the 5' end of oligoB and constituting a 5' overhang; (c) an oligonucleotide of about 1 to about 20 nucleotides covalently bonded to the 3' end of oligoA and constituting a 3' overhang; (d) and an oligonucleotide of about 4 to about 20 nucleomonomers covalently bonded to the 3' end of oligoA and the 5' end of oligoB and constituting a loop structure, where the nucleomonomers are selected from the group consisting of G and A.

In one embodiment, the double-stranded duplex of an oligonucleotide of the invention is from between about 12 to about 50 nucleomonomers in length, i.e., the number of nucleotides of the double-stranded oligonucleotide which hybridize to the complementary sequence of the double-stranded oligonucleotide to form the double-stranded duplex structure is from about 12 to about 50 nucleomonomers in length. In another embodiment, the double-stranded duplex of an oligonucleotide of the invention is from between about 12 to about 40 nucleomonomers in length.

In one embodiment, the double-stranded duplex of an oligonucleotide of the invention is at least about 25 nucleomonomers in length. In one embodiment, the double-stranded duplex is greater than about 25 nucleomonomers in length. In one embodiment, a double-stranded duplex is at least about 26, 27, 28, 29, 30, at least about 40, at least about 50, at least about 60, at least about 70, at least about 80, or at least about 90 nucleomonomers in length. In another embodiment, the double-stranded duplex is less than about 25 nucleomonomers in length. In one embodiment, a double-stranded duplex is at least about 10, at least about 15, at least about 20, at least about 22, at least about 23 or at least about 24 nucleomonomers in length.

In one embodiment, the number of Ns in each strand of the duplex is about 12, 13, 14, 15, 16, 17, 18, 19, 20, 21, 22, 23, 24, 25, 26, or 27. In another embodiment, the number of Ns in each strand of the duplex is about 30, 35, 40, 45, or 50. In one embodiment, the number of Ns in each strand of the duplex is about 19. In a preferred embodiment, the number of Ns in each strand of the duplex is about 27. In another embodiment, the number of Ns in each strand of the duplex is about 27 (e.g., is 26, 27, or 28). In another embodiment, the number of Ns in each strand of the duplex is 27.

In one embodiment, an individual nucleic acid molecule of a double-stranded oligonucleotide of the invention is at least about 25 nucleomonomers in length. For example, when the double-stranded oligonucleotide of the invention is comprised of one nucleic acid molecule, that individual molecule is at least about 25 nucleomonomers in length or when the double-stranded oligonucleotide of the invention is comprised of two separate nucleic acid molecules, the length of at least one of the individual nucleic acid molecules is at least about 25 nucleomonomers in length.

A variety of nucleotides of different lengths may be used. In one embodiment, an individual nucleic acid molecule comprising a double-stranded oligonucleotide of the invention is greater than about 25 nucleomonomers in length. In one embodiment, an individual nucleic acid molecule comprising a double-stranded oligonucleotide of the invention is at least about 26, 27, 28, 29, 30, at least about 40, at least about 50, or at least about 60, at least about 70, at least about 80, or at least about 90 nucleomonomers in length. In another embodiment, an individual nucleic acid molecule comprising a double-stranded oligonucleotide of the invention is less than about 25 nucleomonomers in length. In one embodiment, an individual nucleic acid molecule comprising a double-stranded oligonucleotide of the invention is at least about 10, at least about 15, at least about 20, at least about 22, at least about 23 or at least about 24 nucleomonomers in length.

Double-stranded molecules of the invention may comprise a first nucleotide sequence which is antisense to at least part of the target gene and a second nucleotide sequence which is complementary to the first nucleotide sequence; i.e., is sense to at least part of the target gene. In one embodiment, the second nucleotide sequence of the double-stranded molecule comprises a nucleotide sequence which is at least about 100% complementary to the antisense molecule.

In another embodiment, the second nucleotide sequence of double-stranded molecules of the invention may comprise a nucleotide sequence which is at least about 95% complementary to the antisense molecule. In another embodiment, the second nucleotide sequence of double-stranded molecules of the invention may comprise a nucleotide sequence which is at least about 90% complementary to the antisense molecule. In another embodiment, the second nucleotide sequence of double-stranded molecules of the invention may comprise a nucleotide sequence which is at least about 80% complementary to the antisense molecule. In another embodiment, the second nucleotide sequence of double-stranded molecules of the invention may comprises a nucleotide sequence which is at least about 60% complementary to the antisense molecule. In another embodiment, the second nucleotide sequence of double-stranded molecules of the invention may comprise a nucleotide sequence which is at least about 100% complementary to the antisense molecule.

To determine the percent identity of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. The percent complementarity can be determined analogously; when a position in one sequence occupied by a nucleotide that is complementary to the nucleotide in the other sequence, then the molecules are complementary at that position.

The comparison of sequences and determination of percent identity between two sequences can be accomplished using a mathematical algorithm. In a preferred embodiment, the percent identity between two nucleotide sequences is determined using e.g., the GAP program in the GCG software package, using a NWSgapdna. CMP matrix and a gap weight of 40, 50, 60, 70, or 80 and a length weight of 1, 2, 3, 4, 5, or 6. In another embodiment, the percent identity between two nucleotide sequences is determined using the algorithm of E. Meyers and W. Miller (*Comput. Appl. Biosci.* 4:11-17 (1988)) which has been incorporated into the ALIGN program (version 2.0), using a PAM 120 weight residue table, a gap length penalty of 12 and a gap penalty of 4.

The nucleic acid sequences of the present invention can further be used as a "query sequence" to perform alignments against sequences in public databases. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See, e.g., the NIH website.

In yet another embodiment, a first antisense sequence of the double-stranded molecule hybridizes to its complementary second sequence of the double-stranded molecule under stringent hybridization conditions. As used herein, the term "hybridizes under stringent conditions" is intended to describe conditions for hybridization and washing under which nucleotide sequences at least 60% complementary to each other typically remain hybridized to each other. Preferably, the conditions are such that sequences at least about 70%, more preferably at least about 80%, even more preferably at least about 85% or 90% complementary to each other typically remain hybridized to each other.

Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Ranges intermediate to the above-recited values, e.g., at 60-65° C. or at 55-60° C. are also intended to be encompassed by the present invention. Alternatively, formamide can be included in the hybridization solution, using methods and conditions also known in the art.

One of the sequences (or molecules) of the double-stranded oligonucleotide of the invention is antisense to the target gene. As used herein, the term "antisense sequence" includes nucleotide sequences which bind to the "sense" strand of the nucleotide sequence of the target gene (e.g., polynucleotides such as DNA, mRNA (including pre-mRNA) molecules). When the antisense sequences of the invention bind to nucleic acid molecules, they can bind to any region of a nucleic acid molecule, including e.g., introns, exons, 5', or 3' untranslated regions. Antisense sequences that work by binding to a target and activating RNase H preferably bind within an intron, an exon, the 5' untranslated region, or the 3' untranslated region of a nucleic acid target molecule.

Preferably, the oligonucleotide compositions of the invention do not activate the interferon pathway, e.g., as evidenced by the lack of induction of the double-stranded RNA, interferon-inducible protein kinase, PKR.

In one embodiment, modifications are made to a double-stranded RNA molecule which would normally activate the interferon pathway such that the interferon pathway is not activated. For example, the interferon pathway is activated by double-stranded unmodified RNA. The cellular recognition of double-stranded RNA is highly specific and modifying one or both of the strands of a double-stranded duplex enables the double-stranded RNA molecule to evade the double-stranded RNA recognition machinery of the cell but would still allow for the activation of the RNAi pathway.

The ability of a double-stranded oligonucleotide to activate interferon could be assessed by testing for expression of the double-stranded RNA, Interferon-Inducible Protein Kinase, PKR using techniques known in the art and also testing for the ability of the double-stranded molecule to effect target gene inhibition. Accordingly, in one embodiment, the invention provides a method of testing for the ability of a double-stranded RNA molecule to induce interferon by testing for the ability of the oligonucleotide to activate PKR. Compositions that do not activate PKR (i.e., do not activate the interferon pathway) are then selected for use to inhibit gene transcription in cells, e.g., in therapeutics or functional genomics.

Without being limited to any particular mechanism of action, an antisense sequence used in a double-stranded oligonucleotide composition of the invention that can specifically hybridize with a nucleotide sequence within the target gene (i.e., can be complementary to a nucleotide sequence within the target gene) may achieve its affects based on, e.g.: (1) binding to target mRNA and sterically blocking the ribosome complex from translating the mRNA; (2) binding to target mRNA and triggering mRNA cleavage by RNase H; (3) binding to double-stranded DNA in the nucleus and forming a triple helix; (4) hybridizing to open DNA loops created by RNA polymerase; (5) interfering with mRNA splicing; (6) interfering with transport of mRNA from the nucleus to the cytoplasm; or (7) interfering with translation through inhibition of the binding of initiation factors or assembly of ribosomal subunits (i.e., at the start codon).

In one embodiment, an antisense sequence of the double-stranded oligonucleotides of the invention is complementary to a target nucleic acid sequence over at least about 80% of the length of the antisense sequence. In another embodiment, the antisense sequence of the double-stranded oligonucleotide of the invention is complementary to a target nucleic acid sequence over at least about 90-95% of the length of the antisense sequence. In another embodiment, the antisense sequence of the double-stranded oligonucleotide of the invention is complementary to a target nucleic acid sequence over the entire length of the antisense sequence.

In yet another embodiment, an antisense sequence of the double-stranded oligonucleotide hybridizes to at least a portion of the target gene under stringent hybridization conditions.

In one embodiment, antisense sequences of the invention are substantially complementary to a target nucleic acid sequence. In one embodiment, an antisense RNA molecule comprises a nucleotide sequence which is at least about 100% complementary to a portion of the target gene. In another embodiment, an antisense RNA molecule comprises a nucleotide sequence which is at least about 90% complementary to a portion of the target gene. In another embodiment, an antisense RNA molecule comprises a nucleotide sequence which is at least about 80% complementary to a portion of the target gene. In another embodiment, an antisense RNA molecule comprises a nucleotide sequence which is at least about 60% complementary to a portion of the target gene. In another embodiment, an antisense RNA molecule comprises a nucleotide sequence which is at least about 100% complementary to a portion of the target gene. Preferably, no loops greater than about 8 nucleotides are formed by areas of non-complementarity between the oligonucleotide and the target.

In one embodiment, an antisense nucleotide sequence of the invention is complementary to a target nucleic acid sequence over at least about 80% of the length of the antisense sequence. In another embodiment, an antisense sequence of the invention is complementary to a target nucleic acid sequence over at least about 90-95% of the length of the antisense sequence. In another embodiment, an antisense sequence of the invention is complementary to a target nucleic acid sequence over the entire length of the antisense sequence.

The antisense sequences used in an oligonucleotide composition of the invention may be of any type, e.g., including morpholino oligonucleotides, RNase H activating oligonucleotides, or ribozymes.

In one embodiment, a double-stranded oligonucleotide of the invention can comprise (i.e., be a duplex of) one nucleic acid molecule which is DNA and one nucleic acid molecule which is RNA.

Antisense sequences of the invention can be "chimeric oligonucleotides" which comprise an RNA-like and a DNA-like region. The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

In one embodiment, the contiguous nucleomonomers are linked by a substitute linkage, e.g., a phosphorothioate linkage. In one embodiment, an antisense sequence of the invention is unstable, i.e., is degraded in a cell, in the absence of the second strand (or self complementary sequence) which forms a double-stranded oligonucleotide of the invention. For example, in one embodiment, a chimeric antisense sequence comprises unmodified DNA nucleomonomers in the gap rather than phosphorothioate DNA.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

Figure 13:
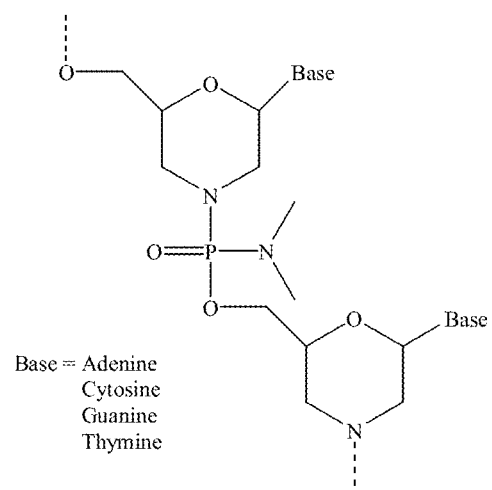
FIG. 13 A depiction of an exemplary 2 subunit morpholino oligonucleotide.

Antisense sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. An example of a 2 subunit morpholino oligonucleotide is shown in FIG. 13.

Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl.

Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research*. 21:3567). Enhanced delivery of oligonucleotides can also be mediated by the use of vectors (See e.g., Shi, Y. 2003. Trends Genet. 2003 Jan. 19:9; Reichhart J M et al. Genesis. 2002. 34(1-2):160-4, Yu et al. 2002. Proc. Natl. Acad. Sci. USA 99:6047; Sui et al. 2002. Proc. Natl. Acad. Sci. USA 99:5515) viruses, polyamine or polycation conjugates using compounds such as polylysine, protamine, or N1, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown. Examples of different protocols for different cell types are set forth in the Examples section.

Employing a 1 milliliter final volume solely as a reference volume, exemplary amounts of reagents which may be used to transfect cells with nucleic acid molecules of the invention (e.g., double-stranded oligonucleotides such as, for example, STEALTH™ RNA) include the following. For nucleic acid molecules of the invention (e.g., STEALTH™ RNA), the amount present may be between about 0.1 picomoles and about 900 nanomoles, between about 0.1 picomoles and about 700 nanomoles, between about 0.1 picomoles and about 500 nanomoles, between about 0.1 picomoles and about 300 nanomoles, between about 0.1 picomoles and about 200 nanomoles, between about 0.1 picomoles and about 100 nanomoles, between about 0.1 picomoles and about 50 nanomoles, between about 0.1 picomoles and about 25 nanomoles, between about 0.1 picomoles and about 1.0 nanomole, between about 0.1 picomoles and about 800 picomoles, between about 0.1 picomoles and about 600 picomoles, between about 0.1 picomoles and about 500 picomoles, between about 0.1 picomoles and about 300 picomoles, between about 0.1 picomoles and about 200 picomoles, between about 1 picomole and about 900 nanomoles, between about 1 and about 600 picomoles, between about 1 and about 500 picomoles, between about 1 and about 400 picomoles, between about 100 and about 800 picomoles, between about 200 and about 800 picomoles, between about 300 and about 800 picomoles, between about 400 and about 800 picomoles, between about 200 and about 700 picomoles, between about 50 and about 800 picomoles, between about 50 and about 500 picomoles, between about 50 and about 400 picomoles, between about 50 and about 300 picomoles, between about 50 and about 200 picomoles, between about 100 and about 200 picomoles, between about 100 and about 300 picomoles, between about 1 nanomole and about 800 nanomoles, between about 100 nanomoles and about 800 nanomoles, between about 100 nanomoles and about 900 nanomoles, between about 200 nanomoles and about 900 nanomoles, between about 300 nanomoles and about 900 nanomoles, between about 400 nanomoles and about 900 nanomoles, or between about 500 nanomoles and about 900 nanomoles.

Further, the total number of cells present may be between about $1.0 \times 10^3$ and about $1.0 \times 10^6$, between about $4.0 \times 10^3$ and about $1.0 \times 10^6$, between about $5.0 \times 10^3$ and about $1.0 \times 10^6$, between about $8.0 \times 10^3$ and about $1.0 \times 10^6$, between about $9.0 \times 10^3$ and about $5.0 \times 10^5$, between about $1.0 \times 10^3$ and about $1.0 \times 10^5$, between about $5.0 \times 10^4$ and about $1.0 \times 10^4$, between about $4.0 \times 10^3$ and about $5.0 \times 10^5$, or between about $1.0 \times 10^4$ and about $1.0 \times 10^5$.

The amount of LIPOFECTAMINE™ 2000 or OLIGOFECTAMINE™, when present as a transfection reagent may be between 0.5 nanoliters and 100 microliters, between 5 nanoliters and 100 microliters, between 50 nanoliters and 100 microliters, between 100 nanoliters and 100 microliters, between 200 nanoliters and 100 microliters, between 300 nanoliters and 100 microliters, between 500 nanoliters and 100 microliters, between 750 nanoliters and 100 microliters, between 1.0 microliter and 100 microliters, between 10 microliters and 100 microliters, between 50 microliters and 100 microliters, between 1.0 microliter and 75 microliters, between 1.0 microliter and 50 microliters, or between 1.0 microliters and 30 microliters.

Detectably labeled oligonucleotide controls may be contacted with cells in concentrations between about 0.1 nanomoles and 1000 nanomoles, between about 1.0 nanomole and 1000 nanomoles, between about 5.0 nanomoles and 1000 nanomoles, between about 10 nanomoles and 1000 nanomoles, between about 20 nanomoles and 1000 nanomoles, between about 40 nanomoles and 1000 nanomoles, between about 60 nanomoles and 1000 nanomoles, between about 100 nanomoles and 1000 nanomoles, between about 0.1 nanomole and 800 nanomoles, between about 0.1 nanomoles and 700 nanomoles, between about 0.1 nanomoles and 600 nanomoles, between about 0.1 nanomoles and 500 nanomoles, between about 0.1 nanomoles and 400 nanomoles, between about 10 nanomoles and 600 nanomoles, between about 10 nanomoles and 500 nanomoles, between about 10 nanomoles and 300 nanomoles, between about 10 nanomoles and 200 nanomoles, between about 10 nanomoles and 100 nanomoles, between about 10 nanomoles and 50 nanomoles, or between about 20 nanomoles and 200 nanomoles.

Exemplary formulations of the above components are set out in the product literature and table set forth in Example 15.

Conjugating Agents

Conjugating agents bind to the oligonucleotide in a covalent manner. In one embodiment, oligonucleotides can be derivatized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648).

Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides. Accordingly, the present invention provides for derivatization of oligonucleotides with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes, and steroids. A major advantage of using conjugating agents is to increase the initial membrane interaction that leads to a greater cellular accumulation of oligonucleotides.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a liposome delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphothioate oligonucleotide. (Vlassov et al., 1994, Biochimica et Biophysica Acta 1197:95-108). Oligonucleotides can also be complexed with, e.g., poly (L-lysine)

or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. No. 4,235,871; U.S. Pat. Nos. 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used. For example, a peptide such as (N-term) His-Ile-Trp-Leu-Ile-Tyr-Leu-Trp-Ile-Val-(C-term) (SEQ ID NO: 14) could be used. In one embodiment such a composition can be mixed with the fusogenic lipid DOPE as is well known in the art.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

For example, in one embodiment, the transporting peptide comprises an amino acid sequence derived from the antennapedia protein. Preferably, the peptide comprises amino acids 43-58 of the antennapedia protein (Arg-Gln-Ile-Lys-Ile-Trp-Phe-Gln-Asn-Arg-Arg-Met-Lys-Trp-Lys-Lys) (SEQ ID NO: 15) or a portion or variant thereof that facilitates transport of an oligonucleotide into a cell (see, e.g., WO 91/1898; Derossi et al. 1998. *Trends Cell Biol.* 8:84). Exemplary variants are shown in Derossi et al., supra.

In one embodiment, the transporting peptide comprises an amino acid sequence derived from the transportan, galanin (1-12)-Lys-mastoparan (1-14) amide, protein. (Pooga et al. 1998. *Nature Biotechnology* 16:857). Preferably, the peptide comprises the amino acids of the transportan protein shown in the sequence GWTLNSAGYLLGKINLKAL-AALAK- KIL (SEQ ID NO: 16) or a portion or variant thereof that facilitates transport of an oligonucleotide into a cell.

In one embodiment, the transporting peptide comprises an amino acid sequence derived from the HIV TAT protein. Preferably, the peptide comprises amino acids 37-72 of the HIV TAT protein, e.g., shown in the sequence C(Acm) FITKALGISYGRKKRRQRRR-PPQC (SEQ ID NO: 17) (TAT 37-60; where C(Acm) is Cys-acetamidomethyl) or a portion or variant thereof, e.g., C(Acm)GRKKRRQRRRP-PQC (SEQ ID NO: 18) (TAT 48-40) or C(Acm)LGI-SYGRKKRRQRRPPQC (SEQ ID NO: 19) (TAT 43-60) that facilitates transport of an oligonucleotide into a cell (Vives et al. 1997. *J. Biol. Chem.* 272:16010). In another embodiment the peptide (G)CFITKALGISYGRKKRRQR-RRP-PQGSQTHQVSLSKQ (SEQ ID NO: 20) can be used.

Portions or variants of transporting peptides can be readily tested to determine whether they are equivalent to these peptide portions by comparing their activity to the activity of the native peptide, e.g., their ability to transport fluorescently-labeled oligonucleotides to cells. Fragments or variants that retain the ability of the native transporting peptide to transport an oligonucleotide into a cell are functionally equivalent and can be substituted for the native peptides.

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. *J. Cell Biol.* 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. Biochimica et Biophysica Acta 1197:95-108).

Assays of Oligonucleotide Stability

Preferably, the double-stranded oligonucleotides of the invention are stabilized, i.e., substantially resistant to endo-nuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding, single-stranded oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. *J Biol. Chem.* 266:18162-71; T. Fisher, et al. 1993. *Nucleic Acids Research.* 21 3857).

The ability of an oligonucleotide composition of the invention to inhibit protein synthesis can be measured using techniques which are known in the art, for example, by detecting an inhibition in gene transcription or protein synthesis. For example, Nuclease Si mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. *J. Biol. Chem.* 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, β-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

Monitoring the Effects of Oligonucleotide

Monitoring the effects of double-stranded oligonucleotides of the invention on cell lines can by performed by the addition of stain compounds to cells, tissues, or organisms undergoing experiments or treatment. Addition of a stain compound to cells, tissues, or organisms in an experiment allows for the monitoring of the effects of the oligonucleotide at one or more discrete time points or in real time with continuous monitoring. Effects monitored can include apoptosis, cellular health and vitality, cell proliferation, cellular phenotypic changes, and so on. Stain compounds can be fluorescent or otherwise cause a detectable signal when interacting with a target.

Methods for monitoring the effects of an oligonucleotide of the present invention generally comprise contacting one or more cells with an oligonucleotide molecule and a stain compound, and detecting a signal from the cells. The contacting step can occur in one step, where the oligonucleotide molecule and the stain compound are introduced into the cell simultaneously. Alternatively, the contacting step can be performed stepwise, where the stain molecule is introduced into the cell, and then the oligonucleotide molecule is introduced into the cell, or vise versa. The contacting step can include the addition of cellular uptake agents such as a surfactant. Multiple oligonucleotide molecules can be used, such as 2, 3, 4, 5, 6, and so on. Multiple stain compounds can be used, such as 2, 3, 4, 5, 6, and so on.

Stain compounds can generally be any compound that generates a detectable signal upon interaction with a target. Compounds typically are luminescent (e.g. fluorescent, chemiluminescent, or phosphorescent). Stain compounds can generate the detectable signal directly (i.e. signal is generated upon interaction), or indirectly by including a third compound (e.g. the stain compound can be an enzyme that acts upon a substrate that becomes fluorescent). Examples of stain compounds include DNA labeled with a fluorescent molecule, RNA labeled with a fluorescent molecule, an antibody labeled with a fluorescent molecule, a Fab fragment labeled with a fluorescent molecule, and so on. The fluorescent molecule can be an organic compound, or a protein such as green fluorescent protein (GFP). Antibodies can be a labeled primary antibody, or a combination of an unlabeled primary antibody and a labeled secondary antibody. Antibodies can be labeled with a fluorescent or other detectable group, or can be labeled with an enzyme (such as a peroxidase, alkaline phosphatase, galactosidase, luciferase, or lactamase) that can react with a substrate. Stain compounds can interact with various targets. Targets include nucleic acid (e.g. DNA), proteins, peptides, and lipids. Targets can also include cellular structures such as cytoplasm, cytoskeleton, endoplasmic reticulum (ER), golgi, lysosomes, mitochondria, nucleus, nucleoli, peroxisomes, and plasma membrane.

Specific examples of stain compounds useful for studying changes in cell structure include 4',6-diamidino-2-phenylindole dihydrochloride (useful counterstain for nucleus and chromosomes), Hoechst 33342 trihydrochloride trihydrate (useful cell-permeant nuclear counterstain that emits blue fluorescence when bound to dsDNA; can be used to distinguish condensed pycnotic nuclei in apoptotic cells and for cell-cycle studies with BrdU), SYTOX Blue (a blue-fluorescent nuclear and chromosome counterstain that is impermeant to live cells), SYTOX Green (a green-fluorescent nuclear and chromosome counterstain that is impermeant to live cells), YO-PRO-1 iodide (a carbocyanine nucleic acid stain useful for identifying apoptotic cells), BO-PRO-1 iodide (a carbocyanine nucleic acid stain), SYTO 59 (a cell-permeant nucleic acid stain), and TO-PRO-3 iodide (a carbocyanine monomer useful as a dead cell indicator).

Specific examples of stain compounds useful for studying DNA fragmentation include 5-bromo-2'-deoxyuridine 5'-triphosphate (BrdUTP) with Alexa Fluor 488 anti-BrdU, anti-bromodeoxyuridine, mouse IgG1, monoclonal PRB-1 Alexa Fluor 488 conjugate (anti-BrdU, Alexa Fluor 488 conjugate), and anti-bromodeoxyuridine, mouse IgG1, monoclonal PRB-1 Alexa Fluor 594 conjugate (anti-BrdU, Alexa Fluor 594 conjugate).

Specific examples of stain compounds useful for studying cell proliferation include CyQUANT, and carboxyfluorescein diacetate succinimidyl ester.

Specific examples of stain compounds useful for studying apoptosis include caspase substrates rhodamine 110, bis-(N-CBZ-L-isoleucyl-L-glutamyl-L-threonyl-L-aspartic acid amide), Z-DEVD-AMC($C_{36}H_{41}N_5O_{14}$), Z-DEVD-AMC ($C_{36}H_{41}N_5O_{14}$), and rhodamine 110, bis-(L-aspartic acid amide). Compounds useful for studying phosphatidylserine exposure include recombinant annexin V conjugated to green-fluorescent Alexa Fluor 488 dye, green-fluorescent Alexa Fluor 488 annexin with red-fluorescent propidium iodide nucleic acid stain, Alexa Fluor 488 annexin V conjugate with SYTOX Green nucleic acid stain and $C_{12}$-resazurin, recombinant annexin V conjugated to allophycocyanin (APC) and a SYTOX Green nucleic acid stain, recombinant annexin V conjugated to R-phycoerythrin (R-PE) and a SYTOX Green nucleic acid stain, Alexa Fluor 568 annexin V conjugate, Alexa Fluor 594 annexin V conjugate, Alexa Fluor 350 annexin V conjugate, and Alexa Fluor 647 annexin V conjugate.

Specific examples of stain compounds useful for studying changes in mitochondria include MitoTracker Red CMXRos (a red-fluorescent dye that stains mitochondria in live cells), MitoTracker Green FM (a green-fluorescent mitochondrial stain that stains live cells), and MitoTracker Orange CMT-MRos (an orange-fluorescent mitochondrial stain that stains live cells).

Specific examples of stain compounds useful for studying changes in lysosomes include LysoTracker Red DND-99 (a red-fluorescent dye that stains acidic compartments in live cells), LysoTracker Green DND-26 (a green-fluorescent dye that stains acidic compartments in live cells), and LysoSensor Yellow/Blue DND-160 (an acidotropic probe that accumulates in acidic organelles due to protonation).

Specific examples of stain compounds useful for studying changes in plasma membranes include FM 1-43FX (a membrane probe analog modified to contain an aliphatic amine), Vybrant DiI (a lipophilic membrane stain), Vybrant DiO (a lipophilic membrane stain), and Vybrant DiD (a lipophilic membrane stain).

Specific examples of stain compounds useful for studying changes in the cytoplasm include Calcein AM (a cell-permeant dye used to determine cell viability in eukaryotic cells), CellTracker Green CMFDA (a fluorescent chloromethyl derivative that exhibits green fluorescence in the cytoplasm at physiological pH), and CellTracker Red CMTPX (a fluorescent chloromethyl derivative that exhibits red fluorescence in the cytoplasm at physiological pH).

Specific examples of stain compounds useful for studying changes in the endoplasmic reticulum include ER-Tracker Blue-White DPX (a photostable probe that is selective for the endoplasmic reticulum in live cells), SelectFX Alexa Fluor 488 (primary and secondary antibody pair), and brefeldin A BODIPY 558/568 conjugate (a labeled reversible inhibitor of protein transport from the endoplasmic reticulum to the Golgi apparatus).

Specific examples of stain compounds useful for studying changes in the peroxisome include SelectFX Alexa Fluor 488 (primary and secondary antibody pair directed against peroxisomal membrane protein 70).

Specific examples of stain compounds useful for studying changes in the Golgi include anti-golgin-97 (human) mouse IgG1 monoclonal CDF4 (anti-Golgin-97 antibody), NBD C6-ceramide complexed to BSA, BODIPY FL C5-ceramide complexed to BSA, and BODIPY TR C5-ceramide complexed to BSA (fluorescent ceramides are markers for Golgi Complex in living cells).

Specific examples of stain compounds useful for studying changes in the nucleoli include SYTO RNASelect green fluorescent cell stain (a cell permeant nucleic acid stain selective for RNA).

Specific examples of stain compounds useful for studying changes in the cytoskeleton include Alexa Fluor 488 phalloidin (a high-affinity probe for F-actin conjugated to a green-fluorescent dye), rhodamine phalloidin (a high-affinity probe for F-actin conjugated to the orange-fluorescent dye tetramethylrhodamine (TRITC)), jasplakinolide (a macrocyclic peptide), latrunculin A (binding to monomeric G-actin in a 1:1 complex), Oregon Green 488 Taxol (paclitaxel labeled at the 7-carbon with a fluorescent dye), anti-alpha tubulin mouse IgG1 (enables visualization of microtubules with an anti-mouse IgG secondary immunoreagent).

Specific examples of stain compounds useful for studying changes in lipid rafts include Vybrant Alexa Fluor 488 (chlorea toxin subunit B labeled with a fluorescent dye), Vybrant Alexa Fluor 555 (chlorea toxin subunit B labeled with a fluorescent dye), and Vybrant Alexa Fluor 594 (chlorea toxin subunit B labeled with a fluorescent dye).

Specific examples of stain compounds useful for studying changes in calcium levels include fluo-4 AM, fura-2 AM, indo-1 AM, and rhod-2 AM.

Specific examples of stain compounds useful for studying changes in reactive oxygen species levels include 5-chloromethyl-2',7'-dichlorodihydrofluorescein diacetate acetyl ester (a cell permeant indicator for reactive oxygen species that is nonfluorescent until removal of the acetate groups by intracellular esterases and oxidation), 6-chloromethyl-2',7'-dichlorodihydrofluorescein diacetate acetyl ester (a cell permeant indicator for reactive oxygen species that is nonfluorescent until removal of the acetate groups by intracellular esterases and oxidation), dihydroethidium (hydroethidine) (cell permeant stain becomes red-fluorescent ethidium and accumulates in the nucleus), aminophenyl fluorescein, hydroxyphenyl fluorescein, BODIPY 581/591 fatty acid C11, and glutathione ethyl ester biotin amide.

Specific examples of stain compounds useful for studying changes in reactive nitrogen species levels include anti-nitrotyrosine rabbit IgG (used in conjunction with an anti-rabbit IgG secondary immunoreagent), and DAF-FM diacetate (useful for quantitating low concentrations of nitric oxide in cells).

Specific examples of stain compounds useful for studying changes in sodium levels include CoroNa Green AM (exhibits increased green fluorescence emission upon binding sodium).

Specific examples of stain compounds useful for studying changes in pH levels include BCECF AM, 5-chloromethyl SNARF-1 acetate, and 6-chloromethyl SNARF-1 acetate.

Specific examples of stain compounds useful for studying changes in zinc levels include FluoZin-3 tetrapotassium salt (green fluorescent, suitable for detection of $Zn^{2+}$ at 1-100 mM concentrations), and RhodZin-3 AM (orange-red fluorescent indicator useful for measuring $Zn^{2+}$ in mitochondria).

The contacting step can be performed in a variety of environments or containers. For example, cells in a centrifuge tube, microscope slide, or multiwell plate can be contacted. Alternatively, tissues, tissue slices, or whole organisms can be contacted.

The method can further comprise an incubation step prior to the detection step. The incubation step can vary in length depending on the oligonucleotide experiment.

The detecting step can generally be performed by any machine or method suitable for detecting the signal. Examples of detecting steps include use of a fluorescence microscope, use of a plate reader, and use of a flow cytometer. The detecting step can be qualitative or quantitative. The detecting step can be performed at one or more discrete time points, or can be done continuously in real time.

The detecting step can comprise applying light at an absorbance wavelength to the cells, and detecting light emitted at a different wavelength. Examples of pairs of absorbance and emission wavelengths (in nm) include 346/442, 402/421, 495/519, 555/565, 578/603, 590/617, 650/668, 663/690, 679/702, and 749/775.

The methods can further comprise comparing the detected signal with signal(s) detected from control samples. For example, a control cell or cells can be treated with the same stain compound, but not with the oligonucleotide molecule.

Cellular effects may be exhibited as graded responses (as compared to all-or-none responses) in individual cells and may effect different cells in a population differently. Even in cells which share a common clonal origin, effects may be exhibited in certain cells in a population but not in others. Thus, methods disclosed herein may be used to determine the physiological status or condition of multiple cells in a population and compare that status or condition of those cells to the status or condition of cells which have not been treated.

The one or more cells can generally be any type of cell. Examples of cells include bacterial cells, fungal cells, insect cells, and mammalian cells. The cells can be a homogeneous or heterogeneous population. The cells can be mixtures of multiple types of cells from the same organism, or mixtures of cells from different organisms. The cells can be "wild-type" or modified through genetic engineering, viral or pathogen infection, randomly or specifically mutagenized, and so on.

The effects of the oligonucleotide monitored can generally be any effect. Effects can include cell viability, cell vitality, apoptosis, cell proliferation, signal transduction, energy charge, cell morphology, the activity of one or more enzymes, membrane potential, gene expression efficiency, cytoskeletal integrity, and the presence or absence of vacuoles. Effects can be measured relative to a control cell of the same type that is not treated with the oligonucleotide molecule. Depending on the effect measured, the signal obtained from the treated cell may be higher or lower than the signal obtained from the control cell. The signal obtained from the treated cell may increase or decrease over time, depending on the effect of the oligonucleotide molecule. Effects can include changes in pH, changes in concentration of a material (e.g. calcium or sodium), changes in shape, changes in oxidation state, and so on.

Additional embodiments involve kits useful for conducting oligonucleotide experiments. The kits can comprise one or more of the oligonucleotides of the invention, and one or more of the above described stain compounds. The kits can further comprise an instruction protocol. The kits can comprise one or more containers for holding the oligonucleotide molecule, the stain compound, or both. The kits can comprise one or more containers for conducting the oligonucleotide experiments. The kits can comprise one or more buffers. The kits can comprise one or more solvents. The kits can comprise one or more positive or negative standards. The kits can comprise positive or negative control samples or reference samples.

Oligonucleotide Synthesis

Oligonucleotides of the invention can be synthesized by any method known in the art, e.g., using enzymatic synthesis and chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. *J.*

Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. No. 5,013,830; U.S. Pat. No. 5,214,135; U.S. Pat. No. 5,525,719; Kawasaki et al. 1993. *J. Med. Chem.* 36:831; WO 92/03568; U.S. Pat. No. 5,276,019; and U.S. Pat. No. 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nucl. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC(SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

Uses of Oligonucleotides

The invention also features methods of inhibiting expression of a protein in a cell including contacting the cell with one of the above-described oligonucleotide compositions.

The oligonucleotides of the invention can be used in a variety of in vitro and in vivo situations to specifically inhibit protein expression. The instant methods and compositions are suitable for both in vitro and in vivo use.

Methods of the invention may be used for determining the function of a gene in a cell or an organism or for modulating the function of a gene in a cell or an organism, being capable of responding to or mediating RNA interference. The cell is preferably a eukaryotic cell or a cell line, e.g., an animal cell such as a mammalian cell, e.g., an embryonic cell, a pluripotent stem cell, a tumor cell, e.g., a teratocarcinoma cell, or a virus-infected cell. The organism is preferably a eukaryotic organism, e.g., an animal such as a mammal, particularly a human.

The invention includes methods to inhibit expression of a target gene in a cell in vitro. For example, such methods may include introduction of RNA into a cell in an amount sufficient to inhibit expression of the target gene, where the RNA is a double-stranded molecule of the invention. By way of a further example, such an RNA molecule may have a first strand consisting essentially of a ribonucleotide sequence that corresponds to a nucleotide sequence of the target gene, and a second strand consisting essentially of a ribonucleotide sequence that is complementary to the nucleotide sequence of the target gene, in which the first and the second strands are separate complementary strands or are joined by a loop, and they hybridize to each other to form said double-stranded molecule, such that the duplex composition inhibits expression of the target gene. The duplex composition may include modified nucleomonomers as discussed above.

The invention also relates to a method to inhibit expression of a target gene in an invertebrate organism. Such methods include providing an invertebrate organism containing a target cell that contains the target gene, in which the target cell is susceptible to RNA interference and the target gene is expressed in the target cell. Such methods further include contacting the invertebrate organism with an RNA composition of the invention. For example, the RNA may be a double-stranded molecule with a first strand consisting essentially of a ribonucleotide sequence that corresponds to a nucleotide sequence of the target gene and a second strand consisting essentially of a ribonucleotide sequence that is complementary to the nucleotide sequence of the target gene. In such cases, the first and the second ribonucleotide sequences may be separate complementary strands or joined by a loop, and they hybridize to each other to form the double-stranded molecule. Finally, such methods include a step of introducing the duplex RNA composition into the target cell to thereby inhibiting expression of the target gene.

In one embodiment, the oligonucleotides of the invention can be used to inhibit gene function in vitro in a method for identifying the functions of genes. In this manner, the transcription of genes that are identified, but for which no function has yet been shown, can be inhibited to thereby determine how the phenotype of a cell is changed when the gene is not transcribed. Such methods are useful for the validation of genes as targets for clinical treatment, e.g., with oligonucleotides or with other therapies.

To determine the effect of a composition of the invention, a variety of end points can be used. In addition to the assays described previously herein, for example, nucleic acid probes (e.g., in the form of arrays) can be used to evaluate transcription patterns produced by cells. Probes can also be used detect peptides, proteins, or protein domains, e.g., antibodies can be used to detect the expression of a particular protein. In yet another embodiment, the function of a protein (e.g., enzymatic activity) can be measured. In yet another embodiment, the phenotype of a cell can be evaluated to determine whether or not a target protein is expressed. For example, the ability of a composition to affect a phenotype of a cell that is associated with cancer can be tested.

In one embodiment, one or more additional agents (e.g., activating agents, inducing agents, proliferation enhancing agents, tumor promoters) can be added to the cells.

In another embodiment, the compositions of the invention can be used to monitor biochemical reactions such as, e.g., interactions of proteins, nucleic acids, small molecules, or the like, for example the efficiency or specificity of interactions between antigens and antibodies; or of receptors (such as purified receptors or receptors bound to cell membranes) and their ligands, agonists or antagonists; or of enzymes (such as proteases or kinases) and their substrates, or increases or decreases in the amount of substrate converted to a product; as well as many others. Such biochemical assays can be used to characterize properties of the probe or target, or as the basis of a screening assay. For example, to screen samples for the presence of particular proteases (e.g., proteases involved in blood clotting such as proteases Xa and VIIa), the samples can be assayed, for example using probes which are fluorogenic substrates specific for each protease of interest. If a target protease binds to and cleaves a substrate, the substrate will fluoresce, usually as a result, e.g., of cleavage and separation between two energy transfer pairs, and the signal can be detected. In another example, to screen samples for the presence of a particular kinase(s) (e.g., a tyrosine kinase), samples containing one or more kinases of interest can be assayed, e.g., using probes are peptides which can be selectively phosphorylated by one of the kinases of interest. Using art-recognized, routinely determinable conditions, samples can be incubated with an array of substrates, in an appropriate buffer and with the necessary cofactors, for an empirically determined period of time. If necessary, reactions can be stopped, e.g., by washing and the phosphorylated substrates can be detected by, for example, incubating them with detectable reagents such as, e.g., fluorescein-labeled anti-phosphotyrosine or anti-phosphoserine antibodies and the signal can be detected.

In another embodiment, the compositions of the invention can be used to screen for agents which modulate a pattern of gene expression. Arrays of oligonucleotides can be used, for example, to identify mRNA species whose pattern of expression from a set of genes is correlated with a particular physiological state or developmental stage, or with a disease condition ("correlative" genes, RNAs, or expression patterns). By the terms "correlate" or "correlative," it is meant that the synthesis pattern of RNA is associated with the physiological condition of a cell, but not necessarily that the expression of a given RNA is responsible for or is causative of a particular physiological state. For example, a small subset of mRNAs can be identified which are modulated (e.g., upregulated or downregulated) in cells which serve as a model for a particular disease state. This altered pattern of expression as compared to that in a normal cell, which does not exhibit a pathological phenotype, can serve as a indicator of the disease state ("indicator" or "correlative" genes, RNAs, or expression patterns).

Compositions which modulate the chosen indicator expression pattern (e.g., compared to control compositions comprising, for example oligonucleotides which comprise a nucleotide sequence which is the reverse of the oligonucleotide, or which contains mismatch bases) can indicate that a particular target gene is a potential target for therapeutic intervention. Moreover, such compositions may be useful as therapeutic agents to modulate expression patters of cells in an in vitro expression system or in in vivo therapy. As used herein, "modulate" means to cause to increase or decrease the amount or activity of a molecule or the like which is involved in a measurable reaction. In one embodiment, a series of cells (e.g., from a disease model) can be contacted with a series of agents (e.g., for a period of time ranging from about 10 minutes to about 48 hours or more) and, using routine, art-recognized methods (e.g., commercially available kits), total RNA or mRNA extracts can be made. If it is desired to amplify the amount of RNA, standard procedures such as RT-PCR amplification can be used (see, e.g., Innis et al eds., (1996) PCR Protocols: A Guide to Methods in Amplification, Academic Press, New York). The extracts (or amplified products from them) can be allowed to contact (e.g., incubate with) probes for appropriate indicator RNAs, and those agents which are associated with a change in the indicator expression pattern can be identified.

Similarly, agents can be identified which modulate expression patterns associated with particular physiological states or developmental stages. Such agents can be man-made or naturally-occurring substances, including environmental factors such as substances involved in embryonic development or in regulating physiological reactions.

In one embodiment, the methods described herein can be performed in a "high throughput" manner, in which a large number of target genes (e.g., as many as about 1000 or more, depending on the particular format used) are assayed rapidly and concurrently. Further, many assay formats (e.g., plates or surfaces) can be processed at one time. For example, because the oligonucleotides of the invention do not need to be tested individually before incorporating them into a composition, they can be readily synthesized and large numbers of target genes can be tested at one time. For example, a large number of samples, each comprising a biological sample containing a target nucleic acid molecule (e.g., a cell) and a composition of the invention can be added to separate regions of an assay format and assays can be performed on each of the samples.

Administration of Oligonucleotide Compositions

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter.

The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regima may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Treatment of Diseases or Disorders

By inhibiting the expression of a gene, the oligonucleotide compositions of the present invention can be used to treat any disease involving the expression of a protein. Examples of diseases that can be treated by oligonucleotide compositions include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

Business Methods

The present invention also provides a system and method of providing company products to a party outside of the company, for example, a system and method for providing a customer or a product distributor a product of the company such as a kit containing a double stranded nucleic acid molecule which is capable of inhibiting expression of a gene and/or instructions for inhibiting gene expression. FIG. 7 provides a schematic diagram of a product management system. In practice, the blocks in FIG. 7 can represent an intra-company organization, which can include departments in a single building or in different buildings, a computer program or suite of programs maintained by one or more computers, a group of employees, a computer I/O device such as a printer or fax machine, a third party entity or company that is otherwise unaffiliated with the company, or the like.

The product management system as shown in FIG. 7 is exemplified by company 100, which receives input in the form of an order from a party outside of the company, e.g., distributor 150 or customer 140, to order department 126, or in the form of materials and parts 130 from a party outside of the company; and provides output in the form of a product delivered from shipping department 119 to distributor 150 or customer 140. Company 100 system is organized to optimize receipt of orders and delivery of a products to a party outside of the company in a cost efficient manner, particularly instructions or a kit of the present invention, and to obtain payment for such product from the party.

With respect to methods of the present invention, the term "materials and parts" refers to items that are used to make a device, other component, or product, which generally is a device, other component, or product that company sells to a party outside of the company. As such, materials and parts include, for example, nucleotides, single stranded or double stranded nucleic acid molecules, host cells, enzymes (e.g., polymerases), amino acids, culture media, buffers, paper, ink, reaction vessels, etc. In comparison, the term "devices", "other components", and "products" refer to items sold by the company. Devices are exemplified by nucleic acid molecules that are to be sold by the company, for example, single stranded or double stranded nucleic acid molecules which may or may not contain one or more chemical modifications in one or both strands. Other components are exemplified by instructions, including instructions for determining a ratio of nucleic acid molecules to be combined with cells for optimal inhibition of gene expression according to a method of the invention. Other components also can be items that may be included in a kit, e.g., a kit product containing, for example, single stranded or double stranded nucleic acid molecules or cells of one or more type (e.g., 293 cells, HUVEC cells, etc). As such, it will be recognized that an item useful as materials and parts as defined herein further can be considered an "other component", which can be sold by the company. The term "products" refers to devices, other components, or combinations thereof, including combinations with additional materials and parts, that are sold or desired to be sold or otherwise provided by a company to one or more parties outside of the company. Products are exemplified herein by kits, which can contain instructions according to the present invention, and single stranded or double stranded nucleic acid molecules, or combinations thereof.

Referring to FIG. 7, company 100 includes manufacturing 110 and administration 120. Devices 112 and other components 114 are produced in manufacturing 110, and can be stored separately therein such as in device storage 113 and other component storage 115, respectively, or can be further assembled and stored in product storage 117. Materials and parts 130 can be provided to company 100 from an outside source and/or materials and parts 114 can be prepared in company, and used to produce devices 112 and other components 116, which, in turn, can be assembled and sold as a product. Manufacturing 110 also includes shipping department 119, which, upon receiving input as to an order, can obtain products to be shipped from product storage 117 and forward the product to a party outside the company.

For purposes of the present invention, product storage 117 can store instructions, for example, for determining transfection conditions which are suitable for use with a particular cell type or how to design a double stranded nucleic acid molecule which will function for inhibiting gene expression, as well as combinations of such instructions and/or kits. Upon receiving input from order department 126, for example, that customer 140 has ordered such a kit and instructions, shipping department 119 can obtain from product storage 117 such kit for shipping, and can further obtain such instructions in a written form to include with the kit, and ship the kit and instructions to customer 140 (and providing input to billing department 124 that the product was shipped; or shipping department 119 can obtain from product storage 117 the kit for shipping, and can further provide the instructions to customer 140 in an electronic form, by accessing a database in company 100 that contains the instructions, and transmitting the instructions to customer 140 via the internet (not shown).

As further exemplified in FIG. 7, administration 120 includes order department 126, which receives input in the form of an order for a product from customer 140 or distributor 150. Order department 126 then provides output in the form of instructions to shipping department 119 to fill the order, i.e., to forward products as requested to customer 140 or distributor 150. Shipping department 119, in addition to filling the order, further provides input to billing department 124 in the form of confirmation of the products that have been shipped. Billing department 124 then can provide output in the form of a bill to customer 140 or distributor 150 as appropriate, and can further receive input that the bill has been paid, or, if no such input is received, can further provide output to customer 140 or distributor 150 that such payment may be delinquent. Additional optional component of company 100 include customer service department 122, which can receive input from customer 140 and can provide output in the form of feedback or information to customer 140. Furthermore, although not shown in FIG. 7, customer service 122 can receive input or provide output to any other component of company. For example, customer service department 122 can receive input from customer 140 indicating that an ordered product was not received, wherein customer service department 122 can provide output to shipping department 119 and/or order department 126 and/or billing department 124 regarding the missing product, thus providing a means to assure customer 140 satisfaction. Customer service department 122 also can receive input from customer 140 in the form of requested technical information, for example, for confirming that instructions of the invention can be applied to the particular need of customer 140, and can provide output to customer 140 in the form of a response to the requested technical information.

As such, the components of company 100 are suitably configured to communicate with each other to facilitate the transfer of materials and parts, devices, other components, products, and information within company 100, and company 100 is further suitably configured to receive input from or provide output to an outside party. For example, a physical path can be utilized to transfer products from product storage 117 to shipping department 119 upon receiving suitable input from order department 126. Order department 126, in comparison, can be linked electronically with other components within company 100, for example, by a communication network such as an intranet, and can be further configured to receive input, for example, from customer 140 by a telephone network, by mail or other carrier service, or via the internet. For electronic input and/or output, a direct electronic link such as a T1 line or a direct wireless connection also can be established, particularly within company 100 and, if desired, with distributor 150 or materials or parts 130 provider, or the like.

Although not illustrated, company 100 system one or more data collection systems, including, for example, a customer data collection system, which can be realized as a personal computer, a computer network, a personal digital assistant (PDA), an audio recording medium, a document in which written entries are made, any suitable device capable of receiving data, or any combination of the foregoing. Data collection systems can be used to gather data associated with a customer 140 or distributor 150, including, for example, a customer's shipping address and billing address, as well as more specific information such as the customer's ordering history and payment history, such data being useful, for example, to determine that a customer has made sufficient purchases to qualify for a discount on one or more future purchases.

Company 100 can utilize a number of software applications to provide components of company 100 with information or to provide a party outside of company access to one or more components of company 100, for example, access to order department 126 or customer service department 122. Such software applications can comprise a communication network such as the Internet, a local area network, or an intranet. For example, in an internet-based application, customer 140 can access a suitable web site and/or a web server that cooperates with order department 126 such that customer 140 can provide input in the form of an order to order department 126. In response, order department 126 can communicate with customer 140 to confirm that the order has been received, and can further communicate with shipping department 119, providing input that products such as a kit of the invention, which contains, for example, a double-stranded nucleic acid molecule and instructions for use, should be shipped to customer 140. In this manner, the business of company 100 can proceed in an efficient manner.

In a networked arrangement, billing department 124 and shipping department 119, for example, can communicate with one another by way of respective computer systems. As used herein, the term "computer system" refers to general purpose computer systems such as network servers, laptop systems, desktop systems, handheld systems, personal digital assistants, computing kiosks, and the like. Similarly, in accordance with known techniques, distributor 150 can access a web site maintained by company 100 after establishing an online connection to the network, particularly to order department 126, and can provide input in the form of an order. If desired, a hard copy of an order placed with order department 126 can be printed from the web browser application resident at distributor 150.

The various software modules associated with the implementation of the present invention can be suitably loaded into the computer systems resident at company 100 and any party outside of company 100 as desired, or the software code can be stored on a computer-readable medium such as a floppy disk, magnetic tape, or an optical disk. In an online implementation, a server and web site maintained by company 100 can be configured to provide software downloads to remote users such as distributor 150, materials and parts 130, and the like. When implemented in software, the techniques of the present invention are carried out by code segments and instructions associated with the various process tasks described herein.

Accordingly, the present invention further includes methods for providing various aspects of a product (e.g., a kit and/or instructions of the invention), as well as information regarding various aspects of the invention, to parties such as the parties shown as customer 140 and distributor 150 in FIG. 7. Thus, methods for selling devices, products and methods of the invention to such parties are provided, as are methods related to those sales, including customer support, billing, product inventory management within the company, etc. Examples of such methods are shown in FIG. 7, including, for example, wherein materials and parts 130 can be acquired from a source outside of company 100 (e.g., a supplier) and used to prepare devices (e.g., double-stranded nucleic acid molecules) used in preparing a composition or practicing a method of the invention, for example, kits, which can be maintained as an inventory in product storage 117. It should be recognized that devices 112 can be sold directly to a customer and/or distributor (not shown), or can be combined with one or more other components 116, and sold to a customer and/or distributor as the combined product. The other components 116 can be obtained from a source outside of company 100 (materials and parts 130) or can be prepared within company 100 (materials and parts 114). As such, the term "product" is used generally herein to refer an item sent to a party outside of the company (a customer, a distributor, etc.) and includes items such as devices 112, which can be sent to a party alone or as a component of a kit or the like.

At the appropriate time, the product is removed from product storage 117, for example, by shipping department 119, and sent to a requesting party such as customer 140 or distributor 150. Typically, such shipping occurs in response to the party placing an order, which is then forwarded the within the organization as exemplified in FIG. 7, and results in the ordered product being sent to the party. Data regarding shipment of the product to the party is transmitted further within the organization, for example, from shipping department 119 to billing department 124, which, in turn, can transmit a bill to the party, either with the product, or at a time after the product has been sent. Further, a bill can be sent in instances where the party has not paid for the product shipped within a certain period of time (e.g., within 30 days, within 45 days, within 60 days, within 90 days, within 120 days, within from 30 days to 120 days, within from 45 days to 120 days, within from 60 days to 120 days, within from 90 days to 120 days, within from 30 days to 90 days, within from 30 days to 60 days, within from 30 days to 45 days, within from 60 days to 90 days, etc.). Typically, billing department 124 also is responsible for processing payment (s) made by the party. It will be recognized that variations from the exemplified method can be utilized; for example, customer service department 122 can receive an order from the party, and transmit the order to shipping department 119 (not shown), thus serving the functions exemplified in FIG. 7 by order department 126 and the customer service department 122.

Methods of the invention also include providing technical service to parties using a product, particularly a kit of the invention. While such a function can be performed by individuals involved in product research and development, inquiries related to technical service generally are handled, routed, and/or directed by an administrative department of the organization (e.g., customer service department 122). Often communications related to technical service (e.g., solving problems related to use of the product or individual components of the product) require a two way exchange of information, as exemplified by arrows indicating pathways of communication between customer 150 and customer service department 122.

As mentioned above, any number of variations of the process exemplified in FIG. 7 are possible and within the scope of the invention. Accordingly, the invention includes methods (e.g., business methods) that involve (1) the production of products (e.g., double-stranded nucleic acid molecules, transfection reagents, kits that contain instructions for performing methods of the invention, etc.); (2) receiving orders for these products; (3) sending the products to parties placing such orders; (4) sending bills to parties obliged to pay for products sent to such; and/or (5) receiving payment for products sent to parties. For example, methods are provided that comprise two or more of the following steps: (a) obtaining parts, materials, and/or components from a supplier; (b) preparing one or more first products (e.g., one or more double-stranded nucleic acid molecules); (c) storing the one or more first products of step (b); (d) combining the one or more first products of step (b) with one or more other components to form one or more second products (e.g., a kit); (e) storing the one or more first products of step (b) or one or more second products of step (d); (f) obtaining an order a first product of step (b) or a second product of step (d); (g) shipping either the first product of step (b) or the second product of step (d) to the party that placed the order of step (f); (h) tracking data regarding to the amount of money owed by the party to which the product is shipped in step (g); (i) sending a bill to the party to which the product is shipped in step (g); (j) obtaining payment for the product shipped in step (g) (generally, but not necessarily, the payment is made by the party to which the product was shipped in step (g); and (k) exchanging technical information between the organization and a party in possession of a product shipped in step (d) (typically, the party to which the product was shipped in step (g)).

The present invention also provides a system and method for providing information as to availability of a product (e.g., a device product, a kit product, and the like) to parties having potential interest in the availability of the kit product. Such a method of the invention, which encompasses a method of advertising to the general or a specified public, the availability of the product, particularly a product comprising instructions and/or a kit of the present invention, can be performed, for example, by transmitting product description data to an output source, for example, an advertiser; further transmitting to the output source instructions to publish the product information data in media accessible to the potential interested parties; and detecting publication of the data in the media, thereby providing information as to availability of the product to parties having potential interest in the availability of the product.

Accordingly, the present invention provides methods for advertising and/or marketing devices, products, and/or methods of the invention, such methods providing the advantage of inducing and/or increasing the sales of such devices, products, and/or methods. For example, advertising and/or marketing methods of the invention include those in which technical specifications and/or descriptions of devices and/or products; methods of using the devices and/or products; and/or instructions for practicing the methods and/or using the devices and/or products are presented to potential interested parties, particularly potential purchasers of the product such as customers, distributors, and the like. In particular embodiments, the advertising and/or marketing methods involve presenting such information in a tangible form or in an intangible to the potential interested parties. As disclosed herein and well known in the art, the term "intangible form" means a form that cannot be physically handled and includes, for example, electronic media (e.g., e-mail, internet web pages, etc.), broadcasts (e.g., television, radio, etc.), and direct contacts (e.g., telephone calls between individuals, between automated machines and individuals, between machines, etc.); whereas the term "tangible form" means a form that can be physically handled.

FIG. 8 provides a schematic diagram of an information providing management system as encompassed within the present invention. In practice, the blocks in FIG. 8 can represent an intra-company organization, which can include departments in a single building or in different buildings, a computer program or suite of programs maintained by one or more computers, a group of employees, a computer I/O device such as a printer or fax machine, a third party entity or company that is otherwise unaffiliated with the company, or the like.

The information providing management system as shown in FIG. 8 is exemplified by company 200, which makes, purchases, or otherwise makes available devices and methods 210 that alone, or in combination, provide products 220, for example, instructions, devices and/or kits of the present invention, that company 200 wishes to sell to interested parties. To this end, product descriptions 230 are made, providing information that would lead potential users to believe that products 220 can be useful to user. In order to effect transfer of product descriptions 230 to the potential users, product descriptions 230 is provided to advertising agency 240, which can be an entity separate from company 200, or to advertising department 260, which can be an entity related to company 200, for example, a subsidiary. Based on the product descriptions 230, advertisement 250 is generated and is provided to media accessible to potential purchasers of products 260, whom may then contact company 200 to purchase products 220.

By way of example, product descriptions 230 can be in a tangible form such as written descriptions, which can be delivered (e.g., mailed, couriered, etc) to advertising agency 240 and/or advertising department 250, or can be in an intangible form such as entered into and stored in a database (e.g., on a computer, in an electronic media, etc.) and transmitted to advertising agency 240 and/or advertising department 250 over a telephone line, T1 line, wireless network, or the like. Similarly, advertisement 250 can be a tangible or intangible form such that it conveniently and effectively can be provided to potential parties of interest (e.g., potential purchasers of product 260). For example, advertisement 250 can be provided in printed form as flyers (e.g., at a meeting or other congregation of potential interested parties) or as printed pages (or portions thereof) in magazines known to be read by the potential interested parties (e.g., trade magazines, journals, newspapers, etc.). In addition, or alternatively, advertisement 250 can be provided in the form of directed mailing of computer media containing the advertisement (e.g., CDs, DVDs, floppy discs, etc.) or of e mail (i.e., mail or e-mail that is sent only to selected parties, for example, parties known to members of an organization that includes or is likely to include potential users of products 220); of web pages (e.g., on a website provided by company 200, or having links to the company 200 website); or of pop-up or pop-under ads on web pages known to be visited by potential purchaser of products 260, and the like. Potential purchasers of products 260, upon being apprised of the availability of the products 220, for example, the kits of the present invention, then can contact company 200 and, if so desired, can order said products 220 for company 200 (see FIG. 7).

Kits and Instructions:

The invention also provides kits. In various aspects, a kit of the invention may contain one or more (e.g., one, two, three, four, five, six, seven, etc.) of the following components: (1) one or more sets of instructions, including, for example, instructions for performing methods of the invention or for preparing and/or using compositions of the invention; (2) one or more cells, including, for example, one or more mammalian cells, for example, cells that are adapted for growth in a tissue culture medium, (3) one or more oligonucleotide or double stranded nucleic acid molecule (including one or more control nucleic acid molecule, as described elsewhere herein); (4) one or more container containing water (e.g., distilled water) or other aqueous or liquid material; (5) one or more containers containing one or more buffers, which can be buffers in dry, powder form or reconstituted in a liquid such as water, including in a concentrated form such as 2×, 3×, 4×, 5×, etc.); and/or (6) one or more containers containing one or more salts (e.g., sodium chloride, potassium chloride, magnesium chloride, which can be in a dry, powder form or reconstituted in a liquid such as water).

A kit of the invention can include an instruction set, or the instructions can be provided independently of a kit. Such instructions may provide information regarding how to make or use one or more of the following items: (1) one or more control nucleic acid molecule (e.g., a nucleic acid molecule which may be used as a transfection control); (2) one or more double stranded nucleic acid molecule, as described elsewhere herein (e.g., a double stranded nucleic acid molecule which is capable of "knocking-down" expression of a gene where introduced into a eukaryotic cell); (3) one or more cell lines that contain a gene the expression of which is to be knocked down (e.g., pre-transfection growth conditions; transfection protocols; post-transfection growth conditions); (4) one or more dyes for distinguishing live from dead cells (e.g., Dead Red stain or Dead Cell Reagent), and/or (5) one or more sets of instructions for using kit components.

Instructions can be provided in a kit, for example, written on paper or in a computer readable form provided with the kit, or can be made accessible to a user via the internet, for example, on the world wide web at a URL (uniform resources link; i.e., "address") specified by the provider of the kit or an agent of the provider. Such instructions direct a user of the kit or other party of particular tasks to be performed or of particular ways for performing a task. In one aspect, the instructions instruct a user of how to perform methods of the invention. In a specific aspect, the instructions can, for example, instruct a user of a kit as to reaction conditions for knocking-down gene expression, including, for example, buffers, temperature, and/or time periods of incubations for using nucleic acid molecules described herein. Instructions of the invention can be in a tangible form, for example, printed or otherwise imprinted on paper, or in an intangible form, for example, present on an internet web page at a defined and accessible URL. Thus, the invention includes instructions for performing methods of the invention and/or for preparing compositions of the invention. While the instructions themselves are one aspect of the invention, the invention also includes the instructions in tangible form. Thus, the invention includes computer media (e.g., hard disks, floppy disks, CDs, etc.) and sheets of paper (e.g., a single sheet of paper, a booklet, etc.) which contain the instructions.

It will be recognized that a full text of instructions for performing a method of the invention or, where the instructions are included with a kit, for using the kit, need not be provided. One example of a situation in which a kit of the invention, for example, would not contain such full length instructions is where the provided directions inform a user of the kits where to obtain instructions for practicing methods for which the kit can be used. Thus, instructions for performing methods of the invention can be obtained from internet web pages, separately sold or distributed manuals or other product literature, etc. The invention thus includes kits that direct a kit user to one or more locations where instructions not directly packaged and/or distributed with the kits can be found. Such instructions can be in any form including, but not limited to, electronic or printed forms.

The invention is further illustrated by the following examples, which should not be construed as further limiting.

EXAMPLES

Example 1

Oligonucleotide Compositions Comprising Chimeric Antisense Sequences

A gapped antisense oligonucleotide comprising 2'-O-methyl RNA arms and an unmodified DNA gap was synthesized. A complementary oligonucleotide was also synthesized using unmodified RNA. A double-stranded duplex was formed and the composition was found to inhibit expression of the target gene.

Example 2

Length of Double-Stranded Oligonucleotides and the Presence or Absence of Overhangs has No Effect on Function Twenty one and 27-mers were designed to target each of two sites on the p53 molecule (89-90 site, and 93-94 site). The double-stranded molecules were designed with or without 3'-deoxy TT overhangs. The test oligonucleotides were 21-mers with 2 nucleotide 3' deoxy TT overhangs and without overhangs (blunt ends); and 27-mers with 2 nucleotide 3' deoxy TT overhangs and without overhangs (blunt ends). Two positive controls were included in the experiment (p53) and two negative controls were also included (FITC).

Figure 14A:
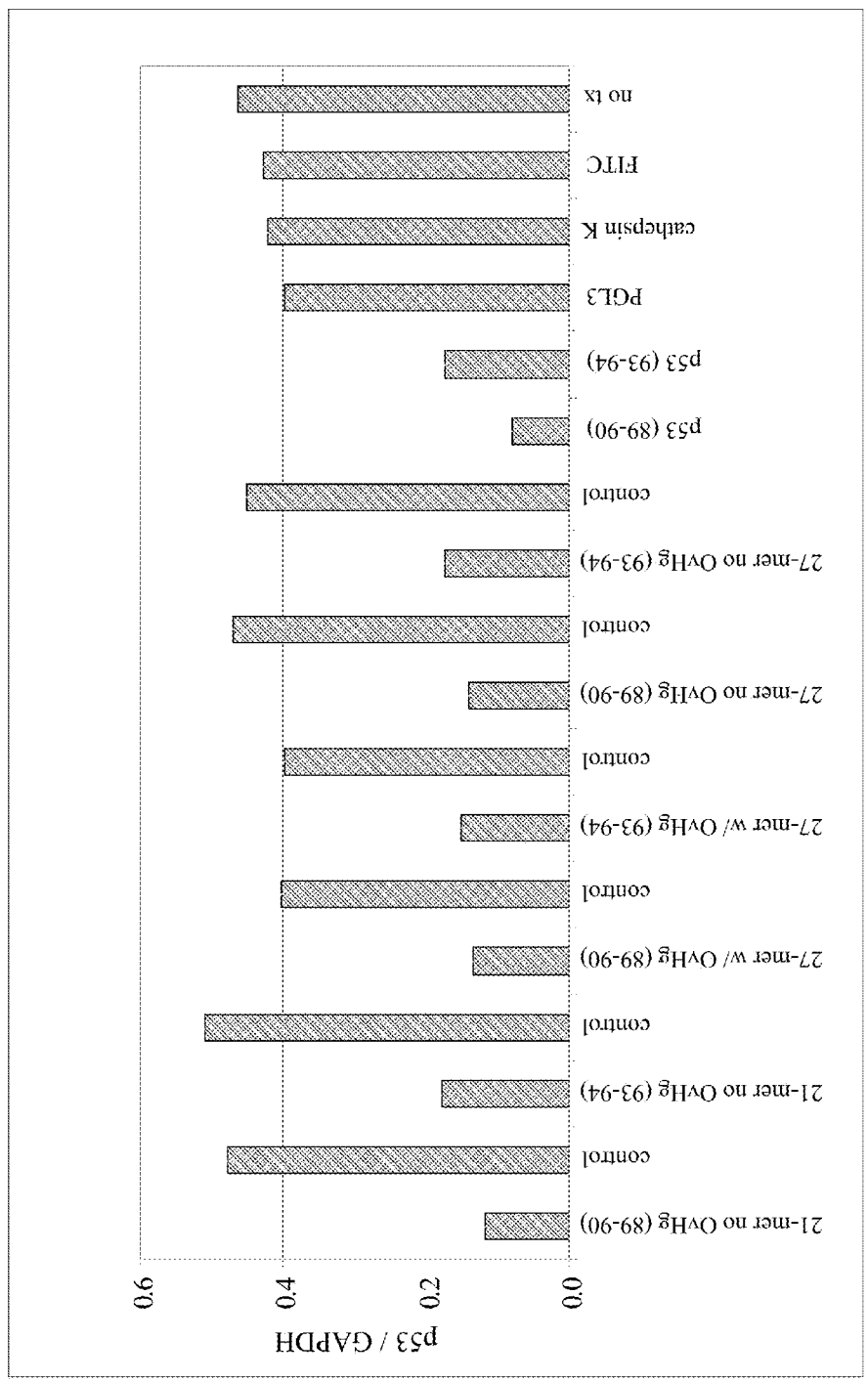
FIG. 14A shows that the length of double-stranded oligonucleotides and the presence or absence of overhangs has no effect on function.

A549 cells were transfected with 100 nM of the double-stranded molecules plus 2 ug/mL LIPOFECTAMINE™ 2000. A549 cells were examined 24 hours post-transfection. FITC-labeled molecules were taken up well by cells. Both 21-mers (with or without overhangs) and 27-mers (with or without overhangs) were non-toxic to cells. FIG. 14A shows the result of an experiment comparing the ability of different oligonucleotide constructs to inhibit p53 and shows that length or the presence or absence of a 3' deoxy TT overhang did not affect the activity of the oligonucleotide. The results in FIG. 14A show the amount of p53 mRNA normalized to the amount of an irrelevant message, GAPDH. The level of mRNA was determined using RT-PCR analysis. The observed percent inhibition of p53 expression is shown below:

| SITE | 21-MER overhang | 21-MER no overhang | 27-MER overhang | 27-MER no overhang |
|---|---|---|---|---|
| 93-94 | 58% | 65% | 62% | 62% |
| 89-90 | 81% | 75% | 67% | 70% |

Figure 14B:
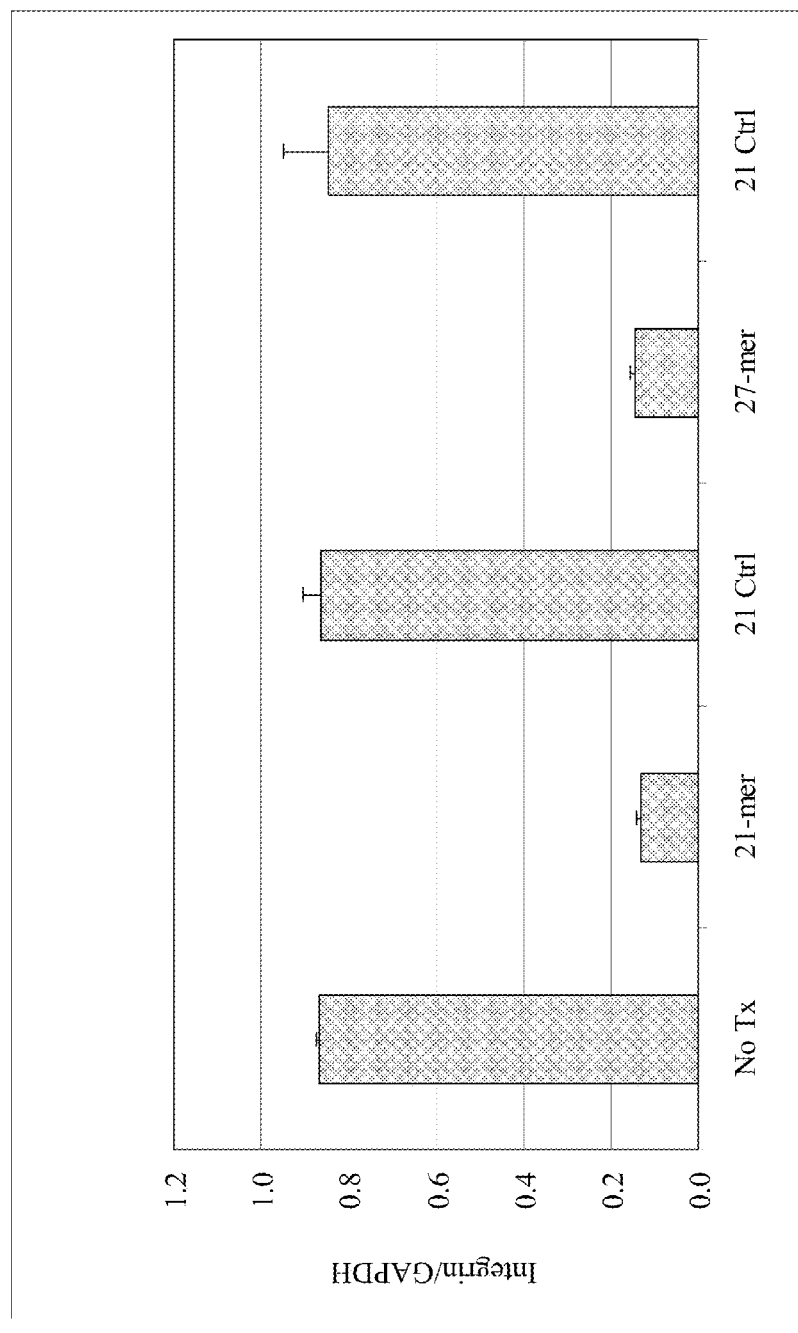
FIG. 14B shows the effect of structural changes on the efficacy of siRNAs targeting β-3-Integrin.

Similar results were observed for β-3-integrin; both 21-mer and 27-mer double-stranded molecules were found to inhibit integrin mRNA. Two double-stranded RNA complexes designed to target the same site of the β-3-integrin gene were transfected in HMVEC cells. Both complexes contained a two nucleotide (TT) overhang: one complex was a 21-mer (with 19 nucleotides complementary to the target gene) and the other was a 27-mer (with 25 nucleotides complementary to the target gene). RT-PCR analysis showed that the two complexes inhibited the target gene to the same extent. HMVEC cells were transfected using 100 nM oligomer complexed with 2.0 ug/mL of LIPOFECTAMINE™ 2000 in media containing serum for 24 hours. Twenty-four hours after transfection, the cells were lysed and the RNA was isolated for analysis by RT-PCR. No significant toxicity was observed. The results in FIG. 14B show the amount of β-3-integrin mRNA normalized to the amount of GAPDH, as determined by RT-PCR analysis.

Example 3

Activation of the Double-Stranded RNA, Interferon-Inducible Protein Kinase, PKR

Figure 15A:
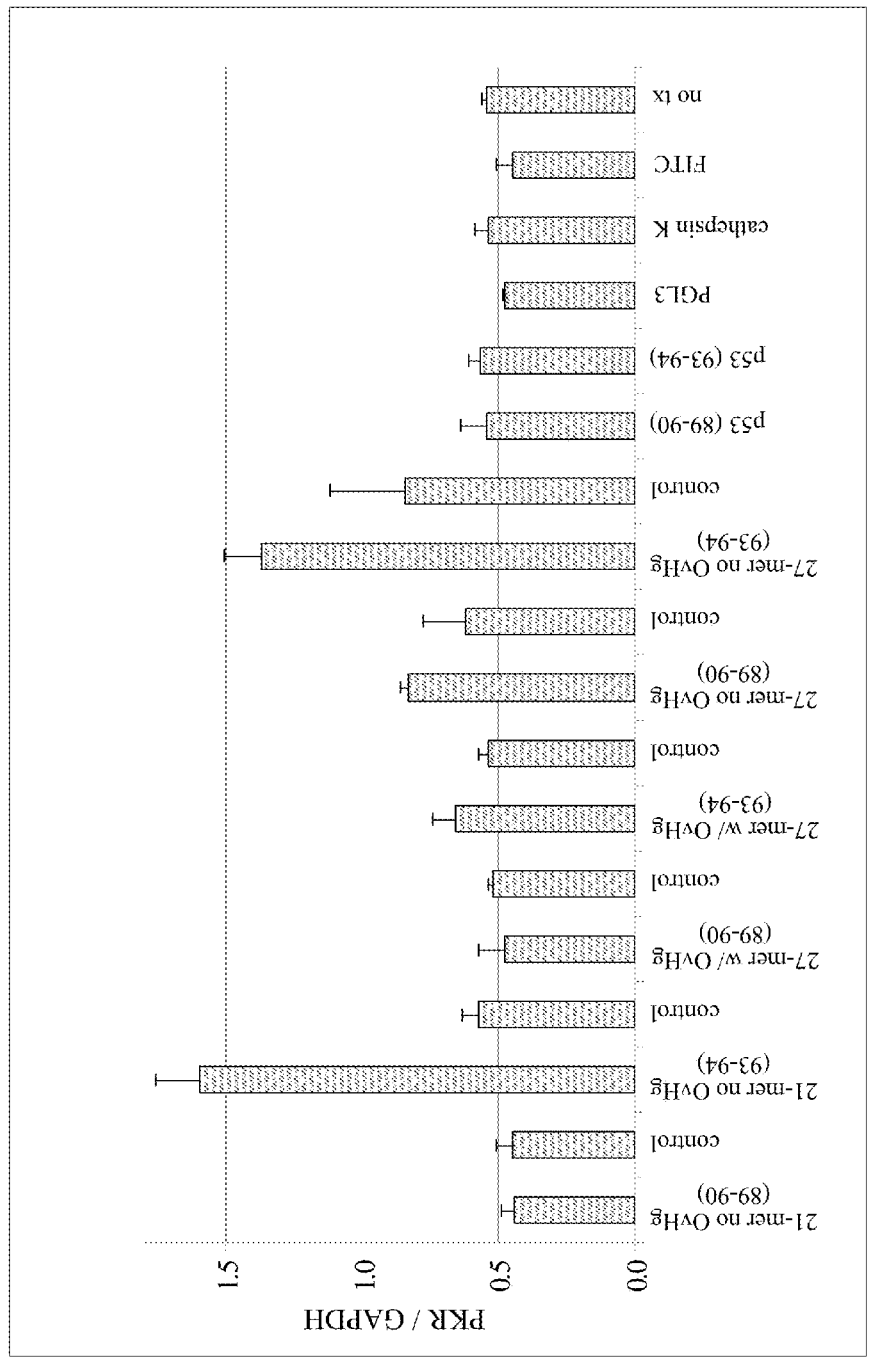
FIG. 15A shows that there is no correlation was observed between the length of the double-stranded oligonucleotide and the level of PKR induction for the given sequences.

PKR is activated by double-stranded RNA molecules. Active PKR leads to the inhibition of protein synthesis, activation of transcription, and a variety of other cellular effects, including signal transduction, cell differentiation, cell growth inhibition, apoptosis, and antiviral effects. The effect of p53-targeted double-stranded RNA molecules on PKR expression was tested. The level of mRNA was determined using RT-PCR analysis. As shown in FIG. 15A, no correlation was observed between the length of the double-stranded oligonucleotide and the level of PKR induction.

hours. The A549 cells were plated at 20,000/well in 48 well plates. After 24 hours, FITC-labeled double-stranded oligonucleotides were visible in A549 cells; the inclusion of a 2'-O-methyl group did not affect uptake. The Table below shows the results of this experiment.

| | 2'O-Methyl Oligonucleotide Duplexes | | | |
|---|---|---|---|---|
| | Anti-sense/Sense | Anti-sense/Sense | Anti-sense/Sense | Anti-sense/Sense |
| | 2'-O—Me/2'-O—Me | 2'-O—Me/RNA | RNA/2'-O—Me | RNA/RNA |
| targeted | 18639/18640 | 18639/16194 | 16193/18640 | 18876 |
| non-targeted | 19039/19040 | 19039/19044 | 19043/19040 | 18850 & 16197/16198 |
| | FITC-2'-O—Me/ FITC 2'-O—Me | FITC-2'-O—Me/ FITC-RNA | FITC-2'-O—Me/ RNA | 2'-O—Me/ FITC-RNA |
| non-targeted | 19209 | 19037/19042 | 19037/19044 | 19039/19042 |

Accordingly, long oligonucleotides can be used without activating PKR, a marker for interferon induction.

Figure 15B:
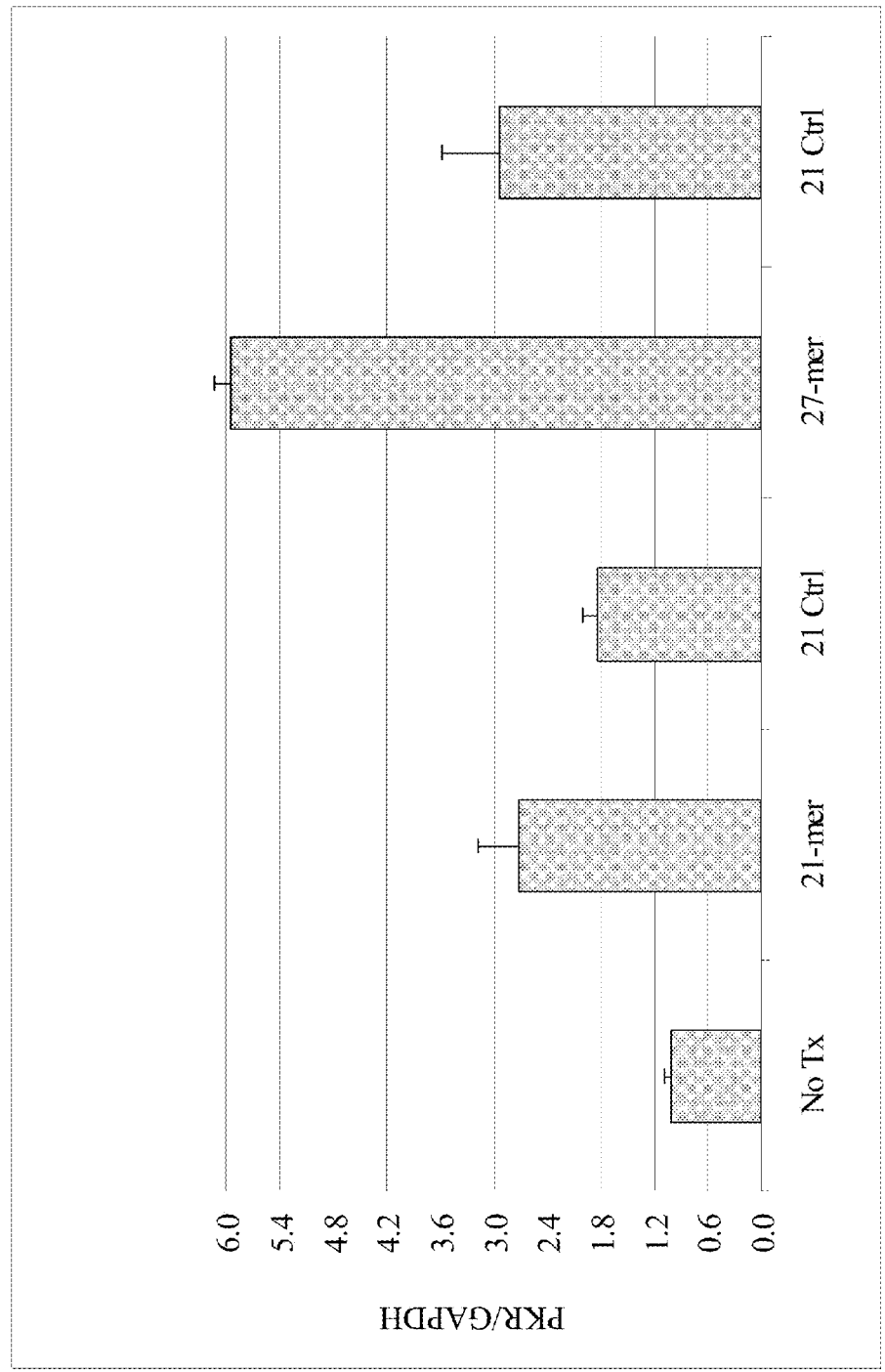
FIG. 15B shows effect of β-3-Integrin targeted 21-mers and 27-mers on PKR expression in HMVEC Cells.

As illustrated in FIG. 15B, analysis of relative amounts of PKR mRNA after the 21- and 27-mer transfection in HMVEC cells showed approximately a 2 fold increase in PKR mRNA of the siRNA control sequences over no treatment, and approximately a 2 fold increase of PKR mRNA of the 27-mer compared to the 21-mer targeted double-stranded RNA complexes.

Example 4

Figure 16:
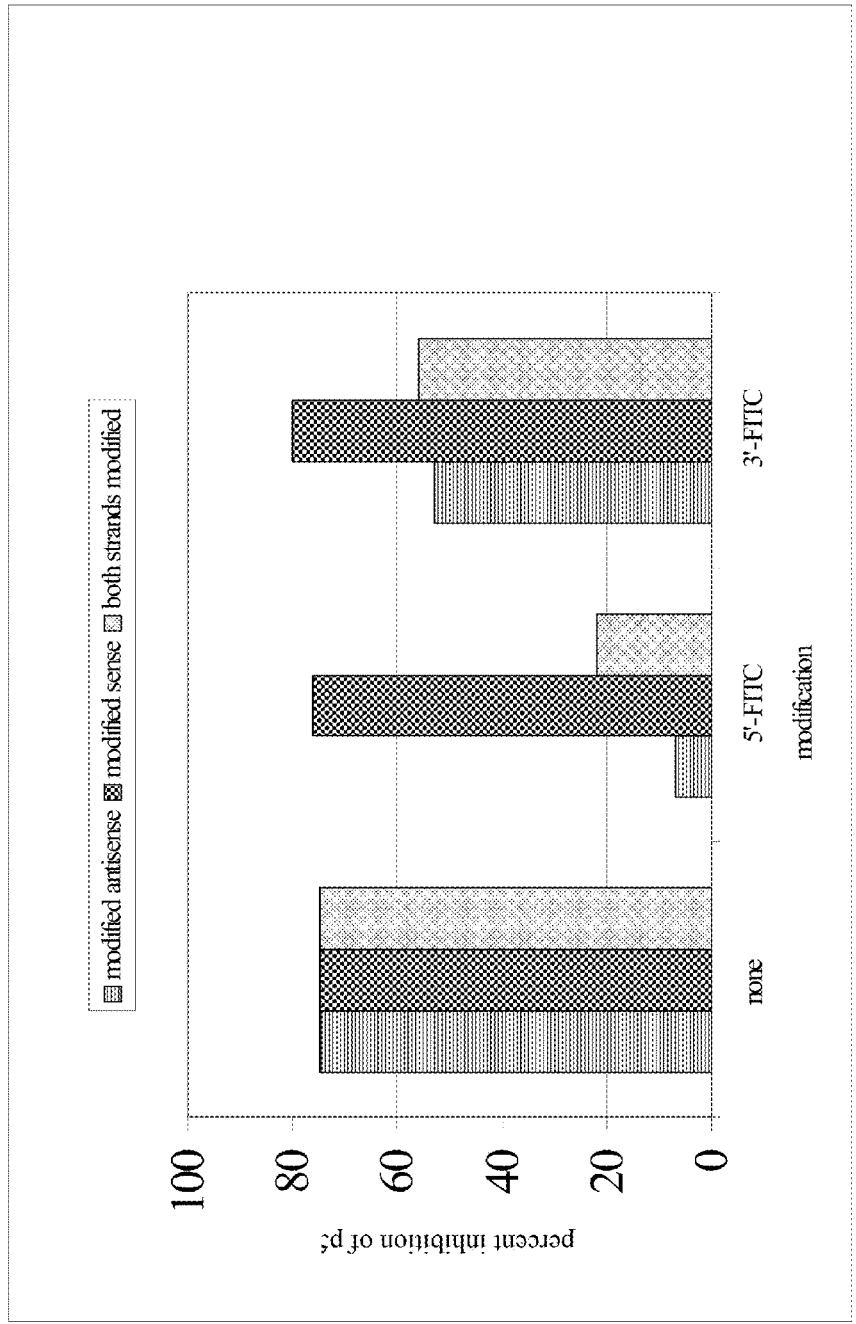
FIG. 16 shows the effect of 5' or 3' modification on activity of double-stranded RNA duplexes.

The Effect of 5' Vs. 3' Modification on the Activity of Double-Stranded Oligonucleotides Oligonucleotide duplexes were modified at either the 3' or 5' end with FITC groups. The modifications were made on either the antisense strand or the sense strand. 5' or 3' modification of the sense strand had no effect on the percent inhibition of p53 mRNA. 3' modification of the antisense strand had little affect on activity, while 5' modification of the antisense strand reduced activity significantly. 3' modification of both strands also had little affect on activity, while 3' and 5' modification of both strands reduced activity. See FIG. 16.

Figure 17:
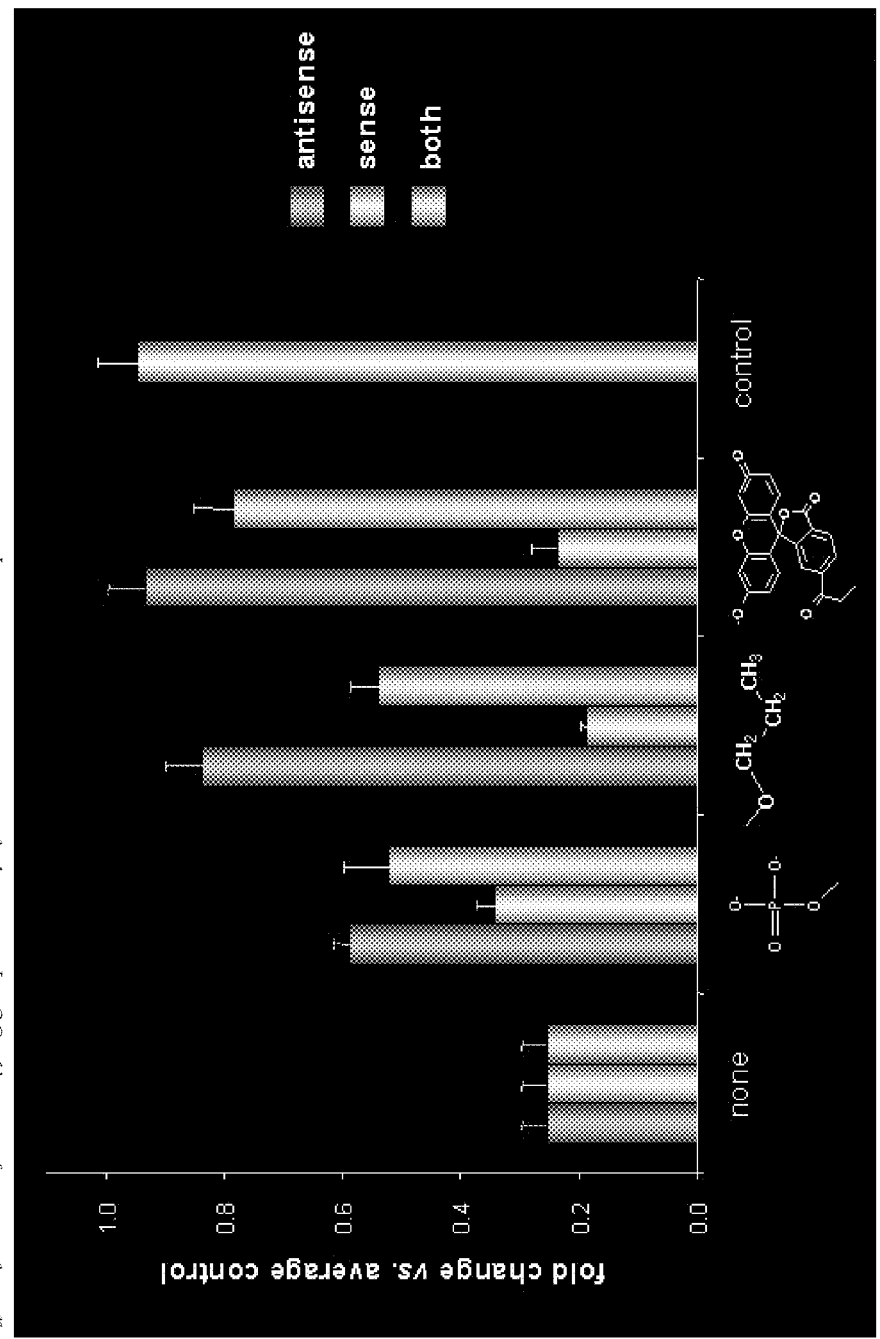
FIG. 17 shows the effect of the size of the modifying group on activity of the double-stranded RNA duplex.

The effect of the size of the group used to modify the 5' end was tested. The results of this experiment are shown in FIG. 17. The inclusion of a 5' phosphate group had little effect on activity, whereas the modification of the antisense strand or both strands had a greater effect. The inclusion of a propyl group had more of an effect, with a 5' propyl group on the antisense strand showing a large reduction in activity; there was also an effect when this group was added to both strands. Similarly, the inclusion of a FITC group at the 5' end of the antisense molecule (or to both molecules) also significantly reduced the activity of the RNA duplex.

Example 5

Comparison of the Efficacy of 2'-O-Methyl Modified and Unmodified Double-Stranded RNA Oligonucleotides A549 cells were transfected with modified or unmodified RNA duplexes complexed at 100 nM with 2 ug/mL LIPOFECTAMINE™ 2000 (Invitrogen) and were transfected for 24

Figure 18:
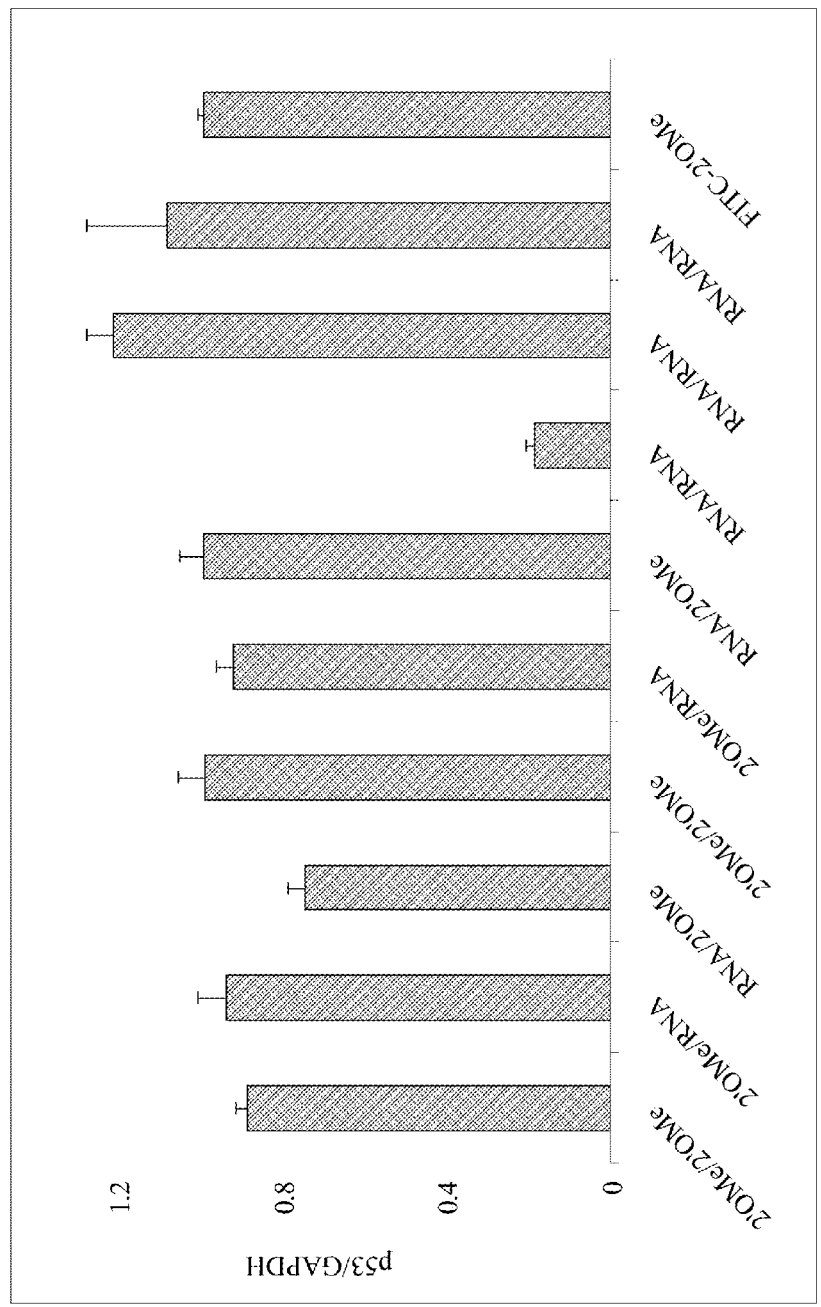
FIG. 18 shows the results of 2'-O-methyl (also referred to herein as "2'-O-Me") modifications on the activity of double-stranded RNA duplexes.

The affect of 2'-O-methyl modifications to one or both strands of a double-stranded RNA molecule is shown in FIG. 18.

Example 6

Toxicity of p53-Targeted siRNAs in A549 Cells 27-mer siRNAs targeting p53 were not toxic to cells when compared to standard 21-mer siRNAs having 3' deoxy TT overhangs. In this experiment, both siRNA constructs inhibited p53 to a similar extent (83% inhibition for 27-mer vs. 90% inhibition for 21-mer). siRNAs were designed to target p53 and were constructed as blunt-end 27-mers or as 21-mers with 3' deoxy TT overhangs. A549 cells were plated at 20,000 cells per well in 48-well plates on the day prior to transfection. On the day of transfection, cells were approximately 60-70% confluent. Cells were transfected with 100 nM siRNAs complexed with 2 ug/mL LIPOFECTAMINE™ 2000 for 24 hours. Following transfection, cells were stained with Dead Red stain to visualize the extent of cell death. The siRNA sequences used were as follows:

```
21-mer with overhangs targeted (5'-3'):
                                    (SEQ ID NO: 21)
ACCUCAAAGCUGUUCCGUCTT
                                    (SEQ ID NO: 22)
GACGGAACAGCUUUGAGGUTT Blunt-end 27-mer targeted (5'-3'):
                                    (SEQ ID NO: 23)
ACGCACACCUCAAAGCUGUUCCGUCCC
                                    (SEQ ID NO: 24)
GGGACGGAACAGCTTTGAGGTGTGCGT
```

Example 7

Toxicity of Blunt-End 27-mer siRNAs Targeting p53 in A549 Cells

The toxicity of targeted blunt-end 27-mer siRNAs targeting p53 was observed to be not significantly different than a control nucleic acid or no treatment. siRNAs were designed to target p53 and were constructed as blunt-end 27-mers. The corresponding control consisted of chemistry-matched, scrambled sequences with a similar base-pair composition. A549 cells were plated at 20,000 cells per well in 48-well plates on the day prior to transfection. On the day of transfection, cells were approximately 60-70% confluent. Cells were transfected with 100 nM siRNAs complexed with 2 ug/mL LIPOFECTAMINE™ 2000 for 24 hours. Following transfection, the cells were stained with Dead Red stain to visualize the extent of cell death. The siRNA sequences used were as follows:

```
Blunt-end 27-mer targeted (5'-3' on top):
                                          (SEQ ID NO: 25)
ACGCACACCUCAAAGCUGUUCCGUCCC
                                          (SEQ ID NO: 26)
GGGACGGAACAGCTTTGAGGTGTGCGT Corresponding control (5'-3' on top):
                                          (SEQ ID NO: 27)
CCCTGCCTTGTCGAAACTCCACACGCA
                                          (SEQ ID NO: 28)
TGCGTGTGGAGTTTCGACAAGGCAGGG
```

Example 8

Toxicity of Blunt End 32-mer siRNAs Targeting p53 in A549 Cells

Similarly, blunt-end 32-mer siRNAs targeting p53 were not observed to be toxic to cells in comparison with a control nucleic acid and no treatment, as determined by Dead Red staining siRNAs were designed to target p53 and were constructed as blunt-end 32-mers. The corresponding control consisted of chemistry-matched, scrambled sequences with a similar base-pair composition. A549 cells were plated at 20,000 cells per well in 48-well plates on the day prior to transfection. On the day of transfection, cells were approximately 60-70% confluent. Cells were transfected with 100 nM siRNAs complexed with 2 ug/mL LIPOFECTAMINE™ 2000 for 24 hours. Following transfection, cells were stained with Dead Red stain to visualize the extent of cell death. The siRNA sequences used were as follows:

```
Targeted blunt-end 32-mer (5'-3' on top:)
                                          (SEQ ID NO: 29)
CCCTCACGCACACCUCAAAGCUGUUCCGUCCC
                                          (SEQ ID NO: 30)
GGGACGGAACAGCTTTGAGGTGTGCGTGAGGG Corresponding control (5'-3' on top):
                                          (SEQ ID NO: 31)
CCCTGCCTTGTCGAAACTCCACACGCACTCCC
                                          (SEQ ID NO: 32)
GGGAGTGCGTGTGGAGTTTCGACAAGGCAGGG
```

Example 9

Inhibition of p53 by 32- and 37-mer Blunt-End siRNAs

Figure 19:
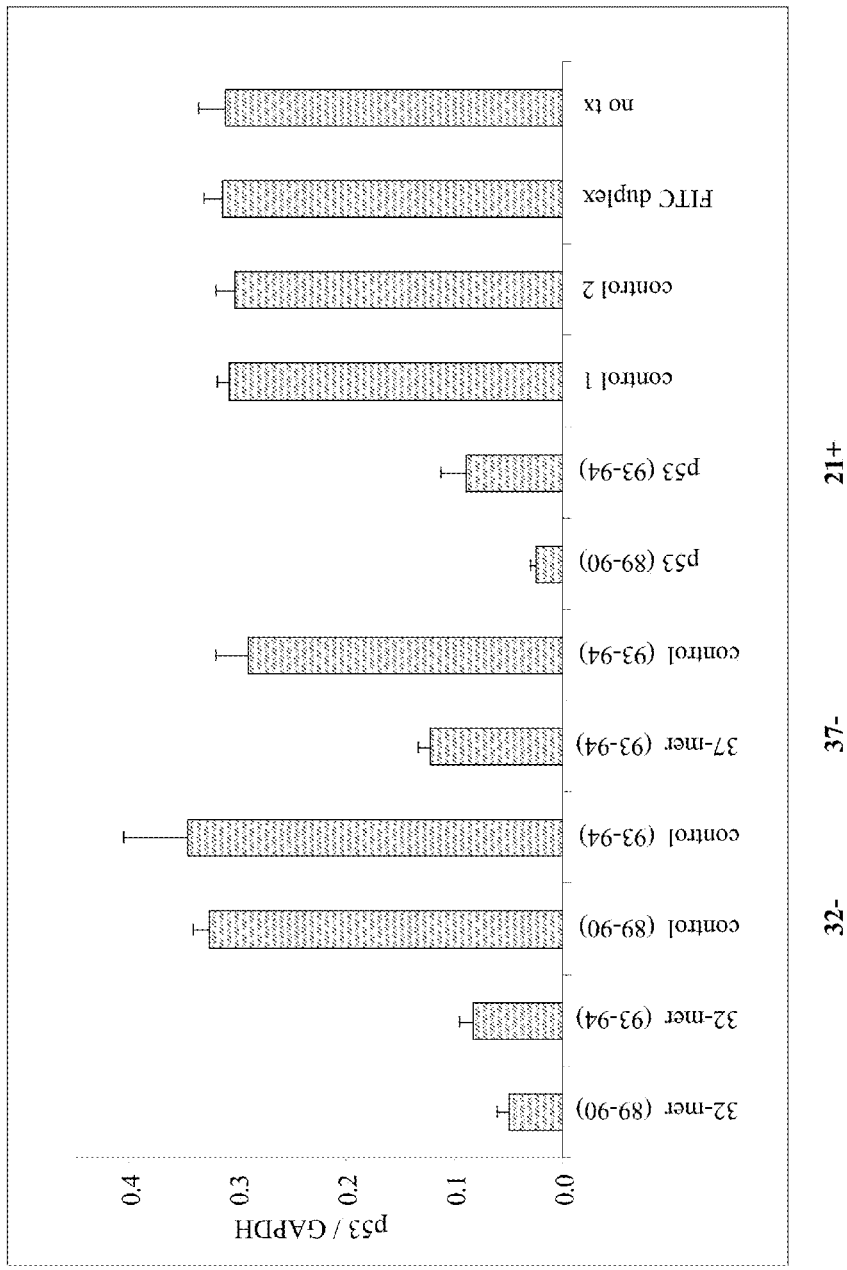
FIG. 19 shows the inhibition of p53 by 32- and 37-mer blunt-end siRNAs.
Figure 20:
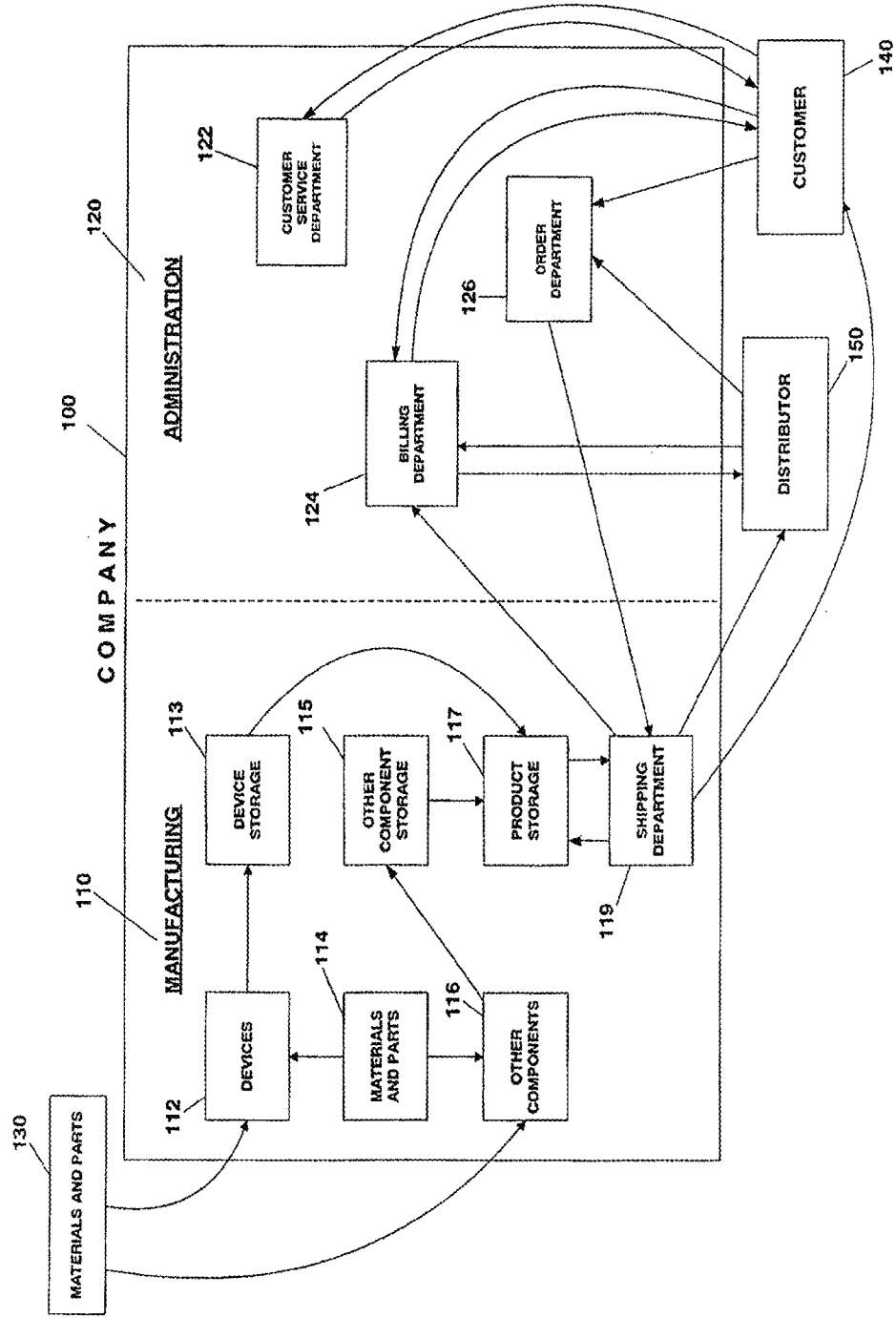
FIG. 20 provides a schematic representation of a system for providing a product to a party such as a customer/purchaser.
Figure 21:
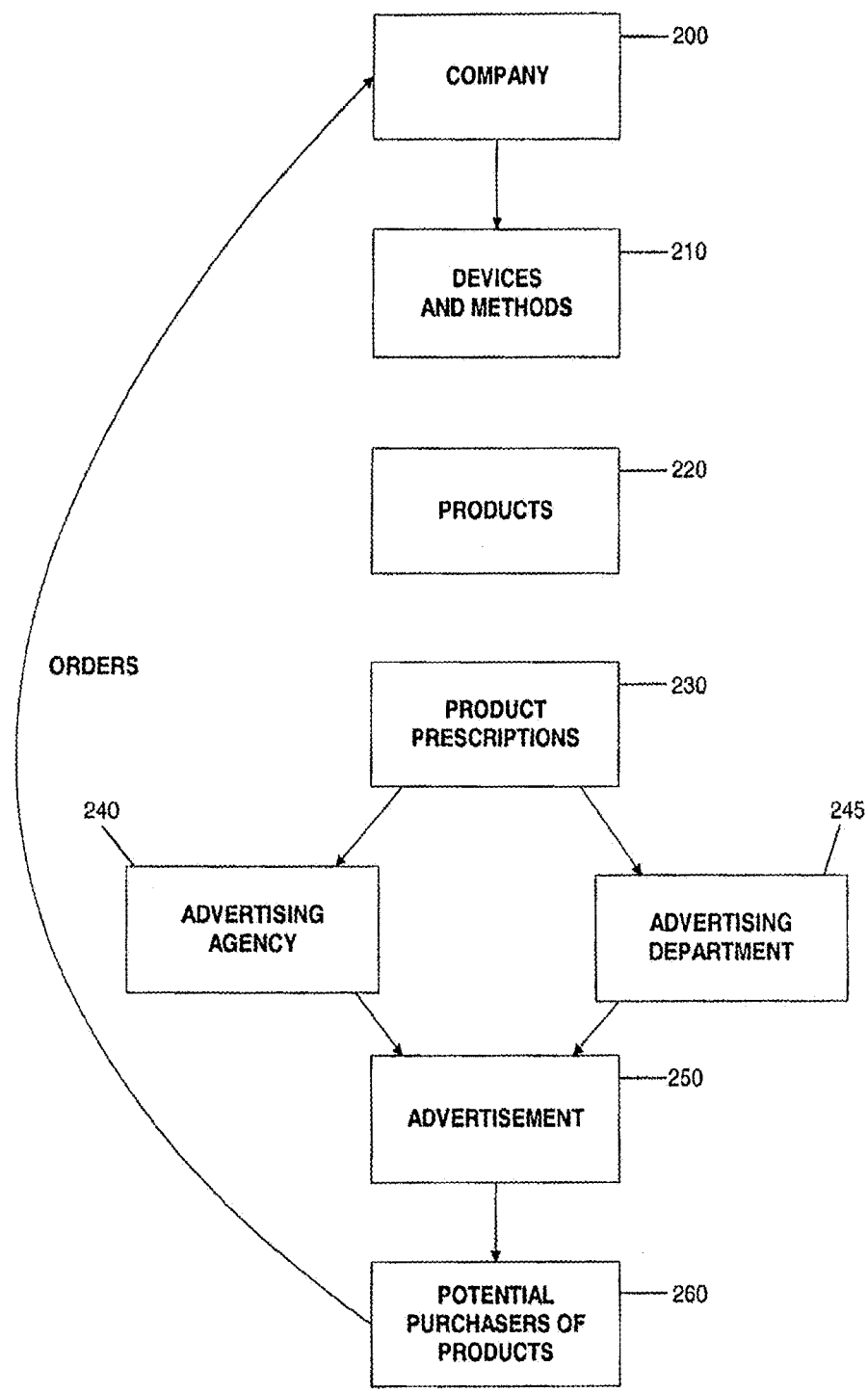
FIG. 21 provides a schematic representation of a system for advising a party as to the availability of a product.

FIG. 19 depicts the results of inhibition of p53 by 32- and 37-mer blunt-end siRNAs in comparison with various control experiments. siRNAs were designed to target each of two sites (93-93 site) and (89-90 site) along the coding region of p53. siRNAs were constructed as blunt-end 32-mers or blunt-end 37-mers. Positive control siRNAs were 21-mers with 3' deoxy TT overhangs. Corresponding controls consisted of chemistry-matched, scrambled sequences with a similar base-pair composition. A549 cells were plated at 20,000 cells per well in 48-well plates on the day prior to transfection. On the day of transfection, cells were approximately 60-70% confluent. Cells were transfected with 100 nM siRNAs complexed with 2 ug/mL LIPOFECTAMINE™ 2000 for 24 hours. Following transfection, cells were lysed and poly(A) mRNA was harvested for RT-PCR Inhibition of p53 expression was determined by quantitative real-time RT-PCR (TaqMan) analysis. Expression of p53 was standardized by quantifying GAPDH for each sample. The data in FIG. 19 represent three separate transfections analyzed in duplicate and normalized to the internal control (GAPDH). The siRNA sequences used were as follows (depicted with the 5'-3' strand on top):

```
Targeted 32-mer (89-90 site):
                                          (SEQ ID NO: 33)
CCCTCACGCACACCUCAAAGCUGUUCCGUCCC
                                          (SEQ ID NO: 34)
GGGACGGAACAGCTTTGAGGTGTGCGTGAGGG 32-mer control (89-90 site):
                                          (SEQ ID NO: 35)
CCCTGCCTTGTCGAAACTCCACACGCACTCCC
                                          (SEQ ID NO: 36)
GGGAGTGCGTGTGGAGTTTCGACAAGGCAGGG 32-mer targeted (93-94 site):
                                          (SEQ ID NO: 37)
CCCUUCUGUCUUGAACAUGAGTTTTTTATGGC
                                          (SEQ ID NO: 38)
GCCATAAAAAACTCATGTTCAAGACAGAAGGG 32-mer control (93-94 site):
                                          (SEQ ID NO: 39)
CGGTATTTTTTGAGTACAAGTTCTGTCTTCCC
                                          (SEQ ID NO: 40)
GGGAAGACAGAACTTGTACTCAAAAAATACCG 37-mer targeted (93-94 site):
                                          (SEQ ID NO: 41)
CCCTTCTGTCTTGAACATGAGTTTTTTATGGCGGGAG
                                          (SEQ ID NO: 42)
CTCCCGCCATAAAAAACTCATGTTCAAGACAGAAGGG 37-mer control (93-94 site):
                                          (SEQ ID NO: 43)
GAGGGCGGTATTTTTTGAGTACAAGTTCTGTCTTCCC
                                          (SEQ ID NO: 44)
GGGAAGACAGAACTTGTACTCAAAAAATACCGCCCTC 21-mer targeted (89-90 site):
                                          (SEQ ID NO: 45)
ACCUCAAAGCUGUUCCGUCTT
                                          (SEQ ID NO: 46)
GACGGAACAGCUUUGAGGUTT 21-mer targeted (93-94 site):
                                          (SEQ ID NO: 47)
CCCUUCUGUCUUGAACAUGTT
                                          (SEQ ID NO: 48)
CAUGUUCAAGACAGAAGGGTT
```

Example 10

Enhanced Cellular Stability of Double-Stranded 2'-O-Methyl RNA

In this example, the single-stranded control oligomer was transfected at 800 nM. Accumulation was observed in the nucleus at 6 hours post transfection, however by 25 hours the fluorescence of the single-stranded oligomer had largely dissipated, indicating the oligomer was no longer intact (Fisher, T., T. Terhorst, et al. (1993). "Intracellular disposition and metabolism of fluorescently-labeled unmodified and modified oligonucleotides microinjected into mammalian cells." *Nucl. Acids Res.* 21:3857-3865). The relative fluorescence of fluorescently-labeled oligomers transfected into A549 cells was observed to fit the following pattern:

| | single-stranded (800 nM) | double-stranded (100 nm) |
|---|---|---|
| 6 h | ++++ | +++++ |
| 25 h | + | +++++ |

The double-stranded oligomer duplex, wherein the second strand was 2'-O-methyl modified RNA, was transfected at 100 nM, and was also clearly visible at 6 hours post transfection. However, in contrast to the single-stranded oligomer, the double-stranded was still largely intact in the nucleus at 24 hours, even though the concentration transfected was 8-fold less, thereby demonstrating that the 2'-O-methyl second strand stabilized the oligomer in the cell.

The oligomers were all 2'-O—$CH_3$ with a phosphodiester backbone containing 6-carboxyfluorescein (6-FAM) tethered to the 5' hydroxyl. The single-stranded control oligomer was transfected at 800 nM complexed with 4 ug/mL of LIPOFECTAMINE™ 2000, and the double-stranded complex was transfected at 100 nM complexed with 1 ug/mL of LIPOFECTAMINE™ 2000.

Uptake of the single and double-stranded oligonucleotides was measured by fluorescent microscopy using an inverted microscope with an excitation wavelength of 494 nm and an emission wavelength of 519 nm. Some aliquots of cells were also stained with Dead Red, a fluorescent reagent that measures the integrity of the cell membrane and thus distinguishes live cells from dead cells. This reagent is excited at a wavelength of 528 nm and emits a red fluorescence at 617 nm. The Dead Red stain was supplied as a 1000× stock solution and was diluted to 1× with Opti-Mem. It was applied to the cells for 20 minutes in a humidified $CO_2$ incubator and then removed and replaced with Opti-Mem. Any background fluorescence can be reduced by rinsing the cells with Opti-Mem and replacing with either full growth media (e.g., DMEM with supplements) or with fresh Opti-Mem before fluorescence microscopy.

Fluorescent signal was seen accumulating in the nucleus at 6 hours post transfection, however by 24 hours the single-stranded oligomer has significantly dissipated, indicating the oligomer is no longer intact. The double-stranded duplexes (wherein the second strand is 2'-O-methyl modified RNA with a 5' 6-FAM) was transfected at 100 nM, and was also clearly visible at 6 hours post transfection. In contrast to the single-stranded oligomer, the double-stranded was still largely intact in the nucleus at 24 hours, even though the concentration transfected was 8-fold less. This experiment demonstrates that the 2'-O-methyl second strand stabilizes the duplex in the cell.

Example 11

Enhanced Stability in Cells and Accumulation in Cytoplasm of RNA Hybridized to 2'-O-Methyl RNA The fluorescence signal, corresponding to uptake of FITC-labeled RNA and 2'-O-methyl modified RNA duplexes, was measured at 6 and 24 hours. RNA complexes were transfected in A549 cells with 100 nM oligomer complexed with 2 ug/mL LIPOFECTAMINE™ 2000 as described below. Cells were continuously transfected for 24 hours and fluorescent uptake was assessed at 6 and 24 hours. Oligomers were 2'-O-methyl modified RNA with 5' 6-FAM (FITC-2'-O-Me), 19-mer RNA with two deoxynucleotides on the 3' end with 5' 6-FAM (FITC-RNA) or 19-mer RNA with two deoxynucleotides on the 3' end (RNA) complexed. At 6 hours, the FITC-2'-O-methyl duplexes show localization in the nucleus and the FITC-2'-O-methyl/RNA and 2'-β-methyl/FITC-RNA complexes show a more diffuse pattern of uptake (these RNA/2'-O-methyl complexes are a substrate for the RISC complex and are therefore retained in the cytoplasm where the RISC complex has been reported to be active). At 24 hours, the FITC-2'-β-methyl/RNA and 2'-O-methyl/FITC-RNA complexes were still visible in the cell, whereas typically not even the single-stranded FITC-2'-O— was visible, even when transfected at significantly higher concentrations, demonstrating that the 2'-O-methyl RNA protects the RNA strand from degradation in the cell.

RNA oligomers having a phosphodiester backbone with 2'-O-methyl nucleotides were synthesized using standard phosphoramidite chemistry. Oligomers were purified by denaturing polyacrylamide gel electrophoresis (PAGE). Purity of oligomers was confirmed by (PAGE) and mass spectrometry. All oligomers were greater than 90% full length, and mass data obtained was consistent with expected values. Target-specific siRNA duplexes consisted of 21-nt sense and 21-nt antisense strands with symmetric 2-nt 3' deoxy TT overhangs. 21-nt RNAs were chemically synthesized using phosphoramidite chemistry. For duplex preparation, sense- and antisense oligomers (each at 50 μM) were combined in equal volumes in annealing buffer (30 mM HEPES pH 7.0, 100 mM potassium acetate, and 2 mM magnesium acetate), heat-denatured at 90° C. for 1 min and annealed at 37° C. for one hour. Duplexes were stored at 80° C. until used.

A549 cells (American Type Culture Collection #CCL-185) were cultured at 37° C. in Dulbecco's Modified Eagle Medium (DMEM, Invitrogen Corporation, cat. no. 11960-044) supplemented with 2 mM L-glutamine, 100 units/mL penicillin, 100 μg/mL streptomycin, and 10% fetal bovine serum (FBS). HeLa cells (American Type Culture Collection #CCL-2) were cultured at 37° C. in Minimal Essential Medium (MEM, Invitrogen Corporation, cat. no. 10370-021) supplemented with 2 mM L-glutamine, 1.5 g/L sodium bicarbonate, 1.0 mM sodium pyruvate, 100 units/mL penicillin, 100 μg/mL streptomycin, and 10% FBS. Cells were passaged regularly to maintain exponential growth. On the day prior to transfection, cells were trypsinized, counted, and seeded in 48-well plates at a density of 20×10³ cells per well in 250 μL fresh media. On the day of transfection cells were typically 60-65% confluent. Transfection of siRNA duplexes and oligomers was carried out using LIPOFECTAMINE™ 2000 (Invitrogen Corporation). Briefly, a 10× stock of LIPOFECTAMINE™ 2000 was prepared in Opti-Mem (Invitrogen Corporation) and incubated at room temperature for 15 minutes. An equal volume of a 10× stock of siRNA duplex or oligomers in Opti-Mem was added and complexation carried out for 15 minutes at room temperature. Complexes were then diluted 5-fold in full growth media. Culture media was removed from each well prior to the addition of 250 μL complexes per well. Cells were incubated at 37° C./5% $CO_2$ for 6 or 24 hours prior to assessing the uptake.

The results of this experiment, as well as the experiment set forth in Example 10 demonstrate that the uptake of the double-stranded oligonucleotides can be measured through the use of a detectable label on either strand or on both strands.

Example 12

Protocol for Transfection of NHAC Cells

NHAC cells are obtained from Clonetics (San Diego, Calif. 92123). On the day prior to transfection, approximately 4.5×10³ NHAC cells are plated in CGM (an NHAC cell culture media obtained from Clontech) in each well of a 24-well plate. At the time of transfection, the cells are preferably between about 70-80% confluent. A 30 μg/ml, 10× stock of LIPOFECTAMINE™ 2000 in Opti-Mem, a serum-free medium is prepared. This solution is allowed to stand at room temperature for at least 15 minutes prior to use. STEALTH™ RNA molecules which are 25 nucleotides in length are used to transfect NHAC cells are prepared as a 3 μM, 10× stock in Opti-Mem. Equal volumes of the 10× LIPOFECTAMINE™ 2000 and 10× STEALTH™ RNA oligonucleotide stocks are then added and allowed the mixture to incubate for 15 minutes to allow for complexation. This mixture is then diluted with 4 volumes of CGM medium (Clontech) to form the final 1× (300 nM STEALTH™ RNA oligonucleotide complexed with 3 μg/ml LIPOFECTAMINE™ 2000) solution for transfection.

Prior to transfection, all media is aspirated from the NHAC cells growing in the 24-well plate. 0.5 ml of the 1× lipid/STEALTH™ RNA complex is added to each well, being careful not to let the cells dry out during the change of media. The cells are then incubated for 16-24 hours at 37° C. in a humidified $CO_2$ incubator. The cells are then harvested, centrifuged to obtain a cell pellet and analyzed for protein determination or RNA isolation.

Example 13

Protocol for Transfection of THP-1 Cells by Electroporation

THP-1 cells are maintained in RPMI 1640 media containing 4.5 g/L glucose, 10% FBS, 2 mM L-glutamine, 1.5 g/L sodium bicarbonate, 10 mM HEPES, 1 mM sodium pyruvate, $5×10^{-5}$M 2-mercaptoethanol and Pen/Strep. The cells are split 1:3 twice a week to maintain a cell concentration of $1-2×10^6$ cells/ml.

On the day prior to electroporation, THP-1 cells are seeded at $0.5×10^6$/ml. The cells are collected by centrifugation on the next day and the cell pellet washed in PB-sucrose (70 ml 0.1M sodium phosphate buffer, 272 ml of 1 M sucrose, 1 ml of 1M $MgCl_2$ and 657 ml water using sterile and endotoxin-free solutions). 15 ml of PB-sucrose is used for every 50 ml of culture that is started with. The cells are again centrifuged and re-washed with PB-sucrose. The cells are then counted and centrifuged again. The cell pellet is resuspended in PB-sucrose at a concentration of $15×10^6$ cells/ml.

For electroporation, 5 μl of a 1 mM stock of STEALTH™ RNA oligonucleotide is added to a sterile tube. To this 100 μl of the finally resuspended THP-1 cells is added and mixed gently. The cells and STEALTH™ RNA oligonucleotide are then transferred to a sterile 0.1 cm gap electroporation cuvette and electroporated using a BioRad GENEPULSERII™ with RF module at a setting of: 100 volts, 100% modulation, 25 kHz frequency, 2 msec burst duration×10 bursts with a burst interval of 100 msec. Following electroporation, the cuvette is tapped to suspend any settled cells and applied on additional burst at the above settings. The cuvette is again taped gently immediately after the pulse to avoid any pH gradients and 1.5 ml of warm RPMI 164 media (described above) was added. The cells are then transferred into 2 wells of a 24-well plate (0.7 ml/well) for recovery. The cells are incubated at 37° C. for 24 hours, pelleted, and rinsed with Opti-Mem to remove any excess STEALTH™ RNA oligonucleotide. The cells can then be examined for STEALTH™ RNA oligonucleotide uptake (if the STEALTH™ RNA oligonucleotide comprises a detectable moiety) and can be lysed for RNA isolation or protein determination.

Example 14

Protocol for Transfection of B6 and C3H Endothelial Cells

B6 or C3H cells are grown to confluence in either a 96- or 48-well plate. This is typically achieved by plating B6 cells at $2×10^4$ cells/well in 50 μl of DMEM media (5 ml FBS, 45 mg heparin, 6 ml of 5 mg/ml ECGF, 5 ml of Antibiotic-Antimycotic (Invitrogen, Carlsbad, Calif.) and DMEM to a final volume of 500 ml) for 96 well plates or $6×10^4$ cells/well in 250 μl of DMEM media for 48 well plates. C3H cells are initially plated at $3×10^4$ cells/well in 50 μl DMEM media for 96 well-plates or $6×10^4$ cells/well in 250 μl of DMEM media for 48 well plates. Initial platings are done 2 days prior to transfection.

On the day of transfection, EPEI is diluted to a final concentration of 5 μM in water to create a 20× stock. A 40 μg/ml 20× stock of LIPOFECTAMINE™ 2000 is also made by mixing 80 μl of LIPOFECTAMINE™ 2000 with 2 liters of OptiMem. A 2 μM, 10× stock of a STEALTH™ RNA oligonucleotide is prepared in OptiMem. Each of the stock solutions is allowed to sit at room temperature for 15 minutes. 42.5 μl each of the EPEI and LIPOFECTAMINE™ 2000 stocks is then mixed with 85 μl of STEALTH™ RNA oligonucleotide stock and allowed them to complex for 15 minutes at room temperature. After complexing, the mixture is diluted by adding 680 μl of Opti-Mem. 50 μl of the complexed STEALTH™ RNA oligonucleotide is then added to each well containing either B6 or C3H cells and incubated the cells for 2-3 hours at 37° C. 5% $CO_2$. The media is then aspirated off and 50 or 250 μl (depending upon whether the cells are in 48- or 96-well plates) of DMEM medium containing 1% FBS is added and the cells are incubated overnight.

The following day, the cells are stimulated by the addition of 2 μg/ml LPS in 1% FBS for 6 hours. Following LPS stimulation, the cells can be lysed for RNA extraction and protein determination.

Example 15

Exemplary Product Literature of the Invention

The text of exemplary product literature for various embodiments of double-stranded oligonucleotides of the invention are disclosed below. This product literature contains descriptions of kits of the invention and includes instructions for use of kits of the invention, and exemplary kit components. This exemplary product literature is particularly useful for practicing various aspects of business methods of the invention. Suitable methods and compositions of the invention are described in the product literature for the BLOCK-iT™ Fluorescent Oligo, BLOCK-iT™ Transfection Optimization Kit, and Stealth™ RNA, all of which are available from Invitrogen Corporation, Carlsbad, Calif.

BLOCK-iT™ Fluorescent Oligo

The BLOCK-iT™ Fluorescent Oligo is a fluorescein isothiocyanate (FITC)-labeled dsRNA oligomer designed for use in RNAi analysis to facilitate assessment and optimization of cationic lipid-mediated delivery or electroporation of dsRNA oligonucleotides into mammalian cells. Using the BLOCK-iT™ Fluorescent Oligo in RNAi studies offers the following advantages: (1) provides a good indication of the transfection efficiency with Invitrogen's Stealth™ RNA, standard unmodified siRNA, or purified Dicer-generated siRNA; and (2) allows strong, easy fluorescence-based indication of transfection efficiency in every RNAi experiment. The BLOCK-iT™ Fluorescent Oligo is supplied as a 20 μM or 1 mM stock of FITC-labeled double-stranded RNA (dsRNA) oligomer in 100 mM KOAc, 30 mM HEPES-KOH, pH 7.4, and 2 mM MgOAc. Upon receipt, the BLOCK-iT™ Fluorescent Oligo should be stored at −20° C., and protected from light.

The BLOCK-iT™ Fluorescent Oligo is a FITC-labeled, double-stranded RNA duplex with the same length, charge, and configuration as standard siRNA, and contains chemical modifications that enhance the stability and allow assessment of fluorescence signal for a significantly longer time period than is obtained with other unmodified, fluorescently labeled RNA. For example, fluorescence signal is readily detectable in HEK293 cells for at least 72 hours. Note that the strength of the fluorescence signal depends on the transfection efficiency, growth rate of the cells, and the amount of oligomer transfected. The sequence of the BLOCK-iT™ Fluorescent Oligo is not homologous to any known gene, ensuring against induction of non-specific cellular events caused by introduction of the Oligo into cells. The Oligo also localizes primarily to the nucleus upon uptake (Fisher et al. 1993. *Nuc. Acids Res.* 21:3857-3865). Importantly, the BLOCK-iT™ Fluorescent Oligo is designed strictly for use as a tool for Stealth™ RNA or siRNA uptake assessment, and is not meant to provide any information about the behavior of a Stealth™ RNA or siRNA, including its cellular localization, half-life, or stability.

The BLOCK-iT™ Fluorescent Oligo is supplied as a 20 μM or 1 mM stock solution in an annealing buffer. The guidelines below should be followed when handling the BLOCK-iT™ Fluorescent Oligo stock solution:
1. The BLOCK-iT™ Fluorescent Oligo is light sensitive. Store the stock solution at −20° C., protected from light. The stock solution is stable for at least 6 months if stored properly.
2. When using, thaw the stock solution on ice or at room temperature. Once thawed, place the tube on ice until use. After use, return stock solution to −20° C. storage.
3. The stock solution may be frozen and thawed multiple times without loss of fluorescence signal if handled properly.
4. Take precautions to ensure that the stock solution does not become contaminated with RNase.
   a. Use RNase-free sterile pipette tips and supplies for all manipulations.
   b. Wear gloves when handling reagents and solutions.

The BLOCK-iT™ Fluorescent Oligo (20 μM or 1 mM stock) may be used with any cationic lipid-based transfection reagent suitable for delivery of Stealth™ RNA, siRNA, and Dicer-generated siRNA to mammalian cells. For example, Lipofectamine™ 2000 Reagent (Invitrogen Corp., Carlsbad, Calif.) provides for highly efficient transfection of a wide variety of mammalian cells with the BLOCK-iT™ Fluorescent Oligo (Ciccarone et al. 1999. *Focus* 21:54-55). The guidelines below should be followed when transfecting the BLOCK-iT™ Fluorescent Oligo:
1. The amount of BLOCK-iT™ Fluorescent Oligo to use depends on the growth rate and transfection efficiency of the mammalian cells. When transfecting a mammalian cell line for the first time, evaluate several concentrations of lipid and vary the final concentration of the BLOCK-iT™ Fluorescent Oligo from 10 to 200 nM to determine the optimal amount of BLOCK-iT™ Fluorescent Oligo to use to obtain a strong fluorescence signal. For most cell lines tested (e.g. HEK293, A549, HeLa), w a readily detectable fluorescence signal was obtained when using 100 nM BLOCK-iT™ Fluorescent Oligo for transfection.
2. Prepare and seed mammalian cells at a density recommended by the manufacturer of the transfection reagent being used.
3. Prepare lipid-BLOCK-iT™ Fluorescent Oligo complexes as directed by the manufacturer of the transfection reagent being used. Always dilute the BLOCK-iT™ Fluorescent Oligo immediately before transfection (i.e. do not store diluted Oligo) and into an appropriate medium. For example, the BLOCK-iT™ Fluorescent Oligo may be diluted into Opti-MEM® I Reduced Serum Medium (Invitrogen Corp., Carlsbad, Calif.).
4. Assess fluorescent uptake at 6 to 24 hours post-transfection. The fluorescence signal may be detected at longer time points depending on the transfection efficiency and growth rate of the cells.

When performing electroporation, higher concentrations of BLOCK-iT™ Fluorescent Oligo may be required. Use the 1 mM stock solution of BLOCK-iT™ Fluorescent Oligo to optimize electroporation conditions according to the manufacturer's guidelines.

Once the mammalian cells have been transfected or electroporated with the BLOCK-iT™ Fluorescent Oligo, Oligo uptake in live cells may be qualitatively assessed using fluorescence microscopy. Any type of fluorescence microscope and any standard FITC filter set ($\lambda_{ex}$=494 nm, $\lambda_{em}$=519 nm green) may be used for detection.

BLOCK-iT™ Transfection Optimization Kit

The BLOCK-iT™ Transfection Optimization Kit is designed to facilitate optimization of transfection conditions for RNAi studies. The kit provides the following reagents:
1. BLOCK-iT™ Fluorescent Oligo (20 μM FITC-labeled double-stranded RNA (dsRNA) oligomer in annealing buffer) for use as an indicator of transfection efficiency in RNAi experiments with Stealth™ RNA or siRNA.
2. A Stealth™ RNA molecule (20 μM p53 Positive Control Stealth™ RNA in annealing buffer) targeting the human p53 gene for use as a positive control (in human cell lines only) for the RNAi response.
3. A Scrambled Stealth™ RNA molecule (20 μM Scrambled Negative Control Stealth™ RNA in annealing buffer) for use as a negative control (in human cell lines only) for the RNAi response.
4. Dead Cell Reagent (2 mM Ethidium homodimer-1 (EthD-1) in DMSO/$H_2O$ 1:4 (v/v)) to assess cell viability.

The annealing buffer is composed of 100 mM KOAc, 30 mM HEPES-KOH, pH 7.4, and 2 mM MgOAc. Upon receipt, each of the above reagents should be stored at −20° C., and the BLOCK-iT™ Fluorescent Oligo and Dead Cell Reagent should be protected from light. All reagents in stock solutions are stable for at least 6 months when stored properly.

The BLOCK-iT™ Fluorescent Oligo and the Dead Cell Reagent in the BLOCK-iT™ Transfection Optimization Kit can be used in RNAi studies to help optimize transfection conditions for transfecting Stealth™ RNA or siRNA into a mammalian cell line of interest for the first time. The BLOCK-iT™ Fluorescent Oligo allows strong, easy fluorescence-based assessment of dsRNA oligomer uptake into mammalian cells. The BLOCK-iT™ Fluorescent Oligo is functionally qualified by transient transfection into mammalian cells and assessment of fluorescence signal at 24 hours post-transfection.

Dead Cell Reagent is intended for use as an indicator of cell viability following transfection of mammalian cells with Stealth™ RNA or siRNA, and is an ethidium dye (ethidium homodimer-1; EthD-1) with the following characteristics: (1) Molecular formula: $C_{46}H_{50}Cl_4N_8$; and (2) Molecular weight: 856.77. Dead Cell Reagent, which is excluded by the intact plasma membrane of live cells, enters cells with damaged membranes and emits a red fluorescence signal upon binding to nucleic acids ($\lambda_{ex}$=528 nm, $\lambda_{em}$=617 nm). The fluorescence signal is detectable using a fluorescence microscope and filters for propidium iodide or Texas Red®. Once the optimal conditions to use for transfection of a given cell line have been determined, the BLOCK-iT™ Fluorescent Oligo and the Dead Cell Reagent may be used in every RNAi experiment with that cell line as an indicator of transfection efficiency and cell viability.

Stealth™ RNAi is chemically modified dsRNA developed to overcome the limitations of traditional siRNA. Using Stealth™ RNA for RNAi analysis offers the following advantages: (1) obtain effective target gene knockdown at levels that are equivalent to or greater than those achieved with traditional siRNA; (2) reduces non-specific effects caused by induction of cellular stress response pathways; and (3) exhibits enhanced stability for greater flexibility in RNAi analysis. The BLOCK-iT™ Transfection Optimization Kit includes a p53 and a Scrambled Stealth™ RNA molecule for use as positive and negative controls, respectively, in an RNAi experiment targeting the human p53 gene. If the mammalian cell line of interest is a human cell line that expresses p53, the p53 and Scrambled Stealth™ RNA oligomers may be used as positive and negative controls for the RNAi response, and to help optimize transfection conditions. The p53 and Scrambled Stealth™ RNA oligomers are functionally qualified by transient transfection into A549 cells. At 24 hours post-transfection, mRNA is isolated from treated and untreated cells using the mRNA Catcher™ Kit, and qRT-PCR is performed using LUX™ primers for the human p53 gene. qRT-PCR analysis must demonstrate >75% inhibition of human p53 expression levels in p53 Stealth™ RNA-treated cells and no inhibition in Scrambled Stealth™ RNA-treated cells.

To properly handle the reagents of the BLOCK-iT™ Transfection Optimization Kit, the stock solutions of the BLOCK-iT™ Fluorescent Oligo and the Stealth™ RNA molecules should be thawed on ice or at room temperature. Once thawed, the tubes should be placed on ice until use. After use, the stock solution should be returned to −20° C. storage. The stock solution may be frozen and thawed multiple times without loss of fluorescence signal (BLOCK-iT™ Fluorescent Oligo) or activity (Control Stealth™ RNAi oligomers) if handled properly. Precautions must be taken when working with these reagents to ensure that the stock solutions do not become contaminated with RNase. For example, RNase-free sterile pipette tips and supplies should be used for all manipulations, and gloves worn when handling the reagents. To properly handle the Dead Cell Reagent, the stock solution should be thawed at room temperature. To mix the stock solution, tap the tube, and centrifuge briefly before opening. After use, return stock solution to −20° C. storage. The stock solution may be frozen and thawed multiple times without loss of fluorescence signal if handled properly.

Any suitable cationic lipid-based transfection reagent may be used to deliver Stealth™ RNA or siRNA to mammalian cells. General guidelines are provided below for using the reagents supplied in the BLOCK-iT™ Transfection Optimization Kit to help optimize transfection conditions for Stealth™ RNA or siRNA and mammalian cell lines. For example, the Lipofectamine™ 2000 Reagent (Invitrogen Corp., Carlsbad, Calif.) is optimal for highly efficient delivery of Stealth™ RNA or siRNA to a wide variety of mammalian cells (Gitlin et al., 2002. Nature 418:430-34; Yu et al., 2002. Proc. Natl. Acad. Sci. USA 99:6047-6052). To perform a transfection, first determine the appropriate amount of each reagent to use such that fluorescence signal (BLOCK-iT™ Fluorescent Oligo or Dead Cell Reagent) or gene knockdown effect (p53 Stealth™ RNA) is readily detectable.

The amount of BLOCK-iT™ Fluorescent Oligo used to transfect a mammalian cell line depends on the growth rate and transfection efficiency of the mammalian cells. To optimize transfection conditions, evaluate several concentrations of lipid and vary the final concentration of the BLOCK-iT™ Fluorescent Oligo from 10 to 200 nM to determine the optimal amount of Oligo required to obtain a strong fluorescence signal. A concentration of 100 nM BLOCK-iT™ Fluorescent Oligo is a recommended starting point.

The amount of p53 Stealth™ RNA to transfect to achieve optimal gene knockdown needs to be determined experimentally for each human cell line. To optimize transfection conditions, evaluate several concentrations of lipid and vary the final concentration of Stealth™ RNA from 10 to 100 nM to determine the conditions required for the optimal levels of gene knockdown. Use of higher concentrations of Stealth™ RNA may be possible depending on the cell line. A concentration of 40 nM p53 Stealth™ RNA is a recommended starting point. The same concentration of the negative control Scrambled Stealth™ RNA should be used.

The transfection experiment may be set up to allow for simultaneous assessment of transfection efficiency and cell viability with the same sample by transfecting one set of cells with the BLOCK-iT™ Fluorescent Oligo, then staining those cells with the Dead Cell Reagent at a suitable time period after transfection (generally 6 to 24 hours post-transfection). Prepare and seed cells at a density recommended by the manufacturer of the transfection reagent being used. Also prepare lipid-oligomer complexes as directed by the manufacturer of the transfection reagent being used. The BLOCK-iT™ Fluorescent Oligo or Stealth™ RNA should be diluted immediately before transfection (i.e. do not store diluted oligomer) and into an appropriate medium, for example, Opti-MEM® I Reduced Serum Medium (Invitrogen Corp., Carlsbad, Calif.).

The following procedure may be used to stain cells with Dead Cell Reagent. First, prepare a sufficient amount of the working solution based on the number of samples that will be stained. For example, 2 mls/well of staining solution should be prepared for a 6-well culture vessel; 1 ml/well of staining solution should be prepared for a 12-well culture vessel; 0.5 ml/well of staining solution should be prepared for a 24-well culture vessel; and 0.25 ml/well of staining solution should be prepared for a 48-well culture vessel. To prepare the working solution, thaw the 2 mM Dead Cell Reagent stock solution at room temperature. Tap the tube to mix, and centrifuge briefly before opening. Dilute the appropriate amount of Dead Cell Reagent into Opti-MEM® I Reduced Serum Medium to prepare a 2 µM working solution (1:1000 dilution). For example, to prepare 1 ml of a 2 µM working solution, add 1 μl of Dead Cell Reagent to 1 ml of Opti-MEM® I Reduced Serum Medium. Aspirate the media from the cells and replace with the appropriate volume of Dead Cell Reagent. Incubate the cells at 37° C. in a $CO_2$ incubator for 10-15 minutes, and then remove the Dead Cell Reagent and replace with fresh Opti-MEM® I Reduced Serum Medium.

After the mammalian cells have been transfected with the BLOCK-iT™ Fluorescent Oligo and stained with Dead Cell Reagent, Oligo uptake and cell viability may be qualitatively assessed using any fluorescence microscope and the following filter sets. To assess transfection efficiency, use any standard FITC filter set ($\lambda_{ex}$=494 nm, $\lambda_{em}$=519 green) to detect the fluorescence signal from the BLOCK-iT™ Fluorescent Oligo. To assess cell viability, use a filter set for propidium iodide or Texas Red® ($\lambda_{ex}$=528 nm, $\lambda_{em}$=617 nm) to detect the fluorescence signal from the Dead Cell Reagent.

When the positive control Stealth™ RNA and the negative control scrambled Stealth™ RNA are transfected into a mammalian cell line, any method of choice may be used to detect human p53 expression levels. One exemplary method for assaying p53 mRNA levels is quantitative RT-PCR (qRT-PCR) using Invitrogen's custom LUX™ primers. The LUX™ Designer available at www.invitrogen.com/lux may be used to help design and order suitable primers to use for the qRT-PCR analysis. Invitrogen's mRNA Catcher™ Kit may be used to prepare mRNA from treated or untreated cells. When performing qRT-PCR, an internal control RNA (e.g. β-actin, GAPDH, or cyclophilin) should be used to normalize results. Alternatively or in addition, Western blot analysis using a suitable antibody to human p53 may be used to assay for p53 protein levels. The half-life of the protein should be taken into account when assessing RNAi effects at the protein level.

Transfecting Stealth™ RNA or siRNA into Mammalian Cells Using Lipofectamine™ 2000

As described above, Lipofectamine™ 2000 Reagent is a proprietary formulation that facilitates highly efficient delivery of Stealth™ RNA molecules or short interfering RNA (siRNA) to mammalian cells for RNAi analysis. Below are general guidelines and a procedure to transfect Stealth™ RNA or siRNA oligomers into mammalian cells using Lipofectamine™ 2000. Recommended reagent amounts are provided as a starting point. Transfection conditions for the mammalian cell line and target gene used should be optimized as described above for best results.

Many factors can influence the degree to which expression of a gene of interest is reduced (i.e. gene knockdown) in an RNAi experiment including, but not limited to, transfection efficiency, transcription rate of the gene of interest, protein stability, efficacy of the particular Stealth™ RNAi or siRNA sequence chosen, and growth characteristics of the mammalian cell line. Take these factors into account when designing transfection and RNAi experiments. For more tips to help achieve success in RNAi experiments, refer to the section below entitled "Seven Steps to RNAi Success."

The following general guidelines will help optimize success when transfecting Stealth™ RNA or siRNA into mammalian cells using Lipofectamine™ 2000. Preferably the mammalian cell line of interest used in the transfection experiments consists of low-passage cells that are healthy, with greater than 90% viable before transfection. The amount of Stealth™ RNA molecules or siRNA to transfect to achieve optimal gene knockdown needs to be determined experimentally for each cell line. The Stealth™ RNA molecules or siRNA of interest may be suspended in annealing buffer at a concentration of 20 μM. For example, the BLOCK-iT™ Fluorescent Oligo may be used to help optimize transfection conditions for a cell line as described above. Once the optimal conditions to use for transfection have been determined, the BLOCK-iT™ Fluorescent Oligo may be included in every experiment as an indicator of transfection efficiency.

If the mammalian cell line is being transfected for the first time, evaluate several concentrations of Lipofectamine™ 2000 and vary the final concentration of Stealth™ RNA or siRNA from 20 to 100 nM to determine the conditions required to achieve the optimal levels of gene knockdown. Transfecting 40 nM of Stealth™ RNA or siRNA is a good starting point. Higher concentrations of Stealth™ RNA or siRNA may be possible depending on the cell line. Transfect cells at 30-50% confluence. Gene knockdown levels are generally assayed at a minimum of 24 to 72 hours following transfection. Transfecting cells at a lower density allows a longer interval between transfection and assay time, and minimizes the loss of cell viability due to cell overgrowth. Depending on the nature of the target gene, transfecting cells at higher densities may be suitable with optimization of conditions. Do not add antibiotics to the medium during transfection as this reduces transfection efficiency and causes cell death. Finally, for optimal results, use Opti-MEM® I Reduced Serum Medium (pre-warm to 37° C. before use) to dilute Lipofectamine™ 2000 and Stealth™ RNA or siRNA oligomers prior to complex formation.

The following procedure may be used to transfect Stealth™ RNA or siRNA oligomers into mammalian cells using Lipofectamine™ 2000. The Table below shows appropriate reagent amounts and volumes to add for different tissue culture formats. Use the recommended amounts of Stealth™ RNA or siRNA (see column 4) and Lipofectamine™ 2000 (see column 6) as a starting point, and optimize conditions for the cell line and Stealth™ RNA or siRNA of interest (Note: 20 μM Stealth™ RNA or siRNA=20 pmol/μl.).

| Culture Vessel | Relative Surface Area (vs. 24-well) | Volume of Plating Medium (μl) | Stealth ™ RNA or siRNA (pmol) and Dilution Volume (μl) | Stealth ™ RNA or siRNA Amounts (pmol) for Optimization | Lipofectamine ™ 2000 (μl) and Dilution Volume (μl) | Lipofectamine ™ 2000 Amounts (μl) for Optimization |
|---|---|---|---|---|---|---|
| 48-well | 0.4 | 200 μl | 10 pmol in 25 μl | 2-25 pmol | 0.5 μl in 25 μl | 0.3-0.8 μl |
| 24-well | 1 | 500 μl | 20 pmol in 50 μl | 10-50 pmol | 1 μl in 50 μl | 0.5-1.5 μl |
| 6-well | 5 | 2 ml | 100 pmol in 250 μl | 50-250 pmol | 5 μl in 250 μl | 2.5-6 μl |

To begin, one day before transfection, plate cells in the appropriate amount of growth medium without antibiotics such that they will be 30-50% confluent at the time of transfection. For each transfection sample, prepare oligomer-Lipofectamine™ 2000 complexes as follows: (1) dilute Stealth™ RNA or siRNA oligomer in the appropriate amount of Opti-MEM® I Reduced Serum Medium without serum and mix gently; (2) mix Lipofectamine™ 2000 gently before use, dilute the appropriate amount in Opti-MEM® I Reduced Serum Medium, mix gently and incubate for 5 minutes at room temperature; (3) after the 5-minute incubation, combine the diluted oligomer with the diluted Lipofectamine™ 2000, mix gently and incubate for 20 minutes at room temperature to allow complex formation to occur. Note that the solution may appear cloudy, but this will not inhibit transfection. Add the oligomer-Lipofectamine™ 2000 complexes to each well containing cells and medium. Mix gently by rocking the plate back and forth. Finally, incubate the cells at 37° C. in a $CO_2$ incubator for 24-96 hours as appropriate and then assay for gene knockdown. It is not necessary to remove the complexes or change the medium; however, growth medium may be replaced after 4-6 hours without loss of transfection activity.

The Table below shows optimal reagent amounts and volumes for a variety of cell lines evaluated:

| Cell Line | Species | Type | Description | Opt. Duplex Conc. | Optimal Lipid Conc. | Duplex Range | Lipid Range |
|---|---|---|---|---|---|---|---|
| A549 | human | adherent | lung carcinoma | 100 nM | 2 ug/ml L2K | | |
| HeLa | human | adherent | cervical adenocarcinoma | 50 Nm | 1 ug/ml L2K | | |
| MC3T3 | mouse | adherent | fibroblast | | | 1-100 nM | 1-3 ug/ml Lipofectamine 2000 (L2K) |
| 3T3-L1 (Undifferentiated) | mouse | adherent | fibroblast | 100 nM | 2 ug/ml L2K | | |
| NRK | rat | adherent | normal rat kidney | 200 nM | 2 ug/ml L2K | | |
| RAT 1 | rat | adherent | fibroblast | 200 nM | 2 ug/ml L2K | | |
| HUVEC | human | adherent | endothelial | 300 nM | 1:125 dilution of Oligofectamine | | |
| HMVEC | human | adherent | microvascularen dothelial | 200 nM | 2 ug/ml L2K | | |
| HEK 293 | human | adherent | fetal kidney | 200 nM | 2 u/lml L2K | | |
| HepG2 | human | adherent | hepatocyte | 300 nM | 2 ug/ml L2K (while plating) | | |
| MSC | human | adherent | Mesenchymal stem cells | 400 nM | 2 ug/ml L2K | 100-400 nM | |
| SK-N-SH | human | adherent | neuroblastoma | 300 nM | 3 ug/ml L2k | | |
| Keratinocytes | human | adherent | primary keratinocytes | 100 nM | 2 ug/ml L2K | 10-200 nM | 2-3 ug/ml L2K |
| Sebocytes | human | adherent | primary sebocytes | 100 Nm | 3 ug/ml L2K | | |
| Melanocytes | human | adherent | primary melanocytes | | | 0.25-1 ug duplex/well | 1-3 u/l Mirus TKO/ug duplex (Mirus, Madison, WI, Cat No. MIR 2154) |
| HCT 116 | human | adherent | colorectal carcinoma | 400 nM | 4 ug/ml | 200-800 nM | 2-4 ug/ml |
| HNAC | human | adherent | cartilage | 300 nM | 3 ug/ml L2K | | |
| C2C12 | mouse | adherent | myoblast | 50 nM | 2 ug/ml L2K | | |
| Primary endothelium | mouse | adherent | endothelial | 200 nM | 2 ug/ml L2K 0.25 uM EPEI | | |
| MCF7 | human | adherent | breast adenocarcinoma | 500 nM | 3 ug/ml L2K (while plating) | | |
| RAW 264.7 | mouse | adherent | osteoclast | 150 nM | 2 ug/ml L2K | 75-300 nM | |
| Jurkat | human | suspension | acute t-cell leukemia | 50 uM. | Electroporation 100 volts 50% modulation 25 Khz 2 msec 10 bursts | | |
| THP-1 | human | suspension | acute monocytic leukemia | 50 uM | Electroporation 100 volts 100% modulation 25 Khz 2 msec 10 bursts | | |
| Hut-78 | human | suspension | human t-cell | 50 uM | Electroporation 100 volts | | |

| Cell Line | Species | Type | Description | Opt. Duplex Conc. | Optimal Lipid Conc. | Duplex Range | Lipid Range |
|---|---|---|---|---|---|---|---|
| | | | | | 80% n modulation 25 Khz 2 msec 10 bursts | | |

Seven Steps Toward RNAi Success

1. Optimize Transfection Conditions Before Beginning Experiments with Stealth™ RNA.

The level of confluence and passage number of the cells at the start of transfection can have a significant impact on the efficiency of Stealth™ RNA uptake and on the cellular toxicity associated with transfection. Before beginning RNAi analysis, optimize transfection conditions by determining the optimal cell density and oligomer-lipid concentrations to use for the mammalian cell line of interest and system. When optimizing transfection conditions, follow these guidelines: (1) To ensure uniform uptake of Stealth™ RNA, make sure that cells are plated uniformly across the wells; (2) For highly efficient transfection in a broad range of mammalian cell types, use Lipofectamine™ 2000 Reagent; (3) Use the BLOCK-iT™ Fluorescent Oligo to optimize transfection conditions as described above. Uptake of the BLOCK-iT™ Fluorescent Oligo correlates strongly with uptake of Stealth™ RNA or siRNA oligomers.

2. Include the BLOCK-iT™ Fluorescent Oligo in Every Experiment.

The degree of the RNAi response to a particular Stealth™ RNA or siRNA oligomer is directly linked to its transfection efficiency. To assess transfection efficiency, include the BLOCK-iT™ Fluorescent Oligo in every experiment. Using the BLOCK-iT™ Fluorescent Oligo in transfection experiments allows for easy assessment of oligomer uptake and transfection efficiency using any fluorescence microscope and a standard FITC filter set. Uptake of the fluorescent oligomer by at least 80% of cells correlates with high levels of gene knockdown by effective Stealth™ RNA or siRNA oligomers. Note that the BLOCK-iT™ Fluorescent Oligo is chemically modified to enhance its stability and allows assessment of fluorescence signal for a significantly longer time period than is obtained with other unmodified, fluorescently-labeled RNA.

3. Assess Stealth™ RNAi or siRNA Effects by Performing an RNA Assay (i.e. qRT-PCR) First.

To validate Stealth™ RNA or siRNA oligomers, measure each oligomer's effect on the target mRNA. Although many investigators wish to bypass the RNA determination step and look directly at the Stealth™ RNA or siRNA oligomer's effect on protein levels, this is unadvisable, since the RNA assay will yield important information about the rank order potency of the oligomers against the target mRNA and provides valuable information required to troubleshoot the assay system. For example, an RNAi oligomer may be effective at decreasing mRNA levels of the target gene; however, may not affect protein levels if the target protein has a long half-life. Quantitative RT-PCR (qRT-PCR) using custom LUX™ primers (Invitrogen Corp., Carlsbad, Calif.) provides a convenient and high throughput method to evaluate the effect of an individual or set of Stealth™ RNA or siRNA oligomers on target mRNA levels. The LUX™ Designer available at www.invitrogen.com/lux may be used to help design and order suitable primers for use in qRT-PCR analysis. To prepare mRNA or total RNA from untreated or oligomer-treated cells, mRNA Catcher™ Kit (Invitrogen Corp., Carlsbad, Calif.) or Concert™ 96 RNA Purification System (Invitrogen Corp., Carlsbad, Calif.) may be used, respectively. When performing qRT-PCR, results should be normalized to an internal control RNA (e.g. β-actin or GAPDH).

4. Know the Half-Life of the Protein that You Wish to Inhibit.

To see Stealth™ RNA or siRNA-mediated inhibition at the protein level, any pre-existing pool of the protein must be degraded. If the protein of interest has a long half-life, long-term transfection experiments may need to performed (i.e. perform multiple cycles of transfection) to observe effects at the protein level.

5. Always Include the Appropriate Positive and Negative Controls.

When performing RNAi analysis, it is important to include the proper positive and negative controls to help evaluate experimental results. For a positive control, include an effective Stealth™ RNA for a target other than the mRNA of interest. For a negative control, compare the levels of the target mRNA in Stealth™ RNA or siRNA-treated and control (scrambled or reverse sequences)-treated cells, for example by using the BLOCK-iT™ Transfection Optimization Kit as described previously.

6. Follow these General Guidelines to Perform RNAi Analysis Using Stealth™ RNA or siRNA.

When preparing oligomer-lipid complexes, dilute oligomer and lipid into the appropriate medium, for example Opti-MEM® I Reduced Serum Medium. Do not use phosphate-buffered saline (PBS) for dilution, as transfection efficiency will be severely compromised. Always mix the Stealth™ RNA or siRNA oligomer stock solution thoroughly before use. Thaw, vortex, and spin to collect fluid before removing sample. Do not allow the cells to dry out before adding oligomer-lipid complexes. Doing so will reduce the transfection efficiency and cell viability. For detailed protocols to transfect Stealth™ RNA or siRNA oligomers, refer to the manufacturer's instructions for the transfection reagent being using.

7. Visit www.invitrogen.com/rnai for Additional Information, Resources, and Protocols to Help Achieve RNAi Analysis Success.

EQUIVALENTS

Those skilled in the art will recognize, or be able to ascertain using no more than routine experimentation, many equivalents to the specific embodiments of the invention described herein. Such equivalents are intended to be encompassed by the following claims. The entire contents of all patents, published patent applications and other references cited herein are hereby expressly incorporated herein in their entireties by reference.

The invention claimed is:

1. A composition comprising a double-stranded oligonucleotide molecule, the molecule comprising:
a first strand and a second strand each having a length of less than 25 nucleotides and having a duplex length of at least 10 to at least 24 nucleotides;
wherein at least one of the first strand and the second strand contains a 5'-terminal phosphorous containing moiety;
wherein at least one but not all of the nucleotides of the first strand comprises a 2'-O-methyl modification and at least one but not all of the nucleotides of the second strand comprises a 2'-O-methyl modification, and
wherein said double-stranded oligonucleotide molecule is chemically synthesized.

2. The composition of claim 1, wherein a strand of said double-stranded oligonucleotide molecule is complementary to a sequence of a target nucleic acid.

3. The composition of claim 2 wherein the target nucleic acid is a mRNA or a gene.

4. The composition of claim 2 wherein the target nucleic acid is present within a cell.

5. The composition of claim 4 wherein the cell is a eukaryotic cell.

6. The composition of claim 1 wherein the phosphorus containing moiety is selected from phosphate, phosphorothioate, or P-ethoxyphosphate.

7. The composition of claim 1 wherein the double-stranded oligonucleotide molecule is a double-stranded ribonucleic acid molecule.

8. A method for introducing a double-stranded ribonucleic acid molecule comprising a first strand and a second strand into a eukaryotic cell in vitro, the method comprising contacting the eukaryotic cell with the double-stranded ribonucleic acid molecule,
wherein the first strand and the second strand each have a length of less than 25 nucleotides and have a duplex length of at least 10 to at least 24 nucleotides,
wherein at least one but not all of the nucleotides of the first strand of the double-stranded ribonucleic acid molecule comprises a 2'-O-methyl modification;
wherein at least one but not all of the nucleotides of the second strand of the double-stranded ribonucleic acid molecule comprises a 2'-O-methyl modification;
wherein at least one of the first strand and the second strand contains a 5'-terminal phosphorus containing moiety; and
wherein said double-stranded ribonucleic acid molecule is chemically synthesized; to result in the double-stranded nucleic acid molecule being introduced into the eukaryotic cell.

9. The method of claim 8, wherein the eukaryotic cell is contacted with the double-stranded ribonucleic acid molecule in the presence of a transfection agent.

10. The method of claim 9, wherein the transfection reagent is a cationic lipid.

11. The method of claim 8, wherein the double-stranded ribonucleic acid molecule is introduced into the cell by electroporation.

12. The method of claim 8, wherein a strand of said double-stranded ribonucleic acid molecule is complementary to a sequence of an mRNA expressed in said eukaryotic cell.

13. The method of claim 8, wherein a strand of the double-stranded ribonucleic acid molecule has at least 80% sequence complementarity with an mRNA expressed in the eukaryotic cell.

14. The method of claim 8, wherein a strand of the double-stranded ribonucleic acid molecule has at least 90% sequence complementarity with an mRNA expressed in the eukaryotic cell.

15. The method of claim 8, wherein a strand of the double-stranded ribonucleic acid molecule has at least 95% sequence complementarity with an mRNA expressed in the eukaryotic cell.

16. The method of claim 8 wherein the phosphorus containing moiety is selected from phosphate, phosphorothioate, or P-ethoxyphosphate.

* * * * *

SEQUENCE LISTING

<160> NUMBER OF SEQ ID NOS: 49

<210> SEQ ID NO 1
<211> LENGTH: 66
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ucuugaacau gaguugaaag aaaaactcat gttcaagaca gaagggccga aagaaaggcc     60
cuucug                                                               66

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cccuucuguc uugaacauga g                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctgatgttca agacagaacg g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctgatgttca agacagaacg g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
ctcauguuca agacagaagg g                                              21

<210> SEQ ID NO 6
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
ctcauguuca agacagaagg g                                                 21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
ctcauguuca agacagaagg g                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagtacaagt tctgtcttcc c                                                 21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcaagacag aacttgtagt c                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaagacag aacttgtact c                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaagacag aacttgtact c                                                 21
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaagacag aacttgtact c                                           21

<210> SEQ ID NO 13
<211> LENGTH: 58
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
ggcccuucug ucuugaacau gaguugaaag aaaaactcat gttcaagaca gaagggcc    58

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ile Trp Leu Ile Tyr Leu Trp Ile Val
 1               5                  10

<210> SEQ ID NO 15
<211> LENGTH: 16
<212> TYPE: PRT
<213> ORGANISM: Unknown Organism
<220> FEATURE:
<223> OTHER INFORMATION: Description of Unknown Organism: Antennapedia
      protein

<400> SEQUENCE: 15

Arg Gln Ile Lys Ile Trp Phe Gln Asn Arg Arg Met Lys Trp Lys Lys
 1               5                  10                  15

<210> SEQ ID NO 16
<211> LENGTH: 27
<212> TYPE: PRT
<213> ORGANISM: Unknown Organism
<220> FEATURE:
<223> OTHER INFORMATION: Description of Unknown Organism: Transportan
      protein

<400> SEQUENCE: 16

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
             20                  25

<210> SEQ ID NO 17
<211> LENGTH: 25
<212> TYPE: PRT

```
<213> ORGANISM: Human immunodeficiency virus
<220> FEATURE:
<221> NAME/KEY: MOD_RES
<222> LOCATION: (1)
<223> OTHER INFORMATION: C(Acm)

<400> SEQUENCE: 17

Cys Phe Ile Thr Lys Ala Leu Gly Ile Ser Tyr Gly Arg Lys Lys Arg
 1               5                  10                  15

Arg Gln Arg Arg Arg Pro Pro Gln Cys
            20                  25

<210> SEQ ID NO 18
<211> LENGTH: 15
<212> TYPE: PRT
<213> ORGANISM: Human immunodeficiency virus
<220> FEATURE:
<221> NAME/KEY: MOD_RES
<222> LOCATION: (1)
<223> OTHER INFORMATION: C(Acm)

<400> SEQUENCE: 18

Cys Gly Arg Lys Lys Arg Arg Gln Arg Arg Arg Pro Pro Gln Cys
 1               5                  10                  15

<210> SEQ ID NO 19
<211> LENGTH: 19
<212> TYPE: PRT
<213> ORGANISM: Human immunodeficiency virus
<220> FEATURE:
<221> NAME/KEY: MOD_RES
<222> LOCATION: (1)
<223> OTHER INFORMATION: C(Acm)

<400> SEQUENCE: 19

Cys Leu Gly Ile Ser Tyr Gly Arg Lys Lys Arg Arg Gln Arg Arg Pro
 1               5                  10                  15

Pro Gln Cys

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Cys Phe Ile Thr Lys Ala Leu Gly Ile Ser Tyr Gly Arg Lys Lys
 1               5                  10                  15

Arg Arg Gln Arg Arg Arg Pro Pro Gln Gly Ser Gln Thr His Gln Val
            20                  25                  30

Ser Leu Ser Lys Gln
        35

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
```
accucaaagc uguuccguct t                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
gacggaacag cuuugagggut t                                          21

<210> SEQ ID NO 23
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
acgcacaccu caaagcuguu ccguccc                                     27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gggacggaac agctttgagg tgtgcgt                                     27

<210> SEQ ID NO 25
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
acgcacaccu caaagcuguu ccguccc                                     27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggacggaac agctttgagg tgtgcgt                                     27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 27
ccctgccttg tcgaaactcc acacgca                                              27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgcgtgtgga gtttcgacaa ggcaggg                                              27

<210> SEQ ID NO 29
<211> LENGTH: 32
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
ccctcacgca caccucaaag cuguuccguc cc                                        32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gggacggaac agctttgagg tgtgcgtgag gg                                        32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccctgccttg tcgaaactcc acacgcactc cc                                        32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gggagtgcgt gtggagtttc gacaaggcag gg                                        32

<210> SEQ ID NO 33
<211> LENGTH: 32
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
ccctcacgca caccucaaag cuguuccguc cc                                   32

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gggacggaac agctttgagg tgtgcgtgag gg                                   32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccctgccttg tcgaaactcc acacgcactc cc                                   32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggagtgcgt gtggagtttc gacaaggcag gg                                   32

<210> SEQ ID NO 37
<211> LENGTH: 32
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
cccuucuguc uugaacauga gttttttatg gc                                   32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gccataaaaa actcatgttc aagacagaag gg                                   32
```

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cggtattttt tgagtacaag ttctgtcttc cc                                32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gggaagacag aacttgtact caaaaaatac cg                                32

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cccttctgtc ttgaacatga gtttttatg gcgggag                            37

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctcccgccat aaaaaactca tgttcaagac agaaggg                           37

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gagggcggta tttttgagt acaagttctg tcttccc                            37

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaagacag aacttgtact caaaaaatac cgccctc                           37

<210> SEQ ID NO 45

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
accucaaagc uguuccguct t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
gacggaacag cuuugaggut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
cccuucuguc uugaacaugt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
cauguucaag acagaagggt t                                              21

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Glu Val Asp
 1
```